US008202716B2

(12) United States Patent
Thompson et al.

(10) Patent No.: US 8,202,716 B2
(45) Date of Patent: *Jun. 19, 2012

(54) THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS

(75) Inventors: David N. Thompson, Idaho Falls, ID (US); William A. Apel, Jackson, WY (US); Vicki S. Thompson, Idaho Falls, ID (US); David W. Reed, Idaho Falls, ID (US); Jeffrey A. Lacey, Idaho Falls, ID (US); Emily D. Henriksen, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 2 days.

This patent is subject to a terminal disclaimer.

(21) Appl. No.: 12/927,490

(22) Filed: Nov. 15, 2010

(65) Prior Publication Data

US 2012/0015407 A1    Jan. 19, 2012

Related U.S. Application Data

(62) Division of application No. 12/322,359, filed on Jan. 29, 2009, now Pat. No. 7,858,353.

(60) Provisional application No. 61/025,136, filed on Jan. 31, 2008.

(51) Int. Cl.
*C12N 9/42* (2006.01)
*C12N 9/14* (2006.01)
*C12N 9/00* (2006.01)
*C12P 21/06* (2006.01)
*C08B 37/00* (2006.01)
*D21C 1/00* (2006.01)
*C02F 3/34* (2006.01)
*C07H 21/04* (2006.01)
*C07K 1/00* (2006.01)

(52) U.S. Cl. ....... 435/209; 435/195; 435/183; 435/69.1; 435/274; 435/277; 435/262; 536/23.2; 536/23.7; 530/350

(58) Field of Classification Search ................. 435/209, 435/195, 183, 69.1, 274, 277, 262; 536/23.2, 536/23.7; 530/350
See application file for complete search history.

(56) References Cited

U.S. PATENT DOCUMENTS

| 4,237,226 A | 12/1980 | Grethlein |
| 4,581,333 A | 4/1986 | Kourilsky et al. |
| 4,624,922 A | 11/1986 | Horikoshi et al. |
| 5,098,825 A | 3/1992 | Tchen et al. |
| 5,882,905 A | 3/1999 | Saha et al. |
| 5,916,795 A | 6/1999 | Fukunaga et al. |
| 5,948,667 A | 9/1999 | Cheng et al. |
| 6,083,733 A | 7/2000 | Gronberg et al. |
| 6,268,197 B1 | 7/2001 | Schulein et al. |
| 6,426,211 B1 | 7/2002 | De Buyl et al. |
| 6,506,585 B2 | 1/2003 | Danielsen et al. |
| 6,777,212 B2 | 8/2004 | Asakura et al. |
| 6,833,259 B2 | 12/2004 | Bhosle et al. |
| 7,727,755 B2 | 6/2010 | Thompson et al. |
| 2003/0134395 A1 | 7/2003 | Shetty |
| 2003/0233675 A1 | 12/2003 | Cao et al. |
| 2004/0029129 A1 | 2/2004 | Wang et al. |
| 2005/0112742 A1 | 5/2005 | Thompson et al. |
| 2006/0105442 A1 | 5/2006 | Wu et al. |
| 2006/0211083 A1 | 9/2006 | Katzen et al. |
| 2007/0082381 A1 | 4/2007 | Wilting et al. |
| 2007/0134778 A1 | 6/2007 | Benning et al. |
| 2007/0148728 A1 | 6/2007 | Johnson et al. |
| 2009/0203107 A1 | 8/2009 | Thompson et al. |
| 2009/0215168 A1 | 8/2009 | Lee et al. |
| 2009/0221049 A1 | 9/2009 | Shaw et al. |
| 2009/0226978 A1 | 9/2009 | Thompson et al. |
| 2009/0253205 A1 | 10/2009 | Thompson et al. |
| 2009/0263859 A1 | 10/2009 | Thompson et al. |
| 2009/0269827 A1 | 10/2009 | Thompson et al. |
| 2010/0203583 A1 | 8/2010 | Thompson et al. |
| 2010/0311110 A1 | 12/2010 | Thompson et al. |
| 2011/0081683 A1 | 4/2011 | Thompson et al. |
| 2011/0275135 A1 | 11/2011 | Lee et al. |

FOREIGN PATENT DOCUMENTS

| DE | 197 17 893 A1 | 1/1999 |
| WO | 81/00577 | 3/1981 |
| WO | 99/06584 A1 | 2/1999 |
| WO | 03/068926 | 8/2003 |
| WO | 2005/066339 | 7/2005 |
| WO | 2006/117247 A1 | 11/2006 |

OTHER PUBLICATIONS

PCT International Search Report and Written Opinion of the International Searching Authority for PCT/US09/00442, dated May 18, 2009, 8 pages.
PCT International Search Report and Written Opinion of the International Searching Authority for PCT/US09/34701, dated Jan. 12, 2010, 10 pages.
PCT International Search Report and Written Opinion of the International Searching Authority for PCT/US09/35275, dated Feb. 25, 2010, 13 pages.

(Continued)

*Primary Examiner* — Ganapathirama Raghu
(74) *Attorney, Agent, or Firm* — TraskBritt

(57) ABSTRACT

Isolated and/or purified polypeptides and nucleic acid sequences encoding polypeptides from *Alicyclobacillus acidocaldarius* are provided. Further provided are methods of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan-, or mannan-decorating groups using isolated and/or purified polypeptides and nucleic acid sequences encoding polypeptides from *Alicyclobacillus acidocaldarius*.

11 Claims, 75 Drawing Sheets

OTHER PUBLICATIONS

PCT International Search Report and Written Opinion of the International Searching Authority for PCT/US09/35331, dated Feb. 23, 2010, 10 pages.

PCT International Search Report and Written Opinion of the International Search Authority for PCT/US09/35307, dated Jun. 10, 2010, 10 pages.

PCT International Search Report and Written Opinion of the International Search Authority for PCT/US10/25521, dated Jul. 14, 2010, 12 pages.

Pearson and Lipman, Proc. Natl. Acad. Sci. (U.S.A.) 85: 2444 (1988).

Sanchez-Pescador, R., 1988, J. Clin. Microbiol., 26(10): 1934-1938.

Schafer et al., "X-ray Structures of the Maltose-Maltodextrin-binding Protein of the Thermoacidophilic Bacterium Alicyclobacillus acidocaldarius Provide Insight into Acid Stability of Proteins," J. Mol. Biol. 2004, 335:261-274.

Schäffer, C. et al., 2001, Prokaryotic glycosylation. Proteomics, 1: 248-261.

Scheffel et al., "Functional reconstitution of a maltrose ATP-binding cassette transporter from the thermoacidophilic gram-positive bacterium Alicyclobacillus acidocaldarius," Biochem Biophy Acta, 2004, 1656(1):57-65.

Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.

Schwermann, B. et al., 1994, Purification, properties and structural aspects of a thermoacidophilic a-amylase from Alicyclobacillus acidocaldarius ATCC 27009, insight into acidostability of proteins. Eur. J. Biochem. 226: 981-991.

Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).

Shallom et al., "Microbial hemicellulases," Current Opinion in Microbiology, Current Biology Ltd, GB, vol. 6, No. 3, Jun. 1, 2003, pp. 219-228.

Supplemental European Search Report for EP 06 82 7231, dated Nov. 12, 2009, 6 pages.

Tsao, GT, MR Ladisch, and HR Bungay, 1987. Biomass Refining, In Advanced Biochemical Engineering, Wiley Interscience, N.Y., 79-101.

Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?]

UniProtKB/TrEMBL Q9JRQ1 [online]. Oct. 1, 2000. Available on the internet at <<URL://http://www.uniprot.org/uniprot/Q9JRQ1>>.

Upreti et al., 2003, Bacterial glycoproteins: Functions, biosynthesis and applications. Proteomics, 3: 363-379.

Urdea, M. S., 1988, Nucleic Acids Research, II: 4937-4957.

Vieille and Zeikus, 2001, Micro. and Mol. Biol. Rev., vol. 65, No. 1, p. 1-43.

Walker, G. T. et al., 1992, NAR 20: 1691-1696.

Walker, G.T. et al., 1992, PNAS. USA, 89:392-396.

Whisstock et al. "Prediction of Protein Function from Protein Sequence and Structure" Quarlty Reviews of Biophysics 36, 3 (2003) pp. 307-340 (35 pages).

Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).

International Search Report of the International Searching Authority for PCT/US06/42566, dated Jul. 25, 2008.

PCT International Preliminary Report on Patentability of the International Search Authority for PCT/US09/32333, dated Aug. 3, 2010.

PCT International Preliminary Report on Patentability of the International Searching Authority for PCT/US09/00442, dated Jul. 27, 2010.

PCT International Preliminary Report on Patentability of the International Searching Authority for PCT/US09/34701, dated Aug. 24, 2010.

PCT International Preliminary Report on Patentability of the International Searching Authority for PCT/US09/35275, dated Aug. 31, 2010.

PCT International Preliminary Report on Patentability of the International Searching Authority for PCT/US09/35331, dated Aug. 31, 2010.

PCT International Preliminary Report on Patentability of the International Search Authority for PCT/US09/35307, mailed Jan. 25, 2011.

PCT International Search Report of the International Search Authority for PCT/US10/25521 Jul. 14, 2010.

Schwarz, Wolfgang H., "A list of cellulolytic bacteria," Technische Universitat Munchen, Apr. 24, 2003, 8 pages.

Simpson et al., "An extremely Thermostable xylanase from the thermophilic eubacterium Thermotoga," Biochem. J. (1991) 277, 413-417.

Smook, G.A., "Handbook for Pulp & Paper Technologists," Tappi Pr; 2nd Ed. (Jun. 1992) pp. 65-88.

Subramaniyan et al., "Cellulase-free xylanases from Bacillus and other microorganisms," FEMS Microbiology Letters 183 (2000) 1-7.

Sunna et al., "Glycosyl hydrolases from hyperthermophiles," Extremophiles (1997) 12-13.

Techapun et al., "Production of a cellulose-free xylanase from agricultural waste materials by a thermotolerant Streptomyces sp.," Biotechnology Letters 23: 1685-1689, 2001.

Thompson et al., "Comparison of Pretreatment Methods on the Basis of Available Surface Area," Bioresource Technology 39 (1992) 155-163.

Thompson et al., "In Vitro Degradation of Natural Insoluble Lignin in Aqueous Media by the Extracellular Peroxidases of Phanerochaete chrysosporium," 1998 John Wiley & Sons, Inc. pp. 704-717.

Thompson et al., "Measurement of fumonsins in corn with a fiberoptic fluoroimmunosensor," SPIE vol. 2980, (2010) pp. 532-538.

Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.

Thompson et al., "Purification and Characterization of a Novel Thermo-Alkali-Stable Catalase from Thermus brockianus," Biotechnol. Prog. 2003, 19, 1292-1299.

Thompson et al., "Thermoacidophilic Cellulases and Hemicellulases from Alicyclobacillus acidocaldarius," Idaho National Laboratory, 2006, 1 page.

Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SS, USA. Kirk, T.K. and Chang, H.M. (eds.). Butterworth-Heinemann, Boston, 1990, pp. 329-338.

Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.

Turner et al., "Potential and utilization of thermophiles and thermostable enzymes in biorefining," Microbial Cell Factories, Biomed Central, London, NL, vol. 6, No. 1, Mar. 15, 2007, p. 9.

Uhl et al., "The first description of an archaeal hemicellulase: the xylanase from Thermococcus zilligii strain AN1," Extremophiles (1999) 3:263-267.

Viikari et al., "Xylanases in bleaching: From an idea to the industry," FEMS Microbiology Reviews 13 (1994) 335-350.

Walseth, Curtis S., Occurrence of Cellulases in Enzyme Preparations from Microorganisms, TAPPI vol. 35, No. 5, May 1952, pp. 228-233.

Ward et al., "Characterization of a new bacteriophage which infects bacteria of the genus Acidiphilium," Journal of General Virology (1993) 74: 2419-2425.

Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.

Wright et al., "Ethanol from Biomass by Enzymatic Hydrolysis," Chemical Engineering Progress, Aug. 1988, pp. 62-74.

Yuan et al., Expression of acidophilic alpha-amylase from Alicyclobacillus acidocaldarius, Sheng Wu Gong Cheng Xue Bao, Jan. 2005, 21(1):78-83. Abstract only.
Bhatia et al., "Microbial beta-Glucosidases: Cloning, Properties, and Applications," Critical Reviews in Biotechnology, 22(4):375-407, Jan. 1, 2002.
Breves et al., "Genes Encoding Two Different beta-Glucosidases of Thermoanaerobacter brockii Are Clustered in a Common Operon," Applied and Environmental Microbiology, vol. 63, No. 10, Oct. 1997, pp. 3902-3910.
Database EMBL [Online]. Mar. 16, 2007. XP-002627757. Database accession No. ER073884, 1 page.
Database Geneseq [Online]. May 21, 1998. XP-002627734. Database accession No. AAW35004, 1 page.
Database UniProt [Online]. May 1, 1997. XP-002630045. Database accession No. P96090, 1 page.
Database UniProt [Online]. Oct. 1, 2001. XP-002627736. Database accession No. Q97UI4, 1 page.
Database UniProt [Online]. Jun. 26, 2007. XP-002627735. Database accession No. A5IKZ4, 1 page.
Database UniProt [Online]. Nov. 3, 2009. XP-002627733. Database accession No. C8WTP2, 1 page.
Extended Supplementary European Search Report for EP 09 70 3173, dated Apr. 20, 2011, 7 pages.
Bork, Peer, "Powers and Pitfalls in Sequence Analysis: The 70% Hurdle," Genome Research, 2000, 10:398-400.
Bowie et al., "Deciphering the Message in Protein Sequences: Tolerance to Amino Acid Substitutions," Science, 1990, 247:1306-1310.
Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.
Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).
Badger, P.C., "Ethanol from cellulose: A general review," In: J. Janick and A. Whipkey (eds.), Trands in new crops and new uses. ASHS Press, Alexandria, VA, 2002, pp. 17-21.
Bailey et al., "Interlaboratory testing of methods for assay of xylanase activity," Journal of Biotechnology, 23 (1992) 257-270.
Bergquist et al., "Molecular diversity of thermophilic cellulolytic and hemicellulolytic bacteria," FEMS Microbiology Ecology 28 (1999) 99-110.
Cowling, Ellis B., "Physical and Chemical Constrains in the Hydrolysis of Cellulose and Lignocellulosic Materials," Biotechnol. & Bioeng. Symposium No. 5, 163-181 (1975).
Crout et al., "Glycosidases and glycosyl transferases in glycoside and oligosaccharide synthesis," Current Opinion in Chemical Biology, Current Biology Ltd, London, GB, vol. 2, No. 1, Feb. 1, 1998, pp. 98-111.
Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.
Database UniProt [Online]. Feb. 10 2009. XP-000002659383. Database accession No. B7DT70, 1 page.
Ehrman, Tina, "Standard Method for Determination of Total Solids in Biomass," Chemical Analysis and Testing Task, Laboratory Analytical Procedure, Oct. 28, 1994, 242 total pages.
EMBL Submission CP001728, Sep. 2009. [Retrieved from the internet: URL:http://www.ebi.ac.uk/Tools/dbfetch/embifetch?style=html&id=CP001728&Submit=Go], 51 pages.
Extended Supplementary European Search Report for EP 09 82 3952, dated Sep. 20, 2011, 7 pages.
Fan et al., "The Nature of Lignocellulosics and Their Pretreatments for Enzymatic Hydrolysis," Advances in Biochemical Engineering/Biotechnology, 1982, vol. 23/1982, 157-187.
Flanagan, et al., "Development of gas phase bioreactors for the removal of nitrogen oxides from synthetic flue gas streams," Fuel 81 (2002) 1953-1961.

Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.
Gessesse, Amare, "Purification and Properties of Two Thermostable Alkaline Xylanases from an Alkaliphilic Bacillus sp.," Applied and Environmental Microbiology, Sep. 1998, pp. 3533-3535.
Glenn et al., "Transformation of Acidiphilium by electroporation and conjugation," Can J Microbiol. May 1992;38 (5):387-93.
Goldstein et al., "The Hydrolysis of Cellulose with Superconcentrated Hydrochloric Acid," Biotechnology and Bioengineering Symp. No. 13, pp. 17-25 (1983).
Grassin et al., "Chapter 2.13, Fruit Juices," (T. Godfrey and S. West, eds.), Industrial Enzymology, 2nd Ed., pp. 227-264 (1996).
Grethlein, H. E., "Pretreatment for enhanced hydrolysis of cellulosic biomass," Biotechnol. Adv. 1984. 2:43-62.
Grethlein, Hans E., "Comparison of the Economics of Acid and Enzymatic Hydrolysis of Newsprint," Biotechnology and Bioengineering, vol. XX, pp. 503-525 (1978).
Hanselmann, K.W., "Lignochemicals," Experientia 38 (1982) pp. 176-189.
Houghton et al., "Fungal Upgrading of Wheat Straw for Straw-Thermoplastics Production," Applied Biochemistry and Biotechnology, vol. 113-116, 2004, pp. 71-93.
Keller et al., "Microbial Pretreatment of Biomass: Potential for Reducing the Severity of Thermochemical Biomass Pretreatment," Applied Biochemistry and Biotechnology, vol. 105-108, 2003.
Kenealy et al., "Rapid 2,2-bicinchoninic-based xylanase assay compatible with high throughput screening," Biotechnology Letters 25: 1619-1623, 2003.
Knappert et al., "Partial Acid Hydrolysis of Cellulosic Materials as a Pretreatment for Enzymatic Hydrolysis," Biotechnology and Bioengineering, vol. XXII, pp. 1449-1463 (1980).
Kulkarni et al., "Molecular and biotechnological aspects of xylanases," FEMS Microbiology Reviews 23 (1999) 411-456.
Lauro et al., "Characterization of a β-glycosidase from the thermoacidophilic bacterium Alicyclobacillus acidocaldarius," Extremophiles (2006) 10:301-310.
Lee et al., "Oxygen Effects on Thermophilic Microbial Populations in Biofilters Treating Nitric Oxide Containing Off-Gas Streams," Environmental Progress, vol. 20, No. 3, Oct. 2001.
Lynd, Lee R., "Overview and Evaluation of Fuel Ethanol from Cellulosic Biomass: Technology, Economics, the Environment, and Policy," Annu. Rev. Energy Environ. 1996, 21:403-65.
MacKenzie et al., "Multiple Chromosomes in Bacteria: The Yin and Yang of trp Gene Localization in Rhodobacter sphaeroides 2.4.1," Genetics 153: 525-538 (Oct. 1999).
Manchenko, Gennady P., "Handbook of Detection of Enzymes on Electrophoretic Gels," CRC Press, Inc. 1994, pp. 220-240.
McCoy, Michael, "Chemical Makers Try Biotech Paths," Chemical Engineering News, Jun. 22, 1998, pp. 13-19.
Michel et al., "Specificity of the protein secretory apparatus: secretion of the heat-labile enterotoxin B subunit pentamers by different species of Gram bacteria," Gene 152 (1995) pp. 41-45.
Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.
Ng et al., 1981, Applied and Environmental Microbiology, 41(6):1337-1343.
Ohta et al., "Purification and Characterization of an Acidophilic Xylanase from Aureobasidium pullulans var. melanigenum and Sequence Analysis of the Encoding Gene," Journal of Bioscience and Bioengineering, vol. 92, No. 3, 262-270, 2001.
Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.
Pajunen et al., Microbiology (2005) 151, 1209-1218.
Patel et al., (2006), "Medium and long-term opportunities and risks of the biotechnological production of bulk chemicals from renewable resources: The potential of white biotechnology". The BREW Project. Final Report prepared under the European Commission's GROWTH Programme (DG Research), (publica.fraunhofer.de/eprints/N-48834.pdf).

PCT International Search Report and Written Opinion of the International Searching Authority for PCT/US10/51095, dated Dec. 2, 2010, 11 pages.

PCT International Search Report and Written Opinion of the International Search Authority for PCT/US11/34852, dated Oct. 21, 2011, 12 pages.

Perlack et al., "Biomass as Feedstock for a Bioenergy and Bioproducts Industry: The Technical Feasibility of a Billion-Ton Annual Supply," USDA and DOE, Apr. 2005, 78 pages.

Peyton et al., "Biotransformation of Toxic Organic and Inorganic Contaminants by Halophilic Bacteria," Halophilic Microorganisms, Antionio Ventosa (Ed.), Springer, 2004, pp. 315-331.

Ragauskas et al., "The Path Forward for Biofuels and Biomaterials," Science, Jan. 27, 2006, vol. 311, pp. 484-4589.

Ramos et al., "Biomechanical and Biochemical Pulping of Sugarcane Bagasse with Ceriporiopsis subvermispora Fungal and Xylanase Pretreatments," J. Agric. Food Chem. 2001, 49, 1180-1186.

Saeman et al., "Quantitative Saccharification of Wood and Cellulose," Industrial and Engineering Chemistry, Jan. 1945, vol. 17, No. 1, pp. 35-37.

Saha et al., "Dilute Acid Pretreatment, Enzymatic Saccharification, and Fermentation of Rice Hulls to Ethanol," Biotechnol. Prog. 2005, 21, 816-822.

Sa-Pereira et al., "Rapid production of thermostable cellulose-free xylanase by a strain of Bacillus subtilis and its properties," Enzyme and Microbial Technology, 30 (2002) 924-933.

Schell et al., "Dilute-Sulfuric Acid Pretreatment of Corn Stover in Pilot-Scale Reactor," Applied Biochemistry and Biotechnology, vol. 105-108, 2003, pp. 69-85.

Barany, F., PNAS. USA, 88: 189-193, 1991.

Bertoldo et al., 2004, Eng. Life Sci., 4, No. 6.

Blast Search of Seq. ID. 36, accessed Apr. 22, 2009, 54 pages.

Blast Search of Seq. ID. 456, accessed Apr. 22, 2009, 48 pages.

Blast Search of Seq. ID. 458, accessed Apr. 22, 2009, 59 pages.

Blast Search of Seq. ID. 460, accessed Apr. 22, 2009, 37 pages.

Blast Search of Seq. ID. 462, accessed Apr. 22, 2009, 35 pages.

Blast Search of Seq. ID. 464, accessed Apr. 22, 2009, 45 pages.

Borman, S., 2006, Glycosylation Engineering. Chem. Eng. News, 84(36): 13-22.

Broun et al. "Catalytic Plasticity of Fatty Acid Modification Enzymes Underlying Chemical Diversity of Plant Lipids" Science vol. 282 Nov. 13, 1998 pp. 1315-1317 (4 pages).

Buckholz, R. G., 1993, Yeast systems for the expression of heterologous gene products. Curr. Op. Biotechnology 4: 538-542.

Burg, J. L. et al., 1996, Mol. and Cell. Probes, 10: 257-271.

Chu, B. C. F. et al., 1986, NAR, 14: 5591-5603.

Collins et al., "Xylanaes, Xylanase Families and Extremophilic Xylanses," FEMS Microbiology Review, 2005, pp. 3-23.

Devos et al. "Practical Limits of Functiona Prediction" Proteins: Structure, Function, and Genetics 41 (2000) pp. 98-107 (10 pages).

Duck, P. et al., 1990, Biotechniques, 9: 142-147.

Eckert et al., "A Thermoacidophilic Endoglucanase (CelB), etc.," Eur. J. Biochem. 270, 2003, pp. 3593-3602.

Eckert et al., "Gene cloning, sequencing, and characterization of a family 9 endoglucanase (CeIA) with an unusual pattern of activity from the theremoacidophile Alicyclobacillus acidocaldarius ATCC27009," Applied Microbiology and Biotechnology, vol. 60, pp. 428-436 (2002).

Eckert, Kelvin, "Dissertation, Cloning and Characterization of two glycosidases from the acidothermophile Alicyclobacillus acidocaldarius ATCC27009," Berlin, Dec. 18, 1971, 113 pages.

Edwards, C. P., and Aruffo, A., 1993, Current applications of COS cell based transient expression systems. Curr. Op. Biotechnology 4: 558-563.

Erlich, H.A., J Clin. Immunol., Nov. 1989; 9(6):437-47.

Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.

GenBank: E17054.1 Direct Submission Alicyclobacillus acidocaldarius genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2&tool=Entr.

Guateli, J. C. et al., 1990, PNAS. USA, 87: 1874-1878.

Hamelinck, CN, G van Hooijdonk, and APC Faaij, 2005, Ethanol from lignocellulosic biomass: techno-economic performance in short-, middle-, and long-term, Biomass Bioenergy, 28:384-410.

Hulsmann et al., "Maltose and maltodextrin transport in the thermoacidophilic gram-positive bacterium Alicyclobacillus acidocaldarius is mediated by a high-affinity transport system that includes a maltose binding protein tolerant to low pH," J. Bacteriology, Nov. 2000, p. 6292-6301.

Huygen, K. et al., 1996, Nature Medicine, 2(8): 893-898.

International Application Published Under the Patent Cooperation Treaty, WO 2005/066339, Wilting et al, published Jul. 21, 2005.

International Preliminary Report on Patentability and Written Opinion of the International Searching Authority for PCT/US06/42566 datedApr. 23, 2009 (7 pages).

International Search Report and Written Opinion of the International Search Authority for PCT/US09/32333, mailed Jun. 19, 2009, 9 pages.

Ito et al., "Purification and properties of acid stable xylanases from Aspergillus kawachii," Bioscience Biotechnology and Biochemistry 56 (4):547-550, Apr. 1992.

Jeffries, 1996, Curr. Op. in Biotech., 7:337-342.

Jones et al., "Cloning and transcriptional analysis of the Thermoanaerobacter ethanolicus strain 39E maltose ABC transport system," Extremophiles 2002, 6:291-299.

Kievitis, T. et al., 1991, J. Virol. Methods, 35: 273-286.

Kohler, G. et al., 1975, Nature, 256(5517): 495497.

Kwoh, D. Y. et al., 1989, PNAS. USA, 86: 1173-1177.

Lauro et al., "Isolation and characterization of a new family 42 beta-galactosidase from the thermoacidophilic bacterium Alicyclobacillus acidocaldarius: Identification of the active site residues," Biochimica et Biophysica Acta 1784 (2008) 282-301.

Lavarack et al., "The acid hydrolysis of sugarcane begasse hemicellulose to produce xylose, arabinose, glucose and other products," Biomass and Bioenergy 23 (2002) 367-380.

Liu C, and CE Wyman, 2003, The effect of flow rate of compressed hot water on xylan, lignin, and total mass removal from corn stover, Ind. Eng. Chem. Res., 42:5409-5416.

Lucas et al., C4-Dicarboxylate Transporter/Malic Acid Transport Protein [Alicyclobacillus acidocaldarius LAA1], GenBank Direct Submission, Accession No. EED06059, Dec. 17, 2008 (Retrieved from the Internet Dec. 15, 2009: <URL:http://www.ncbl.nlm.nlh.gov/.

Luckow, V. A., 1993, Baculovirus systems for the expression of human gene products. Curr. Op. Biotechnology 4: 564-572.

Lynd et al., 2002, Micro. and Mol. Biol. Rev., vol. 66, No. 3, p. 506-577.

Malherbe and Cloete, 2002, Re/View in Environmental Science and Bio/Technology, 1: 105-114.

Matthews, J. A. et al., 1988, Anal. Biochem., 169: 1-25.

Merrifield, R. D., 1966, J. Am. Chem. Soc., 88(21): 5051-5052.

Miele, E. A. et al., 1983, J. Mol. Biol., 171: 281-295.

Mielenz, 2001, Curr. Op. in Micro., 4:324-329.

Neddleman and Wunsch, J. Mol. Biol. 48: 443 (1970).

Olins, P. O., and Lee, S. C., 1993, Recent advances in heterologous gene expression in E. coli. Curr. Op. Biotechnology 4: 520-525.

Lin et al., "Purification, Characterization, and Gene Cloning of Thermopsin, a Thermostable Acid Protease from Sulfolobus acidocaldarius," The Journal of Biological Chemistry, 1990, vol. 265, No. 3, pp. 1490-1495.

Extended Supplementary European Search Report for EP 09 70 9191, dated Mar. 29, 2012, 6 pages.

FIG 1A

| | | |
|---|---|---|
| 16078568 | 1 | MAKPKIGLALGSGGAR |
| 89099582 | 1 | MFDAEVSKFLTIARHESYIKGGMLMRQPVIGLALGSGGAR |
| 124524344 | 1 | MAGRPKIGLALGSGGAR |
| 15615150 | 1 | MGKVHRPKIGLALGSGGAR |
| 121533815 | 1 | MRPKIGLALGSGGLR |
| RAAC00169 | 1 | MPRAREDWRIAMSDKARARDNVKVGVALGSGGAK |

| | | |
|---|---|---|
| 16078568 | 17 | GLAHLGVLSSLHKHQIEVDMIAGSSMGALVGSFYAAGHDV |
| 89099582 | 41 | GFAHLGVIKVLKEEGINVDVIAGSSMGALVGCFYGAGLDI |
| 124524344 | 18 | GFAHIGVLKVFEEEGIPVDMISGSSIGALVAALYGAGRTV |
| 15615150 | 20 | GYAHIGVLKVLEQEKIPIDYLAGSSMGALVASLYGAGHPT |
| 121533815 | 16 | GLAHVGVLRVLEREGIPIDCIAGCSIGALVGALYCAGLDP |
| RAAC00169 | 35 | GFAHIGVLLALAEHGVPVHAIAGSSMGALVAGVYAMGVPP |

| | | |
|---|---|---|
| 16078568 | 57 | ATMKKVAKAFKRRLYADYTVPKLGFLKGDRVRQLVHAYTF |
| 89099582 | 81 | DRLYKLAGAFKRKYYLDFTVPKMGFLAGKKVKELIRLFTH |
| 124524344 | 58 | REMELLSGAFKRKYYLDFKIGKMGLISGKRIEDLIRLLVH |
| 15615150 | 60 | EHLIRFANLFKRKYYLDFTVPKMGFIAGHRVEELIRVLAK |
| 121533815 | 56 | DTIYKLAKHTKRRHWLDFIIPKMGIIAGERVLAMLKLLTQ |
| RAAC00169 | 75 | RVMRALAVNLRRRHWLDFTVPKMGFIQGEKVRTVVATMTR |

| | | |
|---|---|---|
| 16078568 | 97 | GKPIEELQIPLGIVACDLQTGEKIVFRKGSVSDAVRASIS |
| 89099582 | 121 | GKNLEDLDIPVRVVATDLKAGEKVVFSKGPIADAVRASIS |
| 124524344 | 98 | GKKLEELNPPVAVVAANLSNGEKTVFKKGPVQEAVRASIS |
| 15615150 | 100 | KKRVEELDPPVRIVAADLLKGERVILQEGDVAEAVRASIA |
| 121533815 | 96 | QKQFADLRIPLAVVATELTTGQEIVFQEGDVAQAVRASIS |
| RAAC00169 | 115 | QGTFADTAIPLAIVATDLIKRRLVVFRSGLIADAVRASIS |

| | | |
|---|---|---|
| 16078568 | 137 | IPGIFIPQRLDGRLLVDGAVVDRIPVSVV**KDMGADIIAS |
| 89099582 | 161 | IPGIFTPEKLEDRLLVDGGVIDRVPVSVV**EEMGADLIIAV |
| 124524344 | 138 | IPGIFVPKKIGGHLFVDGGVVDRVPVSVV**KEMGAELLIGV |
| 15615150 | 140 | IPGIFVPKNINDRLLIDGGVIDRVPVSVV**KEMGADLTIAV |
| 121533815 | 136 | VPGIFVPHRLNDMLLVDGAVINPTPIDVARRMGANIVIAV |
| RAAC00169 | 155 | IPGVFVPVVRDGAVYVDGGVLERVPVQACWDLGVDLVIAV |

| | | |
|---|---|---|
| 16078568 | 177 | DVSRVRKTETAVHIFDVIMQSMDILQNELVRHQTIAADIM |
| 89099582 | 201 | DVSRVKTSSDITSIFDVIMQSLDIMQMELVSNREIASDIM |
| 124524344 | 178 | DVSVMKKEAEIRHIYDVIMQSIDIMQMELAESRKTEAHVL |
| 15615150 | 180 | DLTIFREELEIRSVYDVILQTMDMMSKELVRVQEIDCTVM |
| 121533815 | 176 | DLAHAGTVCKITNTFDVIIQSIDIMERELFKHRQHYCDVL |
| RAAC00169 | 195 | DVGVTPRGTPPTSAMDVIMQSLELMQDEALRARDRGASLT |

| | | |
|---|---|---|
| 16078568 | 217 | IRPS....LETYSSSSFANIEEMISAGEEATNRMISKIRK |
| 89099582 | 241 | IRPH....VEMYSSRAFTNIEDIIRIGEEEARKQVPRIKE |
| 124524344 | 218 | IRPD....VSMYSSMAFTNAGQIIKIGEEAAKQSVTEIQQ |
| 15615150 | 220 | IRPMNDRYRSLSSSIDFEAVNDLILLGERAAIAKIPEIKD |
| 121533815 | 216 | IRPD....VAHITPSSFETFDECVALGEQAGEAALPKIKA |
| RAAC00169 | 235 | LVPE....VSHIGTAQLQRAAEAIDLGYQAAVAQLDRIWD |

FIG 1B

```
16078568    253 EIEN........WEGS
89099582    277 AIQN........WKGQEDDEEK
124524344   254 LLEK........WKEPDK
15615150    260 AIAT........WKETHYETDEKA
121533815   252 LLAEGGQRCITATGENPSRPSDSGG
RAAC00169   271 AIDR.........AGAFVS
```

FIG 2A

| | | |
|---|---|---|
| 15613871 | 1 | MANTHSPLSRPPVKKRWLHRVILSVCVLAFLGGLSIVGIS |
| RAAC00501 | 1 | MTNAG..........RWVLRIAVGVMVLAILAWLATMAIG |
| 125974699 | 1 | MRITVLTYSRQ..KSHIIRKIILFIVLLALIFSVVVSAVS |
| 5457696 | 1 | MIWTWTILLFLTIIFGFF |
| 14520481 | 1 | MIWTWTILLFLTIIFGFF |
| 40744233 | 1 | MATLSKHHLQP......LGPIHPPRLGSARANEVDAQPIF |

| | | |
|---|---|---|
| 15613871 | 41 | VYVGWNLSHPEREVID...ESPTDYGLLFEDVVFYSEKDE |
| RAAC00501 | 31 | YVVAEKLTHPARKPIS...TSPAAYGLKYESIRFPSRVDH |
| 125974699 | 39 | VIAGWKLIHPKRLNIL...DFSANIVPSYTDVSFKDINDE |
| 5457696 | 19 | AFVGYKMVTPPRRVGK...WTPKDLGFDYEKVEFKSR.DG |
| 14520481 | 19 | AFVGYKMVTPPRRVGK...WTPKDLGFDYEKVEFKSR.DG |
| 40744233 | 35 | IPVHDPLDHEAPAILHSPRDYDAAEARNSAVILVSGAGGG |

| | | |
|---|---|---|
| 15613871 | 78 | VELKGWWIPAQDNGEELGTDRAVVFSHGYRHSRLQGENDI |
| RAAC00501 | 68 | LMLAGWLIPAARP.....TDRIVIEAHGYRQNRVL.DHPA |
| 125974699 | 76 | FELKGWYFNVTGS......SKTVILAHGYGKNRLNFGENT |
| 5457696 | 55 | ITLRGWWIDQGKD.......ETVIVLHGYTASKWN.EVYM |
| 14520481 | 55 | ITLRGWWIDQGKD.......ETVIVLHGYTASKWN.EVYM |
| 40744233 | 75 | VSGPSGIYPSLADKLAILLGVHVVRLDYRVAARTDYCVPD |

| | | |
|---|---|---|
| 15613871 | 118 | LPFAKRLAQEGYHLLLFDYRGSGESGGTYTTIGQYETDDL |
| RAAC00501 | 102 | LPVAKALHDAGFAVLMFDFRDEGESPGSEVTVGDYELRDL |
| 125974699 | 110 | IHLIKSLLDKGYNVLAFDFRNSGESEGNKTTFGVCEKNDL |
| 5457696 | 87 | KPAIEIVANLGYNVLTFDFRAHGESEGSKTTIGDKEILDL |
| 14520481 | 87 | KPAIEIVANLGYNVLTFDFRAHGESEGSKTTIGDKEILDL |
| 40744233 | 115 | IAATMDYLQDNHGSTRFVVVGWSFGGSPCFTIAAQQPDRV |

| | | |
|---|---|---|
| 15613871 | 158 | LSAIAFVKAEKHVEEIAVIG.....WSMGAVSAILATQQS |
| RAAC00501 | 142 | LGAIDYAHKLG.YDEVGLIG.....YSMGASTALEATAAD |
| 125974699 | 150 | LGAIQYVKNKG.SEKIVLMG.....FSTGASACILAAAES |
| 5457696 | 127 | SGAIDWLLSNTNTKKIALIG.....FSMGAMVTIRALAED |
| 14520481 | 127 | SGAIDWLLSNTNTKKIALIG.....FSMGAMVTIRALAED |
| 40744233 | 155 | LGVATVASQTAQTSGVRKLSPRPLLVLHGSGDTCLPQRCS |

| | | |
|---|---|---|
| 15613871 | 193 | EDVQIVIADSPF..ANLRQYLSENLSHWSDLPDVPFTWVV |
| RAAC00501 | 176 | PSVDATIADSPF..DDLETYLEQNLSVWTNLPSFPFNGEI |
| 125974699 | 184 | DDVDAVIAESPY..SDLNTYFEQNVNNLTNFPAIPFNKTI |
| 5457696 | 162 | ERVCCGIADSPP..IYIDKTGARGLKYFANLPEFLYPIIK |
| 14520481 | 162 | ERVCCGIADSPP..IYIDKTGARGLKYFANLPEFLYPIIK |
| 40744233 | 195 | ESLYQQYGDDPSGSREIKIFKGDNHGLSRNAPEAEGMLLV |

| | | |
|---|---|---|
| 15613871 | 231 | LQTIPVLIGADIDQVSPVDAVSPIGETKLFLIHGRWD... |
| RAAC00501 | 214 | LWEVKHLFGLDPNAVDPLKQLASAKPRPILLIAGTAD... |
| 125974699 | 222 | TFATFFLADIKPDEASPVKAVQAVSPRPVLLIHSKDD... |
| 5457696 | 200 | PFTKMFSGAKEVNIIDYADKVR....KPLLIIAGGND... |
| 14520481 | 200 | PFTKMFSGAKEVNIIDYADKVR....KPLLIIAGGND... |
| 40744233 | 235 | FAAKALGLEDELTAASVRIAAQDWVGSEGERMKEMAEGHD |

FIG 2B

| | | |
|---|---|---|
| 15613871 | 268 | .......EAIPHRDSEAIFEAADG...QAELWLPENEGHV |
| RAAC00501 | 251 | .......TTIPPSNSEALYDELHRRDPEDTLWLVPGAKHV |
| 125974699 | 259 | .......TKVPVENSRLIYKASNP..YTTTFWETSGADHE |
| 5457696 | 233 | .......PLVKVEEVEEFYKRNKTINPRIEVWIT.DAAHV |
| 14520481 | 233 | .......PLVKVEEVEEFYKRNKTINPRIEVWIT.DAAHV |
| 40744233 | 275 | FEGGEALNHNSITSPQALFDHVEREDRQGGSGLSGIAGSY |

| | | |
|---|---|---|
| 15613871 | 298 | KTINEQSEE...YEERILAFLEKSFTE |
| RAAC00501 | 284 | GAYDVEPKA...YLERVVDFFEAYMPVKVTSS |
| 125974699 | 290 | EIYQANPEE...YVKKVTDFLEKLSQT |
| 5457696 | 265 | RTIVKYKEE...WKRKVGEFLRANL |
| 14520481 | 265 | RTIVKYKEE...WKRKVGEFLRANL |
| 40744233 | 315 | ELYSLSHRQRMAHLPTARTYFADAIAPEGFYLVYMTIVRK |

| | | |
|---|---|---|
| 15613871 | | |
| RAAC00501 | | |
| 125974699 | | |
| 5457696 | | |
| 14520481 | | |
| 40744233 | 355 | QKTARMYLKLDL |

FIG 3A

```
RAAC00568      1  MGMIHEQTDFTTSEAIRPDTLISPPDDWAFLGRPSRFDVD
6686567
4586418        1         MLEDTSFAIQPE.QDDKTQETHRIDIGNMHTFS
89098051       1         MNDTSFAIHPG.KSRKIENSDYQEAGDVLAIE
114844717      1                                        MYQ

RAAC00568     41  HDGWATVQYDAGVMVGVAALDDTVLRVAYCRSPGEWPTST
6686567        1                MVGVAALDDTVLRVAYCRSPGEWPTST
4586418       33  HTEHVFSFHCDTGIVKIRFYREDIVRIAFN.PFGETSLST
89098051      32  ECRNGLKARTETGELRIVFYANEIVRITMN.FFGEADAGT
114844717      4  KTSEGIVVRNEGKKLELRVLGDKIINVFVS.DKEEKRKDT

RAAC00568     81  PAIVEQMSQRHSWRLVQEERRVQLECVAGWQIQINRDDGT
6686567       28  PAIVEQMSQRHSWRLVQEERRVQLECVAGWQIQINRDDGT
4586418       72  SVAVVKEPEKVDASVHETEEEVTLTSAKQTVVLQKRPFRV
89098051      71  SPAVIGGLQEVKLEHYESGDQAEVKTSCLTVKLTKSPLRI
114844717     43  IAIERKEYDIPEFSVRKELESILIETDSLKVKINKNDLSV

RAAC00568    121  WSIRHLGFGTAVEAITWYKRK.KGGALTFASLDNAR.FYG
6686567       68  WSIRHLGFGTAVEAITWYKRK.KGGALTFASLDNAR.FYG
4586418      112  RIYDNHGRLLVAEGKKGMAFTYQGEVCCFKMMDEADHFYG
89098051     111  TVADAEGRVLAGENQKGMGYKHSKEVICFKNMEESDQFYG
114844717     83  SFLDKNENIINEDYNGGVKFS.ETDVRCYKKLREDH.FYG

RAAC00568    159  LGEKPGPLDKRHEAYTMWNSDVYAPHVPEMEALYLSIPFF
6686567      106  LGEKPGPLDKRHEAYTMWNSDVYAPHVPEMEALYLSIPFF
4586418      152  FGEKTGFLDKRGETMTMWNTDVYAPHNPETDPLYQSHPYF
89098051     151  FGEKTGFLNKRGEKLVMWNSDVYAPHNPETDPLYQSIPFF
114844717    121  FGEKAGYLDKKGERLEMWNTDEFMTHNQTTKLLYESYPFF

RAAC00568    199  LRLQDQTAVGIFVDNPGRSRFDFRSRYPDVEIS.TERGGL
6686567      146  LRLQDQTAVGIFVDNPGRSRFDFRSRYPDVEIS.TERGGL
4586418      192  MTVRNGSAHGIFFDNTYKTTFDFQTATDEYCFS.AEGGAI
89098051     191  LTLREGQAHGIFFDNTFRAEFDMR.GDEFYSFS.ADGGQL
114844717    161  IGMNDYHTYGIFLDNSFRSFFDMGQECQEYYYFGAYGGQM

RAAC00568    238  DVYFIFGASLKDVIRRYTKLTGRMPMPPKWALGYHQSRYS
6686567      185  DVYFIFGASLKDVIRRYTKLTGRMPMPPKWALGYHQSRYS
4586418      231  DYYVFAGPTPKDVLEQYTDLTGRMPLPPKWALGYHQSRYS
89098051     229  DYYLMAGPSPKDVIRQYTSLTGRMPLPAKWAIGYHQSRYS
114844717    201  NYYFIYGEDIKEVVENYTYLTGRINLPPLWALGNQQSRYS

RAAC00568    278  YETQSEVLSVAQTFVERDIPVDALYLDIHYMDGYRVFTFD
6686567      225  YETQSEVLSVAQTFVERDIPVDALYLDIHYMDGYRVFTFD
4586418      271  YETEQEVREIAQTFIEKDIPLDVIYLDIHYMNGYRVFTFD
89098051     269  YESQQEVMELAAAFKEKGIPLDSIHLDIHYMDEYRVFTFD
114844717    241  YTPQERVLEIAKTFREKDIPCDVIYLDIDYMEGYRVFTWN
```

FIG 3B

| | | |
|---|---|---|
| RAAC00568 | 318 | ERRFPDPARMCDELRKLGVRVVPIVDPGVKQDPEYPVYMD |
| 6686567 | 265 | ERRFPDPARMCDELRKLGVRVVPIVDPGVKQDPEYPVYMD |
| 4586418 | 311 | RNRFPNLKQLIADLKQKGIRVVPIVDPGVKEDPEYVIYQE |
| 89098051 | 309 | RDKFPDPEKMISDLKEMGIHIVPIVDPGVKEDPEYMVYKQ |
| 114844717 | 281 | KDTFKNYKEMLKQLKEMGFKVVTIVDPGVKRDYDYHVYRE |
| | | |
| RAAC00568 | 358 | GLAHNHFCQTAEGQVYLGEVWPGLSAFPDFASEEVRAWWG |
| 6686567 | 305 | GLAHNHFCQTAEGQVYLGEVWPGLSAFPDFASEEVRAWWG |
| 4586418 | 351 | GIRHDYFCKYIEGNVYFGEVWPGKSAFPDFTNKKVRKWWG |
| 89098051 | 349 | GIQEDLFCKYLEGNVYYGDVWPGNSVFPDFTSKKVRDWWG |
| 114844717 | 321 | GIEEDYFVKDKYGITYVGKVWPGEACFPDFLQEEVRYWWG |
| | | |
| RAAC00568 | 398 | KWHRVYTQMGIEGIWNDMNEPAVFNE.TKTMDVNVVHRGD |
| 6686567 | 345 | KWHRVYTQMGIEGIWNDMNEPAVFNE.TKTMDVNVVHRGD |
| 4586418 | 391 | EKHQFYTDLGIEGIWNDMNEPSVFNE.TKTMDVKVIHDND |
| 89098051 | 389 | SLHSYYTELGIEGIWNDMNEPAVFNE.SKTMDLKVMHDND |
| 114844717 | 361 | EKHREFIKDGIDGIWNDMNEPAVFETPTKTMPEDNIHILD |
| | | |
| RAAC00568 | 437 | GRLYTHGEVHNLYGFWMAEATYRGLKAQLAGKRPFVLTRA |
| 6686567 | 384 | GRLYTHGEVHNLYGFWMAEATYRGLKAQLAGKRPFVLTRA |
| 4586418 | 430 | GDPKTHRELHNVYGFMMGEATYKGMKKLLNGKRPFLLTRA |
| 89098051 | 428 | GNPRTHKELHNLYGLLMGKSTYEGMKRNLKGKRPFLLTRA |
| 114844717 | 401 | GEKVLHKEAHNVYANYMAMATRDGLLRIRPNERPFVLTRA |
| | | |
| RAAC00568 | 477 | GYSGIQRYAAVWTGDNRSFWEHMAMAIPMVLNMGMSGIPL |
| 6686567 | 424 | GYSGIQRYAAVWTGDNRSFWEHMAMAIPMVLNMGMSGIPL |
| 4586418 | 470 | GFSGIQRYAAVWTGDNRSFWEHLQMSLPMCMNLGLSGVAF |
| 89098051 | 468 | GYSGVQRYAAVWTGDNRSFWEHLQMSLPMVMNLGVSGIPF |
| 114844717 | 441 | AFSGIQRYAAMWTGDNRSLYEHLLMMMPMLINIGLSGQPF |
| | | |
| RAAC00568 | 517 | GGPDVGGFAHHASGELLARWTQMGAFFPFFRNHSAMGTHR |
| 6686567 | 464 | GGPDVGGFAHHASGELLARWTQMGAFFPFFRNHSAMGTHR |
| 4586418 | 510 | CGPDVGGFAHNTNGELLTRWMQVGAFTPYFRNHCAIGFRR |
| 89098051 | 508 | SGPDVGGFAHDSNGELLARWTQAGAFTPFFRNHSVLGSAR |
| 114844717 | 481 | AGADVGGFEGDCHEELFIRWIEAATFTPFLRVHSAIGTKD |
| | | |
| RAAC00568 | 557 | QEPWAFGPTFEAVIRRAIRLRYRFLPYLYTLAREAHETGL |
| 6686567 | 504 | QEPWAFGPTFEAVIRRAIRLRYRFLPYLYTLAREAHETGL |
| 4586418 | 550 | QEPWAFGEKYERIIKKYIRLRYQWLPHLYTLFAEAHETGA |
| 89098051 | 548 | QEPWAFGEKYEAIIRKYIELRYTWMPHLYSLFAEAHKEGT |
| 114844717 | 521 | QEPWSFGKRCEDISRKYIKMRYEILPYLYDLFYIASQKGY |
| | | |
| RAAC00568 | 597 | PMMRPLVLEYPDDPNTHHVDDQFLVGSDLLVAPILKPGMA |
| 6686567 | 544 | PMMRPLVLEYPDDPNTHHVDDQFLVGSDLLVAPILKPGMA |
| 4586418 | 590 | PVMRPLFFEYPDDENTYNLYDEFLVGANVLIAPIMTPSTT |
| 89098051 | 588 | PVMRPLFLEFPEDEHTWNLSDQFMIGDNVIIAPIMQPGTF |
| 114844717 | 561 | PIMRPLVFEYQEDENTHKIYDEFLLGDNLLVAPIYLPSKE |

FIG 3C

```
RAAC00568   637  HRMVYLPDGEWIDYETRERYQGRQYILTYAPLDRIPLYVR
6686567     584  HRMVYLPDGEWIDYETRERYQGRQYILTYAPLDRIPLYVR
4586418     630  RRVAYFPKGNWVDYWTGEVLEGGQYHLISADLETLPIFIK
89098051    628  HRAVYLPEGMWTDYWTGSTYEGKKHHLIKAPLETLPIFIK
114844717   601  KREVYLPKGIWYDYWTGKEFKGESYYLVDAPIDIIPLFVK

RAAC00568   677  AGSAIPVNLLERSGET...QLGWEIFVDANGRASGRCYED
6686567     624  AGSAIPVNLLERSGET...QLGWEIFVDANGRASGRCYED
4586418     670  QGSAIALGDVKRSTEMPDEHRTVHIYKANGGKATYVLYDD
89098051    668  KGTMAAHGEAGAAGPL.....TLHLYYEEGSECSYTLYED
114844717   641  EGGILLKREPQSFVEE.KEIKEIIVEIYRGEEGHYLHYED

RAAC00568   714  DGETFSYEDGAYCDRVLQALATSEGTLIECHLVQGSGDGG
6686567     661  DGETFSYEDGAYCDRVLQALATSEGTLIECHLVQGSGDGG
4586418     710  DGQTFSYEKGDYLRMYIEVEYG.ENSVHIVTKSEGTYQPS
89098051    703  DGETFAYEEGEYREICFKVKCE.EGTVYLNSAIAGTYEPV
114844717   680  DGKSFDYTKGVYNLFDISFCYKEGRMDIKFDKIHFGYDKG

RAAC00568   754  SLESVVRVFTPDDVREARAQGISFSIHV
6686567     701  SLESVVRVFTPDDVREARAQGISFSIHV
4586418     749  WKLSFAIHHATEQTKVTIDGNEQNAIFDPHQRILLIQSE
89098051    742  WSTVQLAVHSRENVRLKIGSSTLLPEKIEEGRHYFILS
114844717   720  VKKYKFIFKNFGDIKEIKINGEKVGKENCEIEL
```

FIG 4A

| | | |
|---|---|---|
| 16422318 | 1 | MKISDGNWLIQPGLNLIHPVQVFDVEQHGNEMVIYAAPRD |
| 16504867 | 1 | MKISDGNWLIQPGLNLIHPVQVFDVEQHGNEMVVYAAPRD |
| 16131527 | 1 | MKISDGNWLIQPGLNLIHPLQVFEVEQQDNEMVVYAAPRD |
| 52081844 | 1 | MKFSDGYWLTREGYHINTPKEAYDRMIDQQSLTVYGPVKA |
| 52787233 | 1 | MKFSDGYWLTREGYHINTPKEAYDRMIDQQSLTVYGPVKA |
| RAAC00594 | 1 | MKFTDGNWLVREGVSIHPGLAVQEWRQEGDGVLFFVACRP |

| | | |
|---|---|---|
| 16422318 | 41 | VRERTWQLDTPLFTLRFFSPQEGVIGVRMEHFQGALDNGP |
| 16504867 | 41 | VRERTWQLDTPLFTLRFFSPQEGVIGVRMEHFQGALDNGP |
| 16131527 | 41 | VRERTWQLDTPLFTLRFFSPQEGIVGVRIEHFQGALNNGP |
| 52081844 | 41 | VQKRGDTLDTRMLTVRFSSPLEDMIRVQVFHFQGETPRKP |
| 52787233 | 41 | VQKRGDTLDTRMLTVRFSSPLEDMIRVQVFHFQGETPRKP |
| RAAC00594 | 41 | VAHRGHMLDGPMLTCRISFPRPGMVRVEQHHFFGRMPRGP |

| | | |
|---|---|---|
| 16422318 | 81 | HYPLNVLQDINVEMQNNAEFAELKSGSLSVRVTKGEIWSL |
| 16504867 | 81 | HYPLNVLQDINVEMQNNAEFAELKSGSLSVRVTKGELWSL |
| 16131527 | 81 | HYPLNILQDVKVTIENTERYAEFKSGNLSARVSKGEFWSL |
| 52081844 | 81 | DFQL.HTADVEPVITEHDDALTFQSGSLCVEVSK.NGWGY |
| 52787233 | 81 | DFQL.HTADVEPVITEHDDALTFQSGSLCVEVSK.NGWGY |
| RAAC00594 | 81 | HFPL.ELKPQPFDAAETEDGVVLRAGEMEVRVRL.SPWSI |

| | | |
|---|---|---|
| 16422318 | 121 | DFLRNGVRITGSQLKNNGYVQDTNSGRNYMFERLDLGVGD |
| 16504867 | 121 | DFLRNGVRITGSQLKNNGYVQDTNSGRNYMFERLDLGVGE |
| 16131527 | 121 | DFLRNGERITGSQVKNNGYVQDTNNQRNYMFERLDLGVGE |
| 52081844 | 119 | QFSRDGQSLTASESNSLAYITS.DDGRTFMREQLNIGVGE |
| 52787233 | 119 | QFSRDGQSLTASESNSLAYITS.DDGRTFMREQLNIGVGE |
| RAAC00594 | 119 | AFYENGRFLTESGPRSTAYVV..DHGRPHMRGQLHLSVGE |

| | | |
|---|---|---|
| 16422318 | 161 | TVYGLGERFTALVRNGQTVETWNRDGGTSTEQSYKNIPFY |
| 16504867 | 161 | TVYGLGERFTALVRNGQTVETWNRDGGTSTEQSYKNIPFY |
| 16131527 | 161 | TVYGLGERFTALVRNGQTVETWNRDGGTSTEQAYKNIPFY |
| 52081844 | 158 | LLYGLGERFTAFVKNGQTVDIWNQDGGTSTEQAYKNVPFY |
| 52787233 | 158 | LLYGLGERFTAFVKNGQTVDIWNQDGGTSTEQAYKNVPFY |
| RAAC00594 | 157 | NVYGLGERFTAFVKNGQSLDIWNRDGGTGSDQAYKNVPFY |

| | | |
|---|---|---|
| 16422318 | 201 | ITNRGYGVLVNHPQCVSFEIGSEKVSKVQFSVESEYLEYF |
| 16504867 | 201 | ITNRGYGVLVNHPQCVSFEIGSEKVSKVQFSVESEYLEYF |
| 16131527 | 201 | MTNRGYGVLVNHPQCVSFEVGSEKVSKVQFSVESEYLEYF |
| 52081844 | 198 | LSNKGYGVFVNHPELVSYEIGSEVVSKAQFSVEGESLDYF |
| 52787233 | 198 | LSNKGYGVFVNHPELVSYEIGSEVVSKAQFSVEGESLDYF |
| RAAC00594 | 197 | LTNRGYGVFVNHPERVWFEIGTEFVSKVQFSVEGEALDYV |

| | | |
|---|---|---|
| 16422318 | 241 | VIDGPTPKDVLNRYTQFTGRPALPPAWSFGLWLTTSFTTN |
| 16504867 | 241 | VIDGPTPKDVLNRYTQFTGRPALPPAWSFGLWLTTSFTTN |
| 16131527 | 241 | VIDGPTPKAVLDRYTRFTGRPALPPAWSFGLWLTTSFTTN |
| 52081844 | 238 | VISGAEPKDVLKRYAALTGKPALPPAWSFGLWLSTSFTTD |
| 52787233 | 238 | VISGAEPKDVLKRYAALTGKPALPPAWSFGLWLSTSFTTD |
| RAAC00594 | 237 | VIGGCHPKGVIERYTALTGRPALPPMWSFGLWLSTSFTTD |

FIG 4B

| | | |
|---|---|---|
| 16422318 | 281 | YDEATVNSFIDGMAERNLPLHVFHFDCFWMKAFQWCDFEW |
| 16504867 | 281 | YDEATVNRFIDGMAERNLPLHVFHFDCFWMKAFQWCDFEW |
| 16131527 | 281 | YDEATVNSFIDGMAERNLPLHVFHFDCFWMKAFQWCDFEW |
| 52081844 | 278 | YSEETVTRFIDGMTERGIPLSVFHFDCFWMKEFEWCNFEW |
| 52787233 | 278 | YSEETVTRFIDGMTERGIPLSVFHFDCFWMKEFEWCNFEW |
| RAAC00594 | 277 | YDEETVSQFVDGMASRGIPLSVFHFDCFWMKPFEWCNFAW |
| 16422318 | 321 | DPVTFPDPKGMIRRLKAKGLKVCVWINPYIGQKSPVFQEL |
| 16504867 | 321 | DPVTFPDPKGMIHRLKAKGLKVCVWINPYIGQKSPVFQEL |
| 16131527 | 321 | DPLTFPDPEGMIRRLKAKGLKICVWINPYIGQKSPVFKEL |
| 52081844 | 318 | DERYFKQPEAMLSRLKEKGLKICVWINPYIAQKSKLFQEG |
| 52787233 | 318 | DERYFKQPEAMLSRLKEKGLKICVWINPYIAQKSKLFQEG |
| RAAC00594 | 317 | DTACFPDPAGMLARLKSRGLRICVWINPYIAQKSPLFREA |
| 16422318 | 361 | KEKGYLLKRPDGSLWQWDKWQPGLAIYDFTNPQACEWYAD |
| 16504867 | 361 | KEKGYLLKRPDGSLWQWDKWQPGLAIYDFTNPQACEWYAD |
| 16131527 | 361 | QEKGYLLKRPDGSLWQWDKWQPGLAIYDFTNPDACKWYAD |
| 52081844 | 358 | KENGYFLKNSRGDVWQWDRWQAGMAIVDFTNEKARDWYCS |
| 52787233 | 358 | KENGYFLKNSRGDVWQWDRWQAGMAIVDFTNEKARDWYCS |
| RAAC00594 | 357 | MERGYLLKRPNGDVWQWDLWQPGMGIVDFTNPDARRWYQS |
| 16422318 | 401 | KLKGLVEMGVDCFKTDFGERIPTDVQWFDGSDPQKMHNHY |
| 16504867 | 401 | KLKGLVEMGVDCFKTDFGERIPTDVQWFDGSDPQKMHNHY |
| 16131527 | 401 | KLKGLVAMGVDCFKTDFGERIPTDVQWFDGSDPQKMHNHY |
| 52081844 | 398 | KLESLLDMGVDCFKTDFGERIPSDAVYFDGSDPERMHNYY |
| 52787233 | 398 | KLESLLDMGVDCFKTDFGERIPSDAVYFDGSDPERMHNYY |
| RAAC00594 | 397 | HLRRLLDMGVDAFKTDFGERIPTDVVYHDGSDPQKMHNFY |
| 16422318 | 441 | AYIYNELVWNVLKETVGVEEAVLFARSASVGAQQFPVHWG |
| 16504867 | 441 | AYIYNELVWNVLKETVGVEEAVLFARSASVGAQQFPVHWG |
| 16131527 | 441 | AYIYNELVWNVLKDTVGEEEAVLFARSASVGAQKFPVHWG |
| 52081844 | 438 | SYLYNKTVFDLLRQKRGEREAVVFARSATAGGQQFPVHWG |
| 52787233 | 438 | SYLYNKTVFDLLRQKRGEREAVVFARSATAGGQQFPVHWG |
| RAAC00594 | 437 | SYLYNEAVWEVLRE.RGGGEALVFARSATAGGQRFPVHWG |
| 16422318 | 481 | GDCYANYESMAESLRGGLSIGLSGFGFWSHDIGGFENTAP |
| 16504867 | 481 | GDCYANYESMAESLRGGLSIGLSGFGFWSHDIGGFENTAP |
| 16131527 | 481 | GDCYANYESMAESLRGGLSIGLSGFGFWSHDIGGFENTAP |
| 52081844 | 478 | GDCFASYDSMAESLRGGLSLSLSGFGFWSHDIGGFESTAT |
| 52787233 | 478 | GDCFASYDSMAESLRGGLSLSLSGFGFWSHDIGGFESTAT |
| RAAC00594 | 476 | GDCRATYESMAETLRGGLSLALSGFGFWSHDIGGFEDTAP |
| 16422318 | 521 | AHVYKRWCAFGLLSSHSRLHGSKSYRVPWAYDDESCDVVR |
| 16504867 | 521 | AHVYKRWCAFGLLSSHSRLHGSKSYRVPWAYDDESCDVVR |
| 16131527 | 521 | AHVYKRWCAFGLLSSHSRLHGSKSYRVPWAYDDESCDVVR |
| 52081844 | 518 | ADLYKRWTAFGLLSTHSRLHGSESYRVPWLFDEEAADVMR |
| 52787233 | 518 | ADLYKRWTAFGLLSTHSRLHGSESYRVPWLFDEEAADVMR |
| RAAC00594 | 516 | AHLYKRWIAFGLFSSHSRLHGSGSYRVPWLFDEESVDVLR |

FIG 4C

| | | |
|---|---|---|
| 16422318 | 561 | FFTEQKCRMMPYLYREAARANEAGTPMMRAMMLEFPDDPA |
| 16504867 | 561 | FFTEQKCRMMPYLYREAARANEAGTPMMRAMMLEFPDDPA |
| 16131527 | 561 | FFTQLKCRMMPYLYREAARANARGTPMMRAMMMEFPDDPA |
| 52081844 | 558 | YFVKLKHRLMPYLYAAAHEAHAEGIPMMRAMLLEFPGDNT |
| 52787233 | 558 | YFVKLKHRLMPYLYAAAHEAHAEGIPMMRAMLLEFPGDNT |
| RAAC00594 | 556 | HFTRWKLRLMPYLWSCAVEAHRTGVPMLRPMMLEFPDDPT |

| | | |
|---|---|---|
| 16422318 | 601 | CDYLDRQYMLGDAVMVAPVFSEAGDVEFYLPEGRWTHLWR |
| 16504867 | 601 | CDYLDRQYMLGDAVMVAPVFSEAGDVEFYLPEGRWTHLWR |
| 16131527 | 601 | CDYLDRQYMLGDNVMVAPVFTEAGDVQFYLPEGRWTHLWH |
| 52081844 | 598 | CHWLDRQYMLGGRLLVAPVFQEDGAVRYYLPKGTWTHLLT |
| 52787233 | 598 | CHWLDRQYMLGGRLLVAPVFQEDGAVRYYLPKGTWTHLLT |
| RAAC00594 | 596 | CDTLDRQYMLGPSLLVAPVFSETGEVVYYLPEGRWTHLFT |

| | | |
|---|---|---|
| 16422318 | 641 | NDEVQGSRWHKQQHDFLSLPVYVRDNTLLALGNNSQKPDY |
| 16504867 | 641 | NDEVQGSRWHKQQHDFLSLPVYVRDNTLLALGNNSQKPDY |
| 16131527 | 641 | NDELDGSRWHKQQHGFLSLPVYVRDNTLLALGNNDQRPDY |
| 52081844 | 638 | GKETEGGEWKEERYGYMRLPLFVRENTLLPLGQESGRPDY |
| 52787233 | 638 | GKETEGGEWKEERYGYMRLPLFVRENTLLPLGQESGRPDY |
| RAAC00594 | 636 | GETRQGGRWYRERYDFMSLPVFVREGSILAMGAETDRPNQ |

| | | |
|---|---|---|
| 16422318 | 681 | AWHEGTAFQLFHLDDGCEAVCEVPATDGSTIFTLQAKRTG |
| 16504867 | 681 | AWHEGTAFQLFHLDDGCEAVCEVPATDGSTIFTLQAKRTG |
| 16131527 | 681 | VWHEGTAFHLFNLQDGHEAVCEVPAADGSVIFTLKAARTG |
| 52081844 | 678 | DYLDDVTFCLYHLKDGCTAEQTIYNEKG.EAMTLRASRHQ |
| 52787233 | 678 | DYLDDVTFCLYHLKDGCTAEQTIYNEKG.EAMTLRASRHQ |
| RAAC00594 | 676 | PYHREVAIHVYPIRPDHRSACTLFDEQGNELGTWHAFWDG |

| | | |
|---|---|---|
| 16422318 | 721 | NTITVSGEGKARNWTLCLRNITQISGTKC..GSYAGSELG |
| 16504867 | 721 | NTITVSGEGEARNWTLCLRNITQISGTKC..GSYAGSELG |
| 16131527 | 721 | NTITVTGAGEAKNWTLCLRNVVKVNGLQD..GSQAESEQG |
| 52081844 | 717 | NTIAVKTTGVQKNWKLLLRGLSVTSVING...AAEALQEG |
| 52787233 | 717 | NTIAVKTTGVQKNWKLLLRGLSVTSVING...AAEALQEG |
| RAAC00594 | 716 | DHLVLTAQGRSEAWSAVLHGIDDPAKLAAQGAECRVSPEG |

| | | |
|---|---|---|
| 16422318 | 759 | VVVTPQGNEVVITL |
| 16504867 | 759 | VVVTPQGNEVVITL |
| 16131527 | 759 | LVVKPQGNALTITL |
| 52081844 | 754 | TAVQPKEKERDVFIYF |
| 52787233 | 754 | TAVQPKEKERDVFIYF |
| RAAC00594 | 756 | VVISPHHPQEAVRVAGCREQWRAE |

FIG 5A

| | | |
|---|---|---|
| 16079924 | 1 | MKKARMIVDKEYKIGEVDKRIYGSFIEHMGRAVYEG |
| RAAC00602 | 1 | MSNLKARMTIDPAYRLAETDPRIYGSFIEHLGRAVYGG |
| 89095985 | 1 | MTLNAHKAKMLIDKSFRISDIDPRIYGSFIEQLGRAVYGG |
| 15614424 | 1 | MTLTATMVVDKSFKIGEIDKRIYGSFIEHLGRAVYEG |
| 52081375 | 1 | MTVHKAKMTIDKEYKVAEIDKRIYGSFIEHLGRAVYEG |
| 52786751 | 1 | MTVHKAKMTIDKEYKVAEIDKRIYGSFIEHLGRAVYEG |

| | | |
|---|---|---|
| 16079924 | 37 | IYEPDHPEADEDGFRKDVQSLIKELQVPIIRYPGGNFLSG |
| RAAC00602 | 39 | IYDPSHPTADEDGFRQDVIDLVKELNVPIVRYPGGNFVSG |
| 89095985 | 41 | IYELSHSSADEDGFRQDVIELVKELRVPIIRYPGGNMVSA |
| 15614424 | 38 | IYEPGHPDGDEQGFRKDVIRLVQELQVPLVRYPGGNFVSG |
| 52081375 | 39 | IYEPDHPEADESGFRKDVIKLVRELKVPFIRYPGGNFVSG |
| 52786751 | 39 | IYEPDHPEADESGFRKDVIKLVRELKVPFIRYPGGNFVSG |

| | | |
|---|---|---|
| 16079924 | 77 | YNWEDGVGPVENRPRRLDLAWQTTETNEVGTNEFLSWPKK |
| RAAC00602 | 79 | YRWEDGVGPVEQRPVQLDLAWRSLEPNRVGLNEFARWAKK |
| 89095985 | 81 | YNWEDGIGPKELRPKRLDLAWNSLETNEVGTNEFAAWAKK |
| 15614424 | 78 | YNWEDGVGPVSERPKRLDLAWRTTETNEIGTNEFVDWAKK |
| 52081375 | 79 | YNWEDGVGPVEQRPTRLDLAWATTEPNLIGTNEFMDWAKL |
| 52786751 | 79 | YNWEDGVGPVEQRPTRLDLAWATTEPNLIGTNEFMDWAKL |

| | | |
|---|---|---|
| 16079924 | 117 | VNTEVNMAVNLGTRGIDAARNLVEYCNHPKGSYWSDLRRS |
| RAAC00602 | 119 | ANSQVMMAVNLGTRGIEEAKQIVEYCNHPGGSYWSDLRRK |
| 89095985 | 121 | VNAEVMMAVNLGTRGIDAARNLVEYCNHPGGTYWSDLRKE |
| 15614424 | 118 | VGAEVNMAVNLGSRGVDAARNLVEYCNHPSGSYWSDLRIS |
| 52081375 | 119 | VGAEVNMAVNLGTRGIDAARNLVEYCNHPSGSYYSDLRKS |
| 52786751 | 119 | VGAEVNMAVNLGTRGIDAARNLVEYCNHPSGSYYSDLRKS |

| | | |
|---|---|---|
| 16079924 | 157 | HGYEQPYGIKTWCLGNEMDGPWQIGHKTADEYGRLAAETA |
| RAAC00602 | 159 | HGIEQPHGIRVWCLGNEMDGPWQIGHKTADEYGRLAQEAA |
| 89095985 | 161 | HGYTDPHNIKVWCLGNEMDGPWQIGMKTAYEYGRLAAETA |
| 15614424 | 158 | HGYKDPHNIKTWCLGNEMDGPWQIGQKTAEEYGRVAAEAG |
| 52081375 | 159 | HGYKEPHKIKTWCLGNEMDGPWQIGHKTAAEYGRLAAEAA |
| 52786751 | 159 | HGYKEPHKIKTWCLGNEMDGPWQIGHKTAAEYGRLAAEAA |

| | | |
|---|---|---|
| 16079924 | 197 | KVMKWVDPSIELVACGSSNSGMPTFIDWEAKVLEHTYEHV |
| RAAC00602 | 199 | KVMKWVDPSIELVACGSSGSKMATFPDWERIVLEHAYDEV |
| 89095985 | 201 | KAMKLVDPSIELVSCGSSGSGMPTFPEWEAETLEHTYEAA |
| 15614424 | 198 | KVMKLVDPSIELVACGSSNSKMATFADWEATVLDHTYDYV |
| 52081375 | 199 | KVMKWTDPSIELVACGSSGSGMPTFIDWETTVLDHTYEHV |
| 52786751 | 199 | KVMKWTDPSIELVACGSSGSGMPTFIDWETTVLDHTYEHV |

| | | |
|---|---|---|
| 16079924 | 237 | DYISLHTYYGNRDNNLPNYLARSMDLDHFIKSVAATCDYV |
| RAAC00602 | 239 | DYLSLHTYYGNRDGDLANFLACSLDMDAFIRAVVATCDFV |
| 89095985 | 241 | DYISLHQYYGNRDNDSANYLASTLDMDSFIKTVTAACDYM |
| 15614424 | 238 | DYISLHTYYGNRDDDLANYLAQSMDMDEFIRSVIAIADYV |
| 52081375 | 239 | EYISLHSYYGNRDNDLPNYLARSLDMDHFIKTVISVCDYM |
| 52786751 | 239 | EYISLHSYYGNRDNDLPNYLARSLDMDHFIKTVISVCDYM |

FIG 5B

| | | |
|---|---|---|
| 16079924 | 277 | KAKTRSKKTINLSLDEWNVWYHSNEADKKVEPWITARPIL |
| RAAC00602 | 279 | RAKKRSNKTIYLSFDEWNVWFHSNEADKQVEPWQVGPPLL |
| 89095985 | 281 | KAKKRSKKTMNLSFDEWNVWFHSNDQDKAIEPWSLSPPLL |
| 15614424 | 278 | KAKKRSKKTIHLSFDEWNVWFHSNEADRQITPWSVAPPLL |
| 52081375 | 279 | KAKKKSKKTIHLSYDEWNVWYHSNEKDKEAERWAKAPHLL |
| 52786751 | 279 | KAKKKSKKTIHLSYDEWNVWYHSNEKDKEAERWAKAPHLL |
| | | |
| 16079924 | 317 | EDIYNFEDALLVGSLLITMLQHADRVKIACLAQLVNVIAP |
| RAAC00602 | 319 | EDVYTMEDALVVGCMLITLLKHADRVRIACLAQLVNVIAP |
| 89095985 | 321 | EDIYTFEDALLVGSMLNTLLKHSDRVKIACMAQLVNVIAP |
| 15614424 | 318 | EDIYTFEDALLVGSMLITLLKHADRVKIACLAQLVNVIAP |
| 52081375 | 319 | EDIYNFEDALLVGCMLITMLKHADRVKIACLAQLVNVIAP |
| 52786751 | 319 | EDIYNFEDALLVGCMLITMLKHADRVKIACLAQLVNVIAP |
| | | |
| 16079924 | 357 | IMTEKGGEAWRQPIFYPYMHASVYGRGESLKPLISSPKYD |
| RAAC00602 | 359 | IMTENGGPSWRQTIFYPFAHASNLAHGVVLYAPVESPKYD |
| 89095985 | 361 | IMTETGGGIWKQSIFYPFYYTSVYGRGTALHSIVDSPKYD |
| 15614424 | 358 | IMTEKGGPAWKQTIFYPYMHASVYGRGVALQAQISSPKYD |
| 52081375 | 359 | IMTDKGGEAWRQTIFYPFMHASVYGRGTVLQTAVSSPKYD |
| 52786751 | 359 | IMTDKGGEAWRQTIFYPFMHASVYGRGTVLQTAVSSPKYD |
| | | |
| 16079924 | 397 | CSDFTDVPYVDAAVVYSEEEETLTIFAVNKAEDQ.METEI |
| RAAC00602 | 399 | SKDFTDVPYLEAVPVWNEAAGEMVLLAVNRAEEP.LALDV |
| 89095985 | 401 | SKDFTDVPFLDQSVVYNEESEELVIFAVNRSLDTQLLVDV |
| 15614424 | 398 | SKDFTDVPYLDAAVVHLEEAEEVTIFAVNKHQTESLNLQC |
| 52081375 | 399 | AKDFTDVPYLESVSVFNEEAEELTVFAVNRATDAGLEMEA |
| 52786751 | 399 | AKDFTDVPYLESVSVFNEEAEELTVFAVNRATDAGLEMEA |
| | | |
| 16079924 | 436 | SLRGFESYQIAEHIVLEHQDIKATNQHNRKN.VVPHSNGS |
| RAAC00602 | 438 | DLRGFPNARSEEHIVLTHPNMKAVNTKERPNEVVPQKRSI |
| 89095985 | 441 | DIRSFEGYKLAEQIVLKNENPKAVNSINDEQ.VKPEKGND |
| 15614424 | 438 | DMRSFEGYHVLEHIVLEHENMKATNQ.GREQ.VTPHHNGD |
| 52081375 | 439 | DMRSFEGYSVSEHIVLEHEDHKATNEKDRNN.VVPHSGGD |
| 52786751 | 439 | DMRSFEGYSVSEHIVLEHEDHKATNEKDRNN.VVPHSGGD |
| | | |
| 16079924 | 475 | SSVSENGLTAHFTPLSWNVIRLKKQS |
| RAAC00602 | 478 | GAVDAGRLAVELPALSWNVIRIRV |
| 89095985 | 480 | SYIENGTLTAVLPKMSWNMFRLKKLEV |
| 15614424 | 476 | SAIDQGRLTANLAKLSWNVIRLGKK |
| 52081375 | 478 | AKVCDGRLTAHLPKLSWNVIRMKKQ |
| 52786751 | 478 | AKVCDGRLTAHLPKLSWNVIRMKKQ |

FIG 6A

```
15893601     1                              MHRKFLTALIALG.
15893600     1          MYSLFLWASVKIFTMESRGRYVVHKRILSTVVAFG.
15896196     1 MKKLFTNLLLLCSIVFLGALLNGHNVQASDSFTYPSAYGW
116513351    1                        MKKKNLLMTTLATLSASG.
RAAC00798    1                                       MPGAG.
```

```
15893601    14 ........................................
15893600    36 ........................................
15896196    41 WSVDNGYDVNNVNSRMVSGDFNGDGKADVATFYDYGNGAS
116513351   19 ........................................
RAAC00798    6 ........................................
```

```
15893601    14 ...ITVSCSGNIVFASP...........LQDQYNQSQQQY
15893600    36 ...IVASMGSTSVFAAP...........LQD....AQSKY
15896196    81 RIHVFTSNGSSFDYASAYGWWNTPSGYDPKRITAVVAGDF
116513351   19 ...ALLTTGASALADSY...............TVVKNDTL
RAAC00798    6 .......IGRDRRMGSG................INCDGCF
```

```
15893601    40 QNALKSVQDIENKIEALDNQIGELNNS.....INDTDKRI
15893600    58 DASHKNVQNLEEDIQKMDNQIETIMSQ.....RDSVDKKI
15896196   121 NGDHKDDIAVIYNYGNSETRIHVFISTGSSFSYTDCNGWW
116513351   41 WGLSKKYGVSVSDLKKANGVSGHLIYVG........QKLQ
RAAC00798   23 FSGFIYIKESPRPPRNRN......................
```

```
15893601    75 NESKQNMAITQGKID.....QAKQNITNQQEIYG..ERLR
15893600    93 TQSQQNINQAQNDIA.....VSKENIREEKDKFA..DRVR
15896196   161 NATGYDAGRITGAVAGDFNGDGKSDIATMYDYGGGETRIH
116513351   73 IPTKSTKATKTAKTS.....TSTSTVDTTSTTHTVVKGDT
RAAC00798   41 LSKTFDFERMESMRR.....PSAWMFTTLTLSFAALGHAT
```

```
15893601   108 AMYVNG...TTAQYIGV.................ILESQS
15893600   126 ALYISG...STQSYVDI.................LLKSKS
15896196   201 VFTSTG...SSFTYTGANGWWNSTGYDSNRVKGRVVAGDF
116513351  108 LWSLAK...KYGVSVSA.................LMKANN
RAAC00798   76 VLAATEQQPATYTVR.........................
```

```
15893601   128 FSDLISRLDAVKDVINYDKGIINNFKT.............
15893600   146 FSDMISRIDAIKQISDYDQKLVSNLKD.............
15896196   238 NGDGKTDIAAMYDYGGSESRIHVFLSTGDSFKYTGANGWW
116513351  128 LSSSTILIGQSLNLRAGMTTYGVNGVT.............
RAAC00798   91 QGDTLYRIAEADHLPLTALELANPQLS.............
```

```
15893601   155 QKQEVENQQKILADQNSKLVALQNENHKKLDDLNNKKNTQ
15893600   173 SQGRIEAKKDKIVSEKQQLEALNKENDTKLKQLNDEKSKQ
15896196   278 STTGYDANKVTGRLVAGDFNGDGKADIAAMYDYGNAETRI
116513351  155 TGSSSTAASANTASSSTSTTASSQAPKDKKTATKAKSTTTN
RAAC00798  118 .....NPNEIAAGQKVALPTAYTVQPGDTVYLIAKAHHLT
```

FIG 6B

| | | |
|---|---|---|
| 15893601 | 195 | NSLIVAAKDEEAKHTNEMQQIQKAMDDEKKK..IEALN.V |
| 15893600 | 213 | NVLIAQAKADESKNAAEVKAEKDAEKAAAQARLVAAANTA |
| 15896196 | 318 | HVLTSNGDSFTYTGANGWWNTTGYDANRVTGRVVAGDFNG |
| 116513351 | 195 | TSSNSNTSTSANTQSQSTASNSSASTTTNTNTVASNANTT |
| RAAC00798 | 153 | ISAILQANPGIHPLDLIVGQTLYLPIPASNSTASAPPNTS |

| | | |
|---|---|---|
| 15893601 | 232 | STNIQLKPVSKTTS...QNTTIQSSSTN.....GLAVVKY |
| 15893600 | 253 | ASSAPAKAVAKAQAPIPRGVSHSSFAGS.....GNDVVSF |
| 15896196 | 358 | DHKADIAAFYDYGSSASRIHVFTSNADSPESSKGAELVAY |
| 116513351 | 235 | SSTNTAASSSQAVSQAPTASTATTTASAS....ASAITSY |
| RAAC00798 | 193 | GTAASAGQPTSTQTQVSRAQLR...........QEILTY |

| | | |
|---|---|---|
| 15893601 | 264 | AETFLNTPYVWGGNKPG.GFDCSGLVQYVYAHFGINLPRT |
| 15893600 | 288 | AESFSGLPYIWGAEDPSRGFDCSGLVQYVYGHFGVSLGRT |
| 15896196 | 398 | AESFLGVPYVWGGADPS.GFDCSGLVQYCYEHFGVDLPRT |
| 116513351 | 271 | ALTFLGVPYVWGGTTPS.GFDCSGLVQYVYSHFGINLGRT |
| RAAC00798 | 221 | AKSFLGTPYCWGGDSPKTGFDCSGFVEYVFGHFGIQLPRE |

| | | |
|---|---|---|
| 15893601 | 303 | TYEQVNQGNPVTGNNLQPGDLLFFEPGSN.......GPEH |
| 15893600 | 328 | TYEQVNQGTTVT..ALQPGDLLFFGPAS........APYH |
| 15896196 | 437 | TYDQVNCGTTVT.DDLQPGDLLFFGSAT........SPTH |
| 116513351 | 310 | TYTQQYAGTKISVASAQAGDLYFWGSYG........SAYH |
| RAAC00798 | 261 | SHDQATVGTPVSPSNLQPGDLLFFTDTDSYASLYPNHVTH |

| | | |
|---|---|---|
| 15893601 | 336 | VGIYVGDGNFIEAP..HTGANVRFSP........LRSYCA |
| 15893600 | 358 | VAIYAGNNEMVEAP..RTGENVRKTA........VRGYSI |
| 15896196 | 468 | VAIYAGNSKMVEAP..HTGANVRLVD........IRSYFI |
| 116513351 | 342 | VAIALGGGQYVMAP..APGQNVMTGS........VSSYTP |
| RAAC00798 | 301 | VGIYTGNGAMIESSSAHNGEGVVIVQNVFQNPYYVSHFYG |

| | | |
|---|---|---|
| 15893601 | 366 | ARRIVN |
| 15893600 | 388 | AKRVR |
| 15896196 | 498 | AKRIFN |
| 116513351 | 372 | SFAVRVLG |
| RAAC00798 | 341 | ARDVIGP |

FIG 7A

| | | |
|---|---|---|
| 52081816 | 1 | MKDCLMINPQDNVGIALRELQTGETV |
| 52787203 | 1 | MKDCLMINPQDNVGIALRELQTGETV |
| 15893984 | 1 | MKNVIKINEKDNVVVALNDLNKGDVI |
| 121533397 | 1 | MALLKLHERDNVAVALRDIRQGETL |
| 15613053 | 1 | MNEKFAYIHEKDNVIIALSPLEQGEVL |
| RAAC01076 | 1 | MHEVNRRQRRRFRVAPKVLHLSPVDDVVVALEPLDVGEVV |

| | | |
|---|---|---|
| 52081816 | 27 | TVGERTIVIKEPILKGHKFALKDIAENENVIKYGFPIGHA |
| 52787203 | 27 | TVGERTIVIKEPILKGHKFALKDIAENENVIKYGFPIGHA |
| 15893984 | 27 | EIDGKVITAEEPVKKGHKIAITDIQKNSNIYKYGFPIGHA |
| 121533397 | 26 | AADNATVTAREDIPKGHKIALCDLQPGEHVIKYGFPIGHA |
| 15613053 | 28 | NVNGLPITLSESIPRGHKVAIVTIEQGEDVIKYGFPIGKA |
| RAAC01076 | 41 | ETPFGQVSARAPIALGHKLAVKPVKCGEAVHKYGFPIGVA |

| | | |
|---|---|---|
| 52081816 | 67 | TEMIQTGEWVHTKNVKTNLGGVEEYSYKPKFTENRYQKEP |
| 52787203 | 67 | TEMIQTGEWVHTKNVKTNLGGVEEYSYKPKFTENRYQKEP |
| 15893984 | 67 | LEEIKKGQWVHTNIKTNLDGIKDYEYNKQTFENPFKNEN |
| 121533397 | 66 | TSSVAAGQWLHSNVRTNLGEILAYEYKPEPPAVSPVPCR |
| 15613053 | 68 | TTTIQPGAWVHSQNMKTKLEGVQEYDYTPSTPSFRKQVEK |
| RAAC01076 | 81 | TQDIEPGEWVHTHNLRTALSERGSYVYRPHGSPALVLDDG |

| | | |
|---|---|---|
| 52081816 | 107 | L.TFKGFKRKDGKTGIRNELWIVPTVGCVNGIAELIIKEF |
| 52787203 | 107 | L.TFKGFKRKDGKTGIRNELWIVPTVGCVNGIAELIIKEF |
| 15893984 | 107 | L.TFKGYRREDGTVGIRNELWIVPTVGCVNGTADLIAERF |
| 121533397 | 106 | H.TFRGYRRPDGRVGVRNEIWIIPTVSCVNRTAQLLAERG |
| 15613053 | 108 | VRTFQGYVRDNGNVGIRNEIWIINTVGCINKTAERLAAIS |
| RAAC01076 | 121 | L.TFMGYVRSDGQVGVRNEIWILNTVGCVNKVAERLAAMA |

| | | |
|---|---|---|
| 52081816 | 146 | KAEVGSIAPFESVHVLKHQYGCSQLGDDHINTRTILANAV |
| 52787203 | 146 | KAEVGSIAPFESVHVLKHQYGCSQLGDDHINTRTILANAV |
| 15893984 | 146 | KSET....EFKDVHVFKHNFGCSQLGDDHNNTRTILGNIV |
| 121533397 | 145 | SALARNMANIDGVFAFTHPYGCSQLGDDHRATQTILADLV |
| 15613053 | 148 | NETCG..AGVDGVYHYPHLFGCSQLGDDLLYTQKILRNLV |
| RAAC01076 | 160 | DAKWRG.GGIDGVYHFAHPYGCSQLGDDLVYTQSLLAGLV |

| | | |
|---|---|---|
| 52081816 | 186 | NHPNAGGVLVLGLGCENNSIHEFREALGDYDHSRVKFLLS |
| 52787203 | 186 | NHPNAGGVLVLGLGCENNSIHEFREALGDYDHSRVKFLLS |
| 15893984 | 182 | KHPNAGGVLVLGLGCENNTMESFKESLHSYNKERVRFLIA |
| 121533397 | 185 | NHPNAGAVLVLGLGCENNNVPEFQKVVGSYNADRVKFLVA |
| 15613053 | 186 | LHPNAAGVLVLGLGCENNHIAAFKQVLGDYDDRRVKFLAV |
| RAAC01076 | 199 | RHPNAAGVLVIGLGCENNRIEAFRERLDQASLERVAFLEL |

| | | |
|---|---|---|
| 52081816 | 226 | QEVSNEVTEGVKLLKEIYKHAKGDHREDVPLSELKIGLKC |
| 52787203 | 226 | QEVSNEVTEGVKLLKEIYKHAKGDHREDVPLSELKIGLKC |
| 15893984 | 222 | QDVEDEISSGCELLKELYEKIQKDEREEVSISELKIGLKC |
| 121533397 | 225 | QEVEDEIAAGLELLSDLIAYAGQFLREDCPASELVVGLKC |
| 15613053 | 226 | QEADNEMEQGLAIIEELISYAKTAKREPIPLSKLKVGLKC |
| RAAC01076 | 239 | QRTTDEFADGMRLLEDLVERARAFVRQPVPVARLKLGLKC |

FIG 7B

| | | |
|---|---|---|
| 52081816 | 266 | GGSDGFSGITANPLLGRLSDFLIAQGGTAVLTEVPEMFGA |
| 52787203 | 266 | GGSDGFSGITANPLLGRLSDFLIAQGGTAVLTEVPEMFGA |
| 15893984 | 262 | GASDGFSGITANPLLGKLSDFLIAQGGTTILTEVPEMFGA |
| 121533397 | 265 | GGSDAFSGITANPLVGAFSDLLIACGGSTVLTEVPEMFGA |
| 15613053 | 266 | GGSDGFSGITANPLVGAFSDKVVAHGGTTVMTEVPEMFGA |
| RAAC01076 | 279 | GGSDGLSGVTANPLVGQVADRVVARGGTALLTEVPEMFGA |

| | | |
|---|---|---|
| 52081816 | 306 | ETLLMERAENEEVFHKIVRLINDFKQYFIDHRQPVYENPS |
| 52787203 | 306 | ETLLMERAENEEVFHKIVRLINDFKQYFIDHRQPVYENPS |
| 15893984 | 302 | ETILMNRAKDEKVFAKTVNLINDFKKYFMSYNQPVYENPS |
| 121533397 | 305 | ETILMNRAQDKAVFDKTVRLINDFKNYFMAYNQPIYENPS |
| 15613053 | 306 | ETILMNRAKDQATFEKMVRLINDFKEYFLRHNQPVYENPS |
| RAAC01076 | 319 | ETVLMDRADSPETFAKIVDLIQSWKDYYTRHGQPVYENPS |

| | | |
|---|---|---|
| 52081816 | 346 | PGNKAGGITTLEDKSLGCTQKAG.TSKVADVLEYGDVLKK |
| 52787203 | 346 | PGNKAGGITTLEDKSLGCTQKAG.TSKVADVLEYGDVLKK |
| 15893984 | 342 | PGNKAGGITTLEDKSLGCTQKSG.SSEVVGVLKYGETLEN |
| 121533397 | 345 | PGNKKGGITTLEEKSLGCTQKGG.RATVVDVLGYGETVTR |
| 15613053 | 346 | PGNKEGGITTLEEKSLGCVQKGG.FAEVVDVLPYGERLEK |
| RAAC01076 | 359 | PGNKAGGITTLEEKSLGAVQKGGRLSRVVDVLGYGDPAVK |

| | | |
|---|---|---|
| 52081816 | 385 | KGLNLLSAPGNDLVASSALAAAGCQIVLFTTGRGTPFGTF |
| 52787203 | 385 | KGLNLLSAPGNDLVASSALAAAGCQIVLFTTGRGTPFGTF |
| 15893984 | 381 | KGLNLLSAPGNDLVASTALASAGCHMVLFTTGRGTPFGTF |
| 121533397 | 384 | KGLNLLNGPGNDAVAATALAAAGCHLVLFTTGRGTPLGTA |
| 15613053 | 385 | PGLNLLQGPGNDLVSVTALAAAGAHFVLFTTGRGTPFGGP |
| RAAC01076 | 399 | PGLNLISAPGNDMVSVSALAASGAQLILFTTGRGTPFGGP |

| | | |
|---|---|---|
| 52081816 | 425 | VPTMKISTNTAIYEAKRHWIDFNAGKVLEDRSEDDVLKEL |
| 52787203 | 425 | VPTMKISTNTAIYEAKRHWIDFNAGKVLEDRSEDDVLKEL |
| 15893984 | 421 | VPTVKISTNSDIYNKKKNWIDFNAGALLENQSMDQVLKEF |
| 121533397 | 424 | VPTVKIATNSELFRRKTTWMDFNAGELLEGKSLEALADEF |
| 15613053 | 425 | VPTVKISTNTSLYERKKHWIDFNAGRLVEGATLDEVAEEL |
| RAAC01076 | 439 | VPTLKIASNHQLASSKPGWIDFDAGRIALGESMNDLAEEL |

| | | |
|---|---|---|
| 52081816 | 465 | TAYLIEVASGRQ.LNNEINDFRELAIFKTGVTL |
| 52787203 | 465 | TAYLIEVASGRQ.LNNEINDFRELAIFKTGVTL |
| 15893984 | 461 | INYLLGVANGNM.ANNEKNNIREISIFKNGVTL |
| 121533397 | 464 | FAYVLAVASGRP.TKAEEMGFREIAIFKNGVTL |
| 15613053 | 465 | LNYGVKLASGEVRAKNEEYGFKEISIFKDGVIL |
| RAAC01076 | 479 | LHKVIRVASGEELARNEVNGYREIAIFKDGVTL |

FIG 8A

| | | |
|---|---|---|
| 114843317 | 1 | MDYKDLLKKLSESYGVSGHERGIYDLLKKEF |
| 76795342 | 1 | MDYKNLLKKLCESHGVSGHERGIYDLVKEEF |
| 76796625 | 1 | MDYKDLLKKLSENHGVSGHERGIYDLLKKEF |
| 20515428 | 1 | MDYKELLKKLSESHGVSGHERGIYQLLKKEF |
| 125973125 | 1 | MDYINILKDLSTYPGVSGQEDKLSGYIAKLF |
| RAAC04341 | 1 | MRYEEVSPLSKYVSVFKQLLEAHGGPGFEEDVRNLILPHL |

| | | |
|---|---|---|
| 114843317 | 32 | EPISDEVKEDNFGNLIFKKKGTKG..KYKVMLAAHLDEIG |
| 76795342 | 32 | AQISDEVTEDKFGNLFFLKKGTKG..KYKVMLAAHLDEIG |
| 76796625 | 32 | EPISDEVKEDNFGNLIFKKKGTKG..KYKVMLAAHLDEIG |
| 20515428 | 32 | EEISDEVLEDNFGNLIFKKKGLKG..KYKVMLAAHLDEIG |
| 125973125 | 32 | EKYCDSVEIDEFYNVIGIKKGIGGSGGRRIMVTAHLDEIG |
| RAAC04341 | 41 | SEYATEMWTDALGNLIGLVPGVGEGRRPRVLVSAHIDEIA |

| | | |
|---|---|---|
| 114843317 | 70 | LMVKDIDEKGFIKFTTVGGVDQRTLPSQEVIVHGKK.DLL |
| 76795342 | 70 | LIVKDIDDKGFIKFTTVGGIDQRTLPSQEVIVHGKK.DIL |
| 76796625 | 70 | LMVKDIDEKGFIKFTPVGGVDQRTLPSQEVIVHGKK.ELL |
| 20515428 | 70 | LMVKDIDEKGFIKFTPVGGVDQRTLPSQEVIVHGKK.ELL |
| 125973125 | 72 | LMVKSIDEKGFITVSNIGGVDSKVLLAQEVVIHGKK.EIY |
| RAAC04341 | 81 | LVVTRIESGGFLRLAQAGGFDPRTLVGQEVVVHAQSGRVW |

| | | |
|---|---|---|
| 114843317 | 109 | GVIGSKPPHLLSSEDMEKAIKIDDMYVDVGLPKKEVEELV |
| 76795342 | 109 | GVIGSKPPHLLSLGDMEKAIKIEDMYIDVGMSKKEVEELV |
| 76796625 | 109 | GVIGSKPPHLLSSEDMKKAIKIDDMYVDVGLPKEEVEKLV |
| 20515428 | 109 | GVIGSKPPHLLSSEDMEKAIKIDDMYVDVGLPKEEVEKLV |
| 125973125 | 111 | GIIGAKPPHLLTPEEIKKAVKMEDLVIDTGLSAEEVRKYV |
| RAAC04341 | 121 | GVIGAKPPHLTPPSERSKAAKLEDLYVDLALPEEEVRARV |

| | | |
|---|---|---|
| 114843317 | 149 | KIGDIITIKRDFRELLNDYVSGKALDDRAGIVVMAVCLDE |
| 76795342 | 149 | KIGDVITIKREFRELLNDYVSGKALDDRAGIAVMAVCLEE |
| 76796625 | 149 | SIGDIITVKREFKELLNENVSGKALDDRAGVVVMAVCLEE |
| 20515428 | 149 | SIGDIITVKREFRELLNDNVSGKALDDRAGVVVMAVCLDE |
| 125973125 | 151 | SVGDIVTFKVEPLVLQNNRFSSKSLDNRAGVVALLDIMEN |
| RAAC04341 | 161 | RVGDRVTLRRSPVDLLNGRIAGKSVDNRASAAVLLEALAL |

| | | |
|---|---|---|
| 114843317 | 189 | LKKLYHYHDVYAVVTLQEEVGVRGATTSAYNVEPDIAIAI |
| 76795342 | 189 | LNKLYHYHDVYAVATLQEEVGVRGAITSAYNVEPDIAIAI |
| 76796625 | 189 | LKKVYHYHDVYAVVTLQEEVGVRGATTSSYNIEPDIAIAI |
| 20515428 | 189 | LRKMYHYHDVYAVATLQEEVGVRGAITSSYNIEPDIAIAI |
| 125973125 | 191 | LTLLNHKDDVWFVATVQEEVGLRGANIAAYNINPDLAIVI |
| RAAC04341 | 201 | LKGMVHSADLYAVFTVQEEVGLRGARTAGFGLAPDIAIAV |

| | | |
|---|---|---|
| 114843317 | 229 | DVTHGKARGVSLE..IELGKGPAIGKGPNIHPAVYKGLVE |
| 76795342 | 229 | DVTHGKARGLSIE..IELGKGPAIGKGPNMHPAVYKGLVE |
| 76796625 | 229 | DVTHAKARGVSRD..IEIGKGPAIGKGPNIHPAVYKGLVD |
| 20515428 | 229 | DVTHAKARGVSRD..IEIGKGPAIGKGPNIHPAVYKGLVD |
| 125973125 | 231 | DVCHGQIPGTPKESVFPVGKGPAVAVGPNLHRKYTKKMIE |
| RAAC04341 | 241 | DVTFGAFPGQAPDESFPLEGGVAISFGPNLHRRVFRRLVD |

FIG 8B

```
114843317   267  AAKNYNINYQVEPLPGPSGTDAWAIQVSREGVPTGLVSIP
76795342    267  AAKSYNINYQVEPLPGPSGTDAWAIQISKDGVPTGLVSIP
76796625    267  IAKKYNINYQIEPLPGHSGTDAWAIQVSKKGVPTGLVSIP
20515428    267  IAKKYNINYQIEPLPGHSGTDAWAIQVSKKGVPTGLVSIP
125973125   271  LAKEENIPYQIDVEPGDTGTEAWAVQVSREGIPTLLVSIP
RAAC04341   281  CADRHRIPYQIELSQGPVGADANAFQIAGPGLAAALIGPP 114843317   307  LRYMHTSVETANMKDVISSGKLLAYYIANLP.EELEGHLC
76795342    307  LRYMHTSVETANMKDIINSGKLLAYYIANLP.EELEGHLC
76796625    307  LKYMHTSVETANMKDIIESGRLLAHYIANLP.EELEGHLC
20515428    307  LKYMHTSVETANMKDIIESGRLLAHYIANLP.EELEGHLC
125973125   311  LKYMHTVIETLSIDDIKNTGRLIARFISMTG.NEMEEGLC
RAAC04341   321  IRYMHTSVETVAYDDIWQCARLLAHYLAEVDAAQVEELTC 114843317   346  Y
76795342    346  Y
76796625    346  Y
20515428    346  Y
125973125
RAAC04341   361  Y
```

FIG 9A

| | | |
|---|---|---|
| 125973126 | 1 | MLIKELTELNGVSGNED |
| 15893508 | 1 | MLLDKLCNAAGPSSFEG |
| 20515429 | 1 | MLLKELTELLGASGDEK |
| 76796624 | 1 | MLLKELTELLGASGDEK |
| 114843316 | 1 | MLLKELTEIMGASGDEK |
| RAAC04342 | 1 | MAVRATPRPLLGGGRRAGGGVDMLLKELTEAFGPTGFED |

| | | |
|---|---|---|
| 125973126 | 18 | EVRKFIKEEAQKYADSITEDSMGNLICYKKGGSSKYRVML |
| 15893508 | 18 | DVRAIIKKEIKAFVDEIKVDRMGNIIAHKKG..SGKKIML |
| 20515429 | 18 | EVREKIKEIVKPYVDELYVDRIGNLIACKKGKKEKPKVML |
| 76796624 | 18 | EVREKIKEIVKPYVDELYVDRIGNLIACKKGKKEKPKVML |
| 114843316 | 18 | EIREKIKSIVEPYVDNVYVDKIGNLIACKKGKKDKPKIML |
| RAAC04342 | 41 | EVRGIVRRELDAMGLSVRTDVLGNVIASTGEHHPGPRVML |

| | | |
|---|---|---|
| 125973126 | 58 | SAHMDEVGFMVTGY.....DDGLIKFASIGGIDERILPGK |
| 15893508 | 56 | DAHMDEVGFIITSIN....EDGTIKFASIGGINGKIIPSK |
| 20515429 | 58 | AAHMDEVALMVKSVN....EDGTLSFSPVGGVDNRILVAK |
| 76796624 | 58 | AAHMDEVALMVKSVN....EDGTLSFSPVGGVDNRILVAK |
| 114843316 | 58 | AAHMDEVGLMVKSVN....EDGTLSFFPVGGVDNRILVAK |
| RAAC04342 | 81 | DAHMDEVGLMVTHIGEGREEGGLLRFRPLGGVDPRVLVSK |

| | | |
|---|---|---|
| 125973126 | 93 | RVLVGEKRIPGVIGSKPIHLQEKAERGNNIKLKNMYIDIG |
| 15893508 | 92 | VVYIGENKIPGVIGIKPIHLQSAEERKGSASYDNCFIDIG |
| 20515429 | 94 | AVKVGEKKINGVIGAKPIHLQKKGEQEKPLDFDELYIDIG |
| 76796624 | 94 | AVKVGEKKINGVIGAKPIHLQKKGEQEKPLDFDELYIDIG |
| 114843316 | 94 | TVKVGEKGINGVIGAKPIHLQKRDEQQKPLDFDSLYIDIG |
| RAAC04342 | 121 | PVLIGERRIPGVIGAKPVHLQQPSEREKPIPMEKLYIDIG |

| | | |
|---|---|---|
| 125973126 | 133 | AEKKEEAEKLAPLGEYIAFYSMYTEFGDGCIKAKALDDRV |
| 15893508 | 132 | SKSKEETKKYVSLGDYAVFSTEYGEFGEGFIKAKALDDRV |
| 20515429 | 134 | AASKEEALKHISPGDYVYFESNFEILGDYVKAKALDDRI |
| 76796624 | 134 | AASKEEALKHVSPGDYVYFESNFELLGDYVKAKALDDRI |
| 114843316 | 134 | ATSKEEALKHVSPGDYVYFDSNFEILGNYVKAKALDDRI |
| RAAC04342 | 161 | ARDADDARRHVKPGDPVVFATAYQELPHRMAKAKSFDDRV |

| | | |
|---|---|---|
| 125973126 | 173 | GCAILLEILKERY.GFDLYVCFTVQEEIGLRGAGVAAFRV |
| 15893508 | 172 | GCAVLIELLKENY.ECDLYAVFNVQEEVGERGAYVSAFQV |
| 20515429 | 174 | GCNVLIEILKNTY.EYPVCAAFTVQEEVGLRGAGVAAYNV |
| 76796624 | 174 | GCNVLIEILKNTY.EYPVCAAFTVQEEVGLRGAGVAAYNV |
| 114843316 | 174 | GCNVLIENLKNEY.EYTVCAAFTVEEEVGLRGAGVAAYNV |
| RAAC04342 | 201 | GCYILLEALRRWKGALPVFGAFTVQEEIGLRGAHAAAYQI |

| | | |
|---|---|---|
| 125973126 | 212 | NPDIAIVVEGTTCSDVPGAREHEYSTVMGNGAALTIMDRT |
| 15893508 | 211 | RPDIGIALEGTVCADMPNVPEYLRATELGKGPAISIMDKS |
| 20515429 | 213 | EPDFALVVEGTVAADVVDSEPHLVSTELGKGPAISLMDRT |
| 76796624 | 213 | DPDFAIVVEGTVAADVVDSEPHLVSTELGKGPAISLMDRT |
| 114843316 | 213 | EPDFAIIVEGTVAADVTDSVPHLVSTELGKGPAISLMDRT |
| RAAC04342 | 241 | EPDIAIALEGTVAHDVVGTPSHGQSTVVGKGPAITVQDGQ |

FIG 9B

| | | |
|---|---|---|
| 125973126 | 252 | SYSNKKLVDFMYKTAKDKNIPVQYKQTATGGNDAGKIQLT |
| 15893508 | 251 | SIYNEEITLELIKIAKENNLAHQMRKSTSGGNDAGAIAST |
| 20515429 | 253 | TLYDRKIIDKIVRIAEENNVPYQFRRIASGGNDAGKIHLT |
| 76796624 | 253 | TLYDRKIIDKIVKIAEKNKIPYQFRRIASGGNDAGKIHLT |
| 114843316 | 253 | TLYDKKLIDKIAKIADENKVPYQFRRIASGGNDAGKIHLT |
| RAAC04342 | 281 | TVANRRFAEFLWETAKARNIPVQWRRVKGGTNDFGAIHRV |

| | | |
|---|---|---|
| 125973126 | 292 | REGVVVASVSVPCRYIHSPVSVMNRRDYESCLNLVKAVLE |
| 15893508 | 291 | GEGAKVAAVSVPCRYIHSSVSVASLKDIENTIELLKKYLL |
| 20515429 | 293 | KGGIKTVAISVPCRYIHSFNSVAKLSDFENTVKLVDLVIK |
| 76796624 | 293 | KGGIKTVAISVPCRYIHSFNSVAKLSDFENTVKLVDLVIK |
| 114843316 | 293 | KGGIKTIAVSVPCRYIHSFNSVAFLEDFNNTVKLVDLIIK |
| RAAC04342 | 321 | GKGVLGGAISVPVRYIHAPTQVVSLDDVSHAIDLVVAVLD |

| | | |
|---|---|---|
| 125973126 | 332 | EFDNNESLIESFKLHNVK |
| 15893508 | 331 | SFKGGK |
| 20515429 | 333 | NIEEVLK |
| 76796624 | 333 | NIEEVLK |
| 114843316 | 333 | NIEKEALI |
| RAAC04342 | 361 | EIAKGGFRP |

FIG 10

```
20515430    1   MSVNVELIKKLTQAFGPSGSEEKVFEIIREEVKGFCDEIT
76796623    1   MSVNVELIKKLTQAFGPSGSEEKVFEIIREEVKGFCDEIT
125973127   1       MFDLLKKFTGIVGVSGNEEEIREAIIEEIKECVDEIK
125973126   1        MLIKELTELNGVSGNEDEVRKFIKEEAQKYADSIT
RAAC04343   1       MRDWVMRLIDFVAPSGSEEAVVQSLLDHVREAADEIW
```

```
20515430    41  HDAMGNMICVKKGKGKK..IMVAAHADEIGIMVTHIEEEG
76796623    41  HDAMGNMICVKKGKGKK..IMVAAHADEIGIMVTHIEEEG
125973127   38  VDTLGNLIAVKKGKGKK..IMVAAHMDEIGVMVTYIDDKG
125973126   36  EDSMGNLICYKKGGSSKYRVMLSAHMDEVGFMVTGYDD.G
RAAC04343   38  VDALGNGIARKRGEGPH..LMLAAHVDEPGVMVIDIDDRG
```

```
20515430    79  FLRFTTIGGVYVEHLVGRRVKFKN....GTVG..VIG.VE
76796623    79  FLRFTTIGGVYVEHLVGRRVVFKN....GTVG..VIG.VE
125973127   76  FLRFSAVGGVSRYDCIGQRVKFKN....GVVG..AVYYEE
125973126   75  LIKFASIGGIDERILPGKRVLVGEKRIPGVIGSKPIHLQE
RAAC04343   76  YLRVVSVGEVHARECVGQEVRFTN....GAVG....LVHA
```

```
20515430    112 HLEDKKDFKLEKLYIDIGAKDKKEAEELVKIGESGSFVGE
76796623    112 HLEDKKDFKLEKLYIDIGAKDKKEAEELVRIGDSGAFVGE
125973127   110 KLEDMKNLQLSKMYIDIGARSREEALKMVNIGDVACFVGD
125973126   115 KAERGNNIKLKNMYIDIGAEKKEEAEKLAPLGEYIAFYSM
RAAC04343   108 DPAKQGDLDFDALVVDVGARSREDAERMAPIGTAGAVHVP
```

```
20515430    152 FVEAGD.RLISKAFDDRIGCYVAIEALKNVK.TENELYFV
76796623    152 FVEAGD.RLVSKAFDDRIGCYVAIEALKNVK.TENELYFV
125973127   150 AVLQGD.TVISKALDNRSGCAVVVKAIKELKKTDNEIYFV
125973126   155 YTEFGDGCIKAKALDDRVGCAILLEILKERY..GFDLYVC
RAAC04343   148 AATWGESVVTGRALDNRLGCAVAAEVFRNLAARGLNVSVA
```

```
20515430    190 FTVQEEVGLRGATTAAYSINPDFAIAVDVTATGDTP..KA
76796623    190 FTVQEEVGLRGATTAAYSINPDFAIAVDVTATGDTP..KA
125973127   189 FTVQEEVGLRGAKTAAFSIKPDIAIAVDVTMTGDTP..ES
125973126   193 FTVQEEIGLRGAGVAAFRVNPDIAIVVEGTTCSDVPGARE
RAAC04343   188 FTAQNAVGARAAQAAAFQLEPRYALVIDGATADDVFN...
```

```
20515430    228 KKMAVALGKGAAIKVMDRSIIVSPSVRDMMIEVAKENSIP
76796623    228 KKMAVALGKGAAIKVMDRSIIVSPSVRDMMIEVAKENNIP
125973127   227 HPMEVKCGGGPAIKVKDRSVICHPEVRKLLEESAKRNNIP
125973126   233 HEYSTVMGNGAALTIMDRTSYSNKKLVDFMYKTAKDKNIP
RAAC04343   225 HQTVLSLGKGPVLKVMDRGTVVPLEGKRAVEKAADRLNLL
```

```
20515430    268 YQLEILEFGGTDAGAIHLSRGGVPSGVISIPTRYVHSVSE
76796623    268 YQLEILEFGGTDAGAIHLSRGGVPSGVISIPTRYVHSVSE
125973127   267 YQLEILEAGGSDPGSIHLTAGGIPSGAISIPVRYVHSPVE
125973126   273 VQYKQTATGGNDAGKIQLTREGVVVASVSVPCRYIHSPVS
RAAC04343   265 LQYEVSREAWSDTGAIQLARAGCVAVALGYPVRRAGAFAM
```

```
20515430    308 MVDKKDVEASINLLIKILEK
76796623    308 MVDKNDVEASINLLIKILEK
125973127   307 TASMSDINNAVKLLVEAIC
125973126   313 VMNRRDYESCLNLVKAVLEEFDNNESLIESFKLHNVK
RAAC04343   305 TADISDAERLVDLAVATVETLLG
```

FIG 11A

| | | |
|---|---|---|
| 89098529 | | |
| 116620373 | | |
| 52081815 | | |
| 52787202 | | |
| 116623151 | | |
| RAAC01275 | 1 | MTCVHRWKRGLSAGASLALVAAAATGWTVHARFAHADNVV |

| | | |
|---|---|---|
| 89098529 | 1 | MAVYHIS |
| 116620373 | 1 | MKSTCRVALVGLLAACAWSAEFDVK |
| 52081815 | 1 | MSLQKIKEEIVKKLKVPVFPNRSFDVT |
| 52787202 | 1 | MSLQKIKEEIVKKLKVPVFPNRSFDVT |
| 116623151 | 1 | MRVLLLLIAALALRAAEFRVT |
| RAAC01275 | 41 | DLVAQTGDLDASLAQVLHGAPFAMPIPSLPDIVPRVYDIT |

| | | |
|---|---|---|
| 89098529 | 8 | EYLKGNAG..LATEGIQKAIDEAYQNGGGKVVIPAGEFLT |
| 116620373 | 26 | TFGAAGDGKKKDTAAIARAIDAAAKAGGGTVVVSPGRYLT |
| 52081815 | 28 | SFGADENGKNDSTEAIQKAIDQAHQAGGGRVTVPEGVFLS |
| 52787202 | 28 | SFGADENGKNDSTEAIQKAIDQAHQAGGGRVTVPEGVFLS |
| 116623151 | 22 | DYGAKADGKTVNTVALQKAIDAAAKAGKGVVVFAPGVYLS |
| RAAC01275 | 81 | EYGAKPGIGQVNTQAIQAAIDAASQHGGGIVDIPPGYWVT |

| | | |
|---|---|---|
| 89098529 | 46 | GPLFLKDNIELHLENGAHLKFSDKQEDYP.VVTSRWEGVK |
| 116620373 | 66 | GALTLKSNVTLDVEAGATLLGSPDPEDYP.LRENVWG..E |
| 52081815 | 68 | GALRLKSNVDLHIAKGAVIKFSQNPEDYLPVVLTRFEGVE |
| 52787202 | 68 | GALRLKSNVDLHIAKGAVIKFSQNPEDYLPVVLTRFEGVE |
| 116623151 | 62 | GALFLKSNMELRLDEGVEIRGVQDLAAYP.LMQTRVAGIE |
| RAAC01275 | 121 | GPIVLKSHVDLNVESGAQLQFSGDHDLYP.....LVPSGN |

| | | |
|---|---|---|
| 89098529 | 85 | RKVYASCLFAEGARNIAVTGFGTIDGNG............ |
| 116620373 | 103 | KKEYSSLIYADGAVHITIRGRGTIDGQG............ |
| 52081815 | 108 | LYNYSPLIYAYEADNIAITGKGTLDGQGD........... |
| 52787202 | 108 | LYNYSPLIYAYEADNIAITGKGTLDGQGD........... |
| 116623151 | 101 | MKWPAALLNVYEQSNVRLSGKGTVDGDG............ |
| RAAC01275 | 156 | SYIVQSPISATNAVDVAITGHGVIDGAGNTWRPVEKSKLS |

| | | |
|---|---|---|
| 89098529 | 113 | ..................MEWWD..VFRNRR......... |
| 116620373 | 131 | ..................QAWWKRMGWPDRRKIAPEQRTA |
| 52081815 | 137 | ..................DEHWWPWKRGTNGQPSQEKDRNA |
| 52787202 | 137 | ..................DEHWWPWKRGTNGQPSQEKDRNA |
| 116623151 | 129 | ..................KIWWDLYWKMRREEYEPKGLRW |
| RAAC01275 | 196 | ADQWNALVASGGVVSPDGSTWWPTAQGANAQAYIKAHPNM |

| | | |
|---|---|---|
| 89098529 | 124 | ......EELKYP.........RPKLISFDHCEHITLRDV |
| 116620373 | 153 | AERAELAKLEYG.........RPHMIKLVRSKHVVIEGL |
| 52081815 | 160 | LFEMAERGIPVTERQFGKGHYLRPNFIQPYRCKHILIQGV |
| 52787202 | 160 | LFEMAERGIPVTERQFGKGHYLRPNFIQPYRCKHILIQGV |
| 116623151 | 151 | AVDYDCR..............RPRLIQIYKSQGVDLVSL |
| RAAC01275 | 236 | TYQDDLQVKDYL.........RPYMVYFQGCQRVWLQGV |

FIG 11B

| | | |
|---|---|---|
| 89098529 | 148 | RLINSPSWTVNPICCRDITVDNVSILN..PADSPNTDGID |
| 116620373 | 183 | HLINSASWTVNPLLCEFVRIDGITIEN..PVPSPNTDGIN |
| 52081815 | 200 | TVLNSPMWQVHPVLCENVTVDGIKVIG....HGPNTDGVN |
| 52787202 | 200 | TVLNSPMWQVHPVLCENVTVDGIKVIG....HGPNTDGVN |
| 116623151 | 176 | TLKRPGFWTVHICYSERVTVDGLTIRNNTDGKGPSTDGID |
| RAAC01275 | 266 | TFENSPFATVKVNTSKDVVIDDVNIRN..PWYGQNTDGID |

| | | |
|---|---|---|
| 89098529 | 186 | PESCRNVRISNCHIDVGDDCIAIKSGTEDTEERVAC..EN |
| 116620373 | 221 | PESCRNVQILNSRIDVGDDCVTLKSGKDEAGRRVGRPDEN |
| 52081815 | 236 | PESCKNVVIKGCHFDNGDDCIAVKSGRNADGRRINIPSEN |
| 52787202 | 236 | PESCKNVVIKGCHFDNGDDCIAVKSGRNADGRRINIPSEN |
| 116623151 | 216 | IDSSSDVLVAHCDIDCNDDAICLKAGRDADGLRVNLPTER |
| RAAC01275 | 304 | VSADENVVLYRDVIDTGDDGIALESSGNDAAG..VFNEQD |

| | | |
|---|---|---|
| 89098529 | 224 | ITITNCTMVHGHGAVVFGSEMSGDIRNVTIS..NCVFQDT |
| 116620373 | 261 | ITITNCVMLKGHGAVTIGSEMSGGVRNVVVS..NCVFQGT |
| 52081815 | 276 | IVIEHNEMKDGHGGVTIGSEISGGVKNVIAEGNLMDSPNL |
| 52787202 | 276 | IVIEHNEMKDGHGGVTIGSEISGGVKNVIAEGNLMDSPNL |
| 116623151 | 256 | VRITDNVVRGGAAGVTIGSETSGGIRHIEVD.HLTVMSAV |
| RAAC01275 | 342 | VVVADCIVHNGHSGFAVGSYTDGGIRDVWVT..GDVYDGT |

| | | |
|---|---|---|
| 89098529 | 262 | DRGIRFKSRRGRGGVVEDVRVDN.IVMEGVICPFIINLYY |
| 116620373 | 299 | DVGIRVKSQRGRGGIVEGFVVSN.VVMQDVASAFTLTSFY |
| 52081815 | 316 | DRALRIKTNSVRGGVLENIYFHKNTVKSLKREVIAIDMEY |
| 52787202 | 316 | DRALRIKTNSVRGGVLENIYFHKNTVKSLKREVIAIDMEY |
| 116623151 | 295 | PAGILFKSASTRGGTIEDIAIRN.VITVGVATPVSITLNW |
| RAAC01275 | 380 | ESGLRFKSGVGKGGLVEDIDMDHIVMRDISGAAITFDDGY |

| | | |
|---|---|---|
| 89098529 | 301 | FCGPR..........GKDQYVWDKNPYPVTAETPMFRRLH |
| 116620373 | 338 | AGTDK..........PGD.......LFPVGEGTPRLRDFR |
| 52081815 | 356 | EEGD.......................AGDFKPVVRTVD |
| 52787202 | 356 | EEGD.......................AGDFKPVVRTVD |
| 116623151 | 334 | NPAYSYAKLPEGVKDMPDYWRVLTEVVPPGKGIPHFRDVR |
| RAAC01275 | 420 | VDNGADTS..............SLQAPGPNSYVPQFENMT |

| | | |
|---|---|---|
| 89098529 | 331 | FANITARNVHASAGYIYGLAEQYATDITFSQIDISLAKNA |
| 116620373 | 361 | FSNITAR.GSKTAGQITGLKEMPIENITFTGVRI...... |
| 52081815 | 372 | VKQLKSM.GGQYGIRVLAYDHSPVTGLKVADSEIDG.... |
| 52787202 | 372 | VKQLKSM.GGQYGIRVLAYDHSPVTGLKVADSEIDG.... |
| 116623151 | 374 | ISRVKST.GAQRAFAVSSYAESPLVDFQFKDIDIE..... |
| RAAC01275 | 446 | ISNVSCEYAGQS.IYMNGLPNAPISNIMLDDVNIT..... |

| | | |
|---|---|---|
| 89098529 | 371 | VPGKPAMMAGIEDMANRGFYVGFAKDVLFSRVTIENHEGP |
| 116620373 | 394 | ..............QAETGMKITNAKDVTFQDVIIEAAKGD |
| 52081815 | 407 | ..............VDVPMELKHVKDPVFSNLYINGKRYD |
| 52787202 | 407 | ..............VDVPMELKHVKDPVFSNLYINGKRYD |
| 116623151 | 408 | ..............AKTAGSIANTQGWKFENMTIKTADGT |
| RAAC01275 | 480 | ..............ANKPPQIQNTSNLVENQVQIQSGVTM |

FIG 11C

| | | |
|---|---|---|
| 89098529 | 411 | AFHIEHSEDVEVISCKSRNTKEGEELVREVAAK |
| 116620373 | 421 | AVSVVDSVGIELGRLKGRAAT.....VRERP |
| 52081815 | 433 | SHKA |
| 52787202 | 433 | SHKA |
| 116623151 | 434 | TVK |
| RAAC01275 | 506 | LGEIPH |

FIG 12A

```
15614786    1             MPIFYTEQTKEFHLQTKGSSYIFTVLDNQQL
90961985    1             MPITYNEQSREFHLYNNKISYLIKILANEQL
148544139   1              MITFDEQQRVFHLKNKEISYLFSVEEGNIL
76796346    1             MPIHFNDKTRTFHLTAKDTSYIIHVLKNDAV
114844315   1             MSIHFNDKTKTFYLTAKDTSYVIYVLKNGAV
RAAC01615   1     MAIGKGRPSMPIIFHSDERLFHLMTPRSSYVFRVGHDGLL 15614786   32     GHLYYGKKIEHRDSFTHLLRFQRRATSSCVFEGNLEFSLD
90961985   32     GQLYFGKRIPNRGNHDYLVENTYRPVTSYVFDDDYSFSLG
148544139  31     SHLYFGPAIRNYHGERRYPRVDRGFSGNLPGSMDRTYSKD
76796346   32     LHAYFGKKIKNANIYHVLKLSHVS.IDTDNINFGNYLMLD
114844315  32     LHAYFGKIIKTPNIYHLLKPHIS.IDNDIINFGNQLMLD
RAAC01615  41     EHVYWGARLEDASDLVRLARACQR.LDARPEHMR.AIDIG 15614786   72     LIKQEFPSYGTTDYREPAFQILQENGSRITNFEYKNHVIS
90961985   72     NVKQEYPAYGTTDQRRPALDIKQPNGSRITDFKYVSHKIY
148544139  71     DLLQEYSGNNTGDYRVPAIIIKTENGSRLTDFRYKSYKIL
76796346   71     FLPQEYPAYGNTDFRSPAYQIQLENGSTVSDLRYLSHKIY
114844315  71     FLPQEYPAYGNTDFRSPAYQIQLENGSTVSDLRYLSHKIY
RAAC01615  79     SLRLEYPSFGTGDHRDPAYEVLQPSGSHASQLVYESHQIR 15614786   112    SGKKPLKGLPATYVESEEEAATLEVFLYDSLIDVELVLTY
90961985   112    AGKRKLTGLPATYVEDESEATTLEINLYDELIQVTLCLQY
148544139  111    PGKPKLAGLPASYVKSDKEAETLEVILVDETIGAQLILSY
76796346   111    KGKPKLEGLPATYVENEDEADTLEIELYDKVANLKVTLIY
114844315  111    KGKPKLEGLPATYVENEDEADTLELELYDKVANLKVTLIY
RAAC01615  119    PGKPPLPGLPAFYVESDFEADTLEISLVDPAISLRVILSY 15614786   152    TVFAETNVITRHARFINHHSSPVQLMRALSMSVDLPDADF
90961985   152    TIFENSAAIARSVKFSNNSDQKYQLKTALSLNLDLPDANY
148544139  151    TIYNERPVITRNARLVNTSNQELRIEKIASMQLDLTKHDY
76796346   151    TAFRDYDVITRSVRFENMGKEDIKLLRALSMNVDFNDDKF
114844315  151    TAFRDYDVITRSVRFENMGKEDIKLLRALSMNVDFNDSNF
RAAC01615  159    TAYRDFDLVCRHARLENAGTEPLVLRRALSASVDLDLREA 15614786   192    QMLQLSGSWSRERYVKERALVPGIHQISSTRGASSSQQNP
90961985   192    EWLQFSGAWGRERHLHKTPLRPGIQAINSARGASSHMQNP
148544139  191    DVISVPGQYALERQPERQELRRGITEFSSRRNSSSHHMNP
76796346   191    DMLQLSGAWARERHVIRRPLTPGVQSIESRRGASSHQQNP
114844315  191    DMLQLSGAWARERHVIRRPLVPGAQSIESRRGASSHQQNP
RAAC01615  199    DFVQLSGAWIRERFIQRTPLSPGRHEIMSRSGASGHKHNP 15614786   232    FIALKRPQTTEFHGEVYGFSLVYSGNFLAQVEVDQYDV.S
90961985   232    FVILKRPFTTEEQGEALGVSFVYSGNFLAQAEVDEYSV.T
148544139  231    FVALVDKNTDEFQGNALGVLLVYSGNHQFTLEKDQIDQ.I
76796346   231    FIALLRKDADEWHGDVYGFSLVYSGNFLAQVEVDQYKM.A
114844315  231    FIALLRNDADEWHGDVYGFSLVYSGNFLAQVEVDQYNM.A
RAAC01615  239    FFALAAPHTTEEGGEVRAFALVYSGNFLGACEMEPMRQNV
```

FIG 12B

```
15614786   271  RVQMGIHPFDFQWLLEAGESFQTPEVVMVYTDQGLNHLSQ
90961985   271  RLQIGIDPFQFSWCLKPNETFQTPEAILAYTSEGLNQLSQ
148544139  270  RLITGINDYDFEWVLEPGKDFQTPEAIMGFSQQGLNGMSQ
76796346   270  RVSMGINPFDFSWLLKPGETFQTPEVVMVYSDSGLNKMSN
114844315  270  RVSMGINPFDFSWLLKPGETFQTPEVVMVYSDGGLNKMSN
RAAC01615  279  RAQIGIHPSDFSWRLEPGERFVTPEAALVYSDEGWGGMSR 15614786   311  LYHSLYRSRLVRGNWRDRPRPILLNSWEATYFDFTEDSLV
90961985   311  TFQKLYTTRLARGYWRDKERPILINNWEATYFDFTEEKLL
148544139  310  VFHKLLRDRVARGKYQYADRPIVINNWEATFFDFDDKKLD
76796346   310  TYHKLYRNRLMRSKFKDKERPILINNWEATYFDFTEEKLK
114844315  310  TYHKLYRNRLMRSKFKDRETPILINNWEATYFDFTEEKLK
RAAC01615  319  TFHRAIRKRLCRGTYRDVRPVLINNWEATYFHFDEEDLV 15614786   351  EFAKEGKKLGVELFVLDDGWFGTRNDDTTSLGDWFVNSEK
90961985   351  SIAKKAKELGIELFVLDDGWFGERTKETAGLGDWYVNRNR
148544139  350  QIIDEAKPLGIEMFVLDDGWFGHRNDDNSSLGDWFVNQDK
76796346   350  ELAKEAKDLGIELFVLDDGWFGKRNSDNSSLGDWFVNKEK
114844315  350  ELAKEAKDLGIELFVLDDGWFGKRNSDNSSLGDWFVNKEK
RAAC01615  359  EIAEQARDLGAEMFVLDDGWFGQRDDDHTSLGDWWPHPRK 15614786   391  LPNGIEGLAEKIEALGLAFGLWFEPEMVNKESELFKKHPD
90961985   391  LKNGISGLSRKIHDLGMMFGLWFEPEMVNKDSDLYRKHPD
148544139  390  LTGGLKRVADRTHEHGMKFGLWFEPEMISVDSKLYKEHPD
76796346   390  IPSGLDGLAKGINSLGLKFGLWMEPEMVSPDSDLYREHPN
114844315  390  IPSGLDGLAKGINSLGLKFGLWMEPEMVSPDSDLYREHPD
RAAC01615  399  LPNGLRHLADRIHALGLRFGIWMEPEMVSPKSELYREHPD 15614786   431  WIIHVEGRSQSHGRNQYVLDFSRAEVVDAIYEMMAELLRK
90961985   431  YIIETPKRHASHGRKQYVLDFSRKEVVDNIYEQLVKILDE
148544139  430  YALHEPNRGMTLSRNQLVLDFSRKEVVDNIYNQMCLILDK
76796346   430  WCIHVPNRPRSESRNQLVLDLSRKDVQDYIIKVVSDILES
114844315  430  WCIHVPNRSRSESRNQLVLDLSRKDVQDYIIKVVSDILES
RAAC01615  439  WCLHVADRPRSERRHQLMLDLTREDVRAFVVNAVSRVIEE 15614786   471  APISYIKWDMNRHLTEIGSPAWPKERQQEIAHRYILGVYD
90961985   471  GEIDYIKWDMNRNITECYSIAYPPEQQGEIMHRYILGVYD
148544139  470  VLLDYIKWDFNRNLTEVFSSAADADHQGEISHRYVLGLYD
76796346   470  ANISYVKWDMNRNMTEIGSALLPPERQRETAHRYILGLYR
114844315  470  ANISYVKWDMNRNMTEIGSALLPPERQRETAHRYILGLYR
RAAC01615  479  GAVDYIKWDMNRPMTEVGSAALPPERQREVAHRYVLGLYE 15614786   511  LYERLVSEFPDVLFESCASGGCRFDPGMLYYAPQTWTSDD
90961985   511  LYERLIERYPKILFESCASGGGRFDAGMLYYAPQAWTSDD
148544139  510  LMERLVTRYPNILFEGCSGGGGRFDAGILYYMPQSWPSDD
76796346   510  ILEEITTRFPDVLFESCAGGGGRFDPGMLYYMPQTWTSDN
114844315  510  ILEEITTRFPDVLFESCAGGGGRFDPGMLYYMPQTWTSDD
RAAC01615  519  ILETLTSRFPNVLFENCASGGGRFELGMLHYMPQTWTSDN
```

FIG 12C

```
15614786    551  TDAIERLKIQYGTSMVYPLSSIGAHVSAVPNHQVRRVTSL
90961985    551  SDAIERLKIQYGTSFGYPQSMMGAHVSASPNEQLGRNTPL
148544139   550  TDAVERLKIQYGTSLTYPISSMTAHVSVSPNQQTGRSTSF
76796346    550  TDAVERLKIQYGTSIVYPLISMGSHVSAVPNHQVHRITPL
114844315   550  TDAIERLKIQYGTSIVYPLISMGSHISAVPNHQVHRITPL
RAAC01615   559  TDAVSRLKIQHGTSLVYPPVAMGAHVSAVPNHQMGRVTPF 15614786    591  ETRGNVAFFGAFGYELDVTQLTDEEKENMKKQIAFYKEHR
90961985    591  KIRGDVAFFGAFGYELDLDKLSSTELASIKKQIELMKKYR
148544139   590  KMRGDVAMSGVFGYELDLADLTEEDRQMVKEQIKFYKAHR
76796346    590  KTRLDVAISGNFGFELDLTKLSEEEKDLAKKYVKKYKEIR
114844315   590  KIRAHVAMSANFGFELDLTKLSSEEKDEIKKYVEKYKEIR
RAAC01615   599  ALRAGVAMCGNFGFELDPRRLSDAERREARQAVERYKALR 15614786    631  ELIMFGTFYRLRSPFVGDGNVTSWIVVSEDQSEALVGYYQ
90961985    631  SIFQYGTFYRLKSPFEG..NIVSWMVVSEDKSQAIVGYYK
148544139   630  HLIQYGAFIRLESPFDS..NTVAWEFVSPDKSEALLFMFK
76796346    630  KLIQFGDFYRLLSPFEG..NETAWMFINEEKTEFVAFYFK
114844315   630  KLVQFGDFYRLLSPFEG..NETAWLIVSEDKREFLLYYFR
RAAC01615   639  HLVQFGDFYRLLSPFDG..PEAAWMFAVEDGSEALVAYFC 15614786    671  TLAKVNAGFRQLKLTGLQECGLYQIDGMIGTYGGDELMHS
90961985    669  ILNDVNCEYRRLCLPGLDADTLYNVQEELGSYLGN.FTGD
148544139   668  QLHTNRFEINNTKMAGLDPTIDYHDEMTDKTYGGD.....
76796346    668  VLATPNDTIKRIYLKALNPDYKYALQDTGEVYGGD.....
114844315   668  VLGGANEPIKRLRLKGINPDFNYVLEDDGSEYSGD.....
RAAC01615   677  TYPDPLDPPARVVLRGLRPEARYRCEALGESFRGD.....

15614786    711  GLQLPNEFSGASALREDEQSGDFQSYVFKLKRIESDRH
90961985    708  ELANIGLVTTDASAGQNQETTDFYSKLFILERCGELSD
148544139   703  ELMNVGLFR......DPTHTGDFISEVHYFKGE
76796346    703  ELMYAGIAI.......PQLEGDFQSVMMHFKKEA
114844315   703  ELMYAGKVI.......PELKGDFQSIMMHFKEESIKDG
RAAC01615   712  ALMRHGLVI.......PRQVGDGQAVLIHLKQIGEGDRP
```

FIG 13A

```
76795700
114844102   1    MWYIVALVLLLIATSIVHISKNQRLSREDSIR..DFDD
20517160    1    MWYAVFVLILLLAG...IYLKSKKIEVDDSMR...EFDD
125973736   1  MQMQLYILYLLGLFGILLCLFLLAIFSNCNERQRQLKVQD
118725340   1       MNNILILLIITLIAIVAALIGIVLK.NRPSYEVQIED
RAAC01621

76795700
114844102  37    IILNSEEMEKHAAEIAQNHNIMKRTKLSYLLIPRMNKNYN
20517160   34    IILSSEEMEKHAEELAQNHVIANRNRASFLLIPRMNKNYE
125973736  41    ASLTFDELEAYAKEIAIEHSVSGKKSMFSWPIPRMNDNYR
118725340  37    VFLNSDDLMRHAEQLAKTQTTDKRKLGIRRVRERIERNFH
RAAC01621   1    MAFDTELERRAHALALTQDISSTRGGGSDLWPILRRKAA 76795700
114844102  77    YIKNVYRNLNSILKEEDVYISQEEEWLLDNFYIIEEQVKE
20517160   74    YIKSVYRSLNNLLKEKDTYISQEEEWLLDNFYIIEEQVKE
125973736  81    YIMSVYKEMN.EDVQKGISTTPAAEWLLDNFYIIEEQVKS
118725340  77    RVLEMYQKFN.LDISASFPVPPAAEWLLDNFYIIEEQKSM
RAAC01621  40    RVRNLATRLE...REPAACSEPAHEWLIDHAAYLELQAML 76795700
114844102 117    IRKSLSKSYYSGLPGLKNGLFKGYPRIYAIAFELVLHTDG
20517160  114    IRKSLSKKYYAGLPVLKNGAFRGYPRVYALAFELVLHTDG
125973736 120    LRRDLTKEVYAKLPVLDSGHLKGYARIYSIALELLSHTDG
118725340 116    LMKELS.EVKQALPVISEGTYAGYPRVFAIAADLVSHCDG
RAAC01621  77    AERLWPNAVVRKLPRMAE...TGEPRVVTLAAAYLDATRG 76795700
114844102 157    KIDEKAIINFIKAYQTKALLSSSELWALSLMIRIALVEKI
20517160  154    KIEEKGIINFIKAYQKKALLTTSELWALSLMIRIALIEKI
125973736 160    RIDEKVLVNYIKAYQSNNVLTGRELWAFPIMLKLVLIEKT
118725340 155    NVNEKIIRDFIAAYQKHTFLSIQELWMLSTMLKAALLEKL
RAAC01621 114    HVEAETLIRFVEAYQDVQVLTTHECHQLANGLRVAILTRL 76795700
114844102 197    KKICEKIVETRHQREKAEKILTLLLEKEMKYEEVKKLIRN
20517160  194    KKVCEEIVESRLQREKAEKMLSALMEKEMSYEEVKKLIKS
125973736 200    RYICEKIAKAQEQRRKVEEILKAFDENIENTTQLITAIDN
118725340 195    WAVCDRMFTNRQDWYRAEGIVNGIRHNNENCDDFRRHID.
RAAC01621 154    AEASDEIQHRYETCRAVGRLLDEIERG..DGPVAVRRAID 76795700
114844102 237    NINVADRFPLQFIEHLVSRLRKEGSNSVNVIQSIEKILME
20517160  234    NIKVVDRFPLQFVEYLVSRIKREGSNSSDILKTLEKILME
125973736 240    ELKGKYEVNSAFIEYLAYKFRKMGRAYTHVLRYIDERLGE
118725340 234    ...QLEEITPAFAEHLIKKLRKDGAKTLWMIECLDSILVQ
RAAC01621 192    RFSKGRGLGAVEVVHLVHHLSEWEPDSQELREWLAAHVAN
```

FIG 13B

```
76795700
114844102  277  YDTSINDVAEKAHQIQAKRQISIGNAITSLKTVSSLDWAQ
20517160   274  YDSSINDIAEKAHYFQAKRQVSIGNAIVSLKTVSSLDWAE
125973736  280  SGTTVDDITQKEHNEQTASKASIGNCIMSLKFISTVNWVD
118725340  271  KSTSTDSLISEDHFNQATLQVSTGNVINSFRALSGFDNTV
RAAC01621  232  SSESIERLTTYEAEWHAEIQVLIGNLVQSLHALERMSWQP 76795700
114844102  317  IFESLSSVEQVLRQDPDGTYPKMDFESRDYYRHEIEKIAK
20517160   314  IFETLSPVEQVLKQDPDGTYPKMDFESKDYYRHEIEKLAR
125973736  320  IFEQLSKVEQILREDPSGFYSLMDFDSRNYYRNVEKLAL
118725340  311  LFEQLSEVERLLKLDPCGIYPQMDFDSRNYYRDIVMNLGS
RAAC01621  272  IASRISRVESCLRQEPTGDYLRLDPTSQNVLTQQVSWLSE 76795700
114844102  357  YYNTSETYVAKKAIECAKEVTEQEGKLG......YINHVG
20517160   354  YYNVSETYVAKKAVECAREVADQGENLG......YINHVG
125973736  360  KYKVSESHVAKKAVELARNAVENGNLTDK.....RLTHVG
118725340  351  KYDTTEINIARLCLDLAREKYDENPSIT......AETHVG
RAAC01621  312  AFRLPEAMIAETAVSLAREAWEKAGSPTASSDLPREAFVA 76795700
114844102  391  FYLVGKGRSILENKLSNKSKRTISWRKIAKKSPETLYVGL
20517160   388  FYLIGKGRSILESKLNNKKRRFFDFYRIRQKNPATVYFGL
125973736  395  YYLVGKGICELEKEIGYEKSFNQRMFERIKEHPACLYFGF
118725340  385  YYLAGKGRSAFSNKIG.......KYKEHSFKNCEKWYITA
RAAC01621  352  YYLCDPDGMHALHRSLKERAKPRSVPQIALRRRPLRSYLL 76795700
114844102  431  ILIFLLVEEFFALKYIANFSNKWGLLFISGVILL..IPFS
20517160   428  IILFFALGEIISLGYLRHFTGSFWNLFASSLVLA..IPLS
125973736  435  IGFITVLLLLCVTKYSLFRAEKYGIALSIIAVLATIIPAT
118725340  418  IVLFSVVIALIPTVNSFSRENGRLAFIVLLTGILSIIPAS
RAAC01621  392  GVAFLFAAILWAVLGGFTGGFRAPLGATLALAVLLALPVS 76795700
114844102  469  EMSVQLVNWILVHIFKPVVLPKIELKEGIPEDAKTMVVIS
20517160   466  EISIQMTNWVLMHIFKPVMLPKIELKDGIPDDAKTFVVIS
125973736  475  DIAVNFVNWVLCKMIKPSLLPKLDFENGIPEEYATMVVIP
118725340  458  EIVVSVLNSCISRIVKPARLPKLELNDGIPEDWATMVIIP
RAAC01621  432  EWVISLVHEGIRRAVRPVPLLRLDFSEGIPEDARTLIVLP 76795700
114844102  509  SLLPDEKRTKELIENLEVYYHANREKNLYFGLLGDFKDAP
20517160   506  SLLPDEKKAKELVENLEVYYHANRERNLYFGILGDFKDAP
125973736  515  ALLPDENRARELIDNLEVYYLANREKNLYFSIAGDFKDAP
118725340  498  TLIPNVKRTVELIDNLEVFYLANKGSNIYFSLAGDFKDSD
RAAC01621  472  VIWASEADVDEAFDKIELHHLTNRGAHLYFAVLSDLRDAD
```

FIG 13C

```
76795700
114844102    549  FEVMSEDEKIVKCALEQIEKLNEKYSKNGE.......KIF
20517160     546  LEVMPEDEKIVKATLEEIEKLNEKYAENGE.......KVF
125973736    555  NKEMAGDKKIIETALGRIAELNEKYGRKNEGGEKDSRDIF
118725340    538  DETLSDDNEIVEAAIKRVQDLNRKYCKDAK.......PIF
RAAC01621    512  APHLPEDEPLLARARARLEALRHKYG..........AARF
```

```
76795700
114844102    582  YYFHRKRKYNQMQKSWMGWERKRGALVEFNELLRGKEDTS
20517160     579  YYFHRKRIYNEMQKSWMGWERKRGALMEFVDLLRGEKDTT
125973736    595  YYFHRHRQFNEKQNKWMGWERKRGALLEFNEVLLGSRTTS
118725340    571  YFFCRKRRYNEKQKKWLGWERKRGAILEFNRLLRRDRNTD
RAAC01621    542  FWFHRDRVLNRADGVYMGWERKRGKLVEFVELLRGKRDTT
```

```
76795700
114844102    622  FYVVSGDVAKLN.IKYVITLDADTNLPIDTAKKLVGTMLH
20517160     619  FYIVSDDVSKLG.IKYVITLDADTNLPIDTAKKLVGAMLH
125973736    635  YSIMSHDVSQLPKIKYVITLDADTILPLGAARKLIGTMAH
118725340    611  YVFNSATIDSLPNIKYVITLDADTQLPLDTAKQMVGAMAH
RAAC01621    582  FRVKDGDLAVLPTIRYVFTADLDTELPIGTVQRLVGTMHL
```

```
76795700
114844102    661  PLNKAVIDRDYGVVVEGYGLLQPRIGIDIESANATLFSKI
20517160     658  PLNRAIIDRDEGIVVEGYGLLQPRIGVDIESANASLFSKI
125973736    675  PLHRPVIDEQKGIVTEGYGLLQPRIGFDIESVNKSLFSRI
118725340    651  PLNKAYFDKEKGVVTKGYGIMQPRVDVNIESAVKSLFTRV
RAAC01621    622  PYNRPRLNARGTRVDQGYGVLQPAVAVSPRSTQASRFARL
```

```
76795700
114844102    701  YAGEGGIDPYTTAVSDVYQDLFGEGIYTGKGIYDVDVFRE
20517160     698  YGGEGGIDPYTTATSDIYQDLFGEGIYTGKGIFDVDVFRE
125973736    715  FAGEEGIDPYASAISDVYQDLFGEGIFTGKGIYDLEVFQK
118725340    691  FAGQGGIDPYTTTVSDVYQDAFGEGIFTGKGIYDVDIFTT
RAAC01621    662  WSGETGVDPYAFAISNPYQDWFGRGLFVGKGLIHVDAFHT
```

```
76795700
114844102    741  LLRDTIPDNSILSHDLLEGSFVRTGLVSDIELIDGYPAKY
20517160     738  LLKDTIPDNSILSHDLLEGSFVRTGLVTDIELIDGFPAKY
125973736    755  LLKDAIPDNTVLSHDLLEGSYVRAGLVTDIEFIDGYPSKL
118725340    731  ALDKTIPENSVLSHDLLEGSFLRTALVTDIELIDGYPAKY
RAAC01621    702  VLCDRIPDNRVLSHDILEGGFLRAGLVADVEVVESQPATL
```

```
76795700
114844102    781  NSYIMRLHRWVRGDWQLLPYLKSKIKNRKGEMVKNPLSLI
20517160     778  NSYMMRLHRWVRGDWQLLPYLRSKIRNRRGELIRNPLSLI
125973736    795  NSYAMRLHRWVRGDWQLLPWLRGKTKDRKGNVIKNPLSLI
118725340    771  NSFMMRLHRWTRGDWQLLPWILG.........KNPLSML
RAAC01621    742  RAYMRRAHRWVRGDWQLTYWLRRVCRDRRGETQPVDLCGF
```

FIG 13D

```
76795700
114844102    821  TKWKIIDNLRRSVVSVALMLMLFLGFS.LLPGSSFLWLGV
20517160     818  TKWKIMDNLRRSLISISLIVMLFLGFS.ALPASALFWVAV
125973736    835  SRWKILDNLRRSIVAPSITLLIALGFS.ILPGSSLFWLGA
118725340    801  SRWKMIDNLRRSLVQPVLALIALLAVW.LFRNSYREWLIL
RAAC01621    782  TRWNIVDHVRHSLVNPALVLLMGSGMSGLLPGPAYAYGAV
```

```
76795700
114844102    860  AILTVFFPILPALVDTIFKGQFRHYWEKRHKAVITSIEAA
20517160     857  AALTVFFPVMPALFDLIFRGQLRQYLEKRHRAVITGVEVA
125973736    874  SLLTIYFPLITGTIDYIASKPLGAITSKRYKPAICGLKAS
118725340    840  ALISLCSPVLNYFVQLLIAGNYKIYIAKRRTTIITGFKAI
RAAC01621    822  LLITVFLPFLRQLESIRPG...........EWDWRSAATA
```

```
76795700
114844102    900  FYQSLLNFAFLPYQAYMMADAIVRTLTRLYITRKNLLEWV
20517160     897  FYQALLNFIFLPYNAYIMADAIIRTISRMYITKRNLLEWV
125973736    914  FLQMTLQFVFLPYNAWLMVHAAVLSLVRVLFTKRNMLEWV
118725340    880  LLQLGLLLTFLPYQAELMVNAVSKSIFRVYITKKNLLEWV
RAAC01621    851  LGQSLVMLVTLPFMAVVEADASLRALYRMLVSRRRLLEWI
```

```
76795700
114844102    940  TAADMEKRLRNDFASFFKRMWIVLVEGLALVALVMYFKPQ
20517160     937  TAADMEKRLKNDFISFVKRMWVVLLKGVVLILLTAYFKPG
125973736    954  TALDAERGLKNSLKGYVIKMKAAAFQALVVVVLAFAFKTG
118725340    920  TAADMEMSLKNGVGSYYRRMWFCPVYGAVILLLSILYRQS
RAAC01621    891  PSSHADRSDGSPAPLLYEPAGYAVALACSVPGLFGTWEQA
```

```
76795700
114844102    980  D.LIGAIVLFFLWAISPYIAFYISQPIISKEKTVSQEEM.
20517160     977  A.LIFAVGVFFLWAFSPYVAFYISQPVLLKIKFILDEDI.
125973736    994  FSAAVSVLPFAVWVSSPFIAYWISKETVYKTETLSDEEN.
118725340    960  F.VPVASLLFVLWVLSPWIAYYISVPTEKNRVVLDSAGV.
RAAC01621    931  L...SSTLALAVWLPAHAVARFLAKPAGEARVAAPDPALS
```

```
76795700
114844102   1018  EELRLIARKTWRFFEDFVTESQNYLPPDNFQEDPPNGIAE
20517160    1015  EEVRLIARKTWKFFEDTVTEAQNYLPPDNFQEDPPNGIAE
125973736   1033  LELRRIARKTWRYYEEFVNRRNNYLAPDNFQEDPPNGIAY
118725340    998  EEVRLLARRTWCYFDEFAGPEENYLPADNYQEEPYKGAAH
RAAC01621    968  AHLREVATAMWRFYERYVGEEDHHLPPDNVQFEPVERIAH
```

```
76795700
114844102   1058  RTSPTNIGLYLVSVVGARDLGYITTTEMVERIKKTLTTIG
20517160    1055  RTSPTNIGLYLVSTVGARDLGYITTSEMVDRIENTINTIK
125973736   1073  RTSPTNIGLGMLAALTARDLGYIGTLELCDIISRTMSTVE
118725340   1038  RTSPTNIGLLLVSNLAARDMGYINTLDFLARIENTISTVE
RAAC01621   1008  RTSPTNIGLYLLCVAAAADLEIIPKEGAIARLERTLATLT
```

FIG 13E

```
76795700
114844102  1098  KMEKWNGHLYNWYNTRTLEPLRPYYVSTVDSGNLVGYLIT
20517160   1095  KMEKWNGHLFNWYDTRTLKPLRPYYVSTVDSGNLVGYLIT
125973736  1113  KMEKWNGHLYNWYDTRTLETLRPRYISTVDSGNFVCYLIT
118725340  1078  KMDKWNGHLYNWYNTVTLEVLRPKFISTVDSGNFIGYLMV
RAAC01621  1048  SLDRWHGHLFNWYDTRTLRPLAPRYVSTVDSGNLVCAMLA
```

```
76795700
114844102  1138  VKEAIGEFLNKPLIDIELAKGLKDTIKMLN.........I
20517160   1135  VKEALEEFLDKPVIDLEFLRGLKDTVRMLK.........I
125973736  1153  LKEGLAEYLNRPLEDRAFIDGIRDTASLIADENENPYKDI
118725340  1118  LHEGLSGLMESPIYDFSTIEGLFDLLEICN..........
RAAC01621  1088  LGQALREWAASDADIAPRAR....................
```

```
76795700
114844102  1169  EGITEDIFRNILNKKTLMPSDWEVFLSKISEKLSSTEDEV
20517160   1166  ERIDKSLFEEFLKKGDIDPLAWKKILDDLEEVEE......
125973736  1193  SCLKECIVISEGRSYVDIPQMMKALTKLSEDGNKMKDSKD
118725340  1148  .......SEIEGSKAYFDTELLKKLTDS............
RAAC01621  1108  ........................................
```

```
76795700
114844102  1209  GNIERLKNIIGALKREMKEFLAWTEFDERQKEQE......
20517160   1200  ...ERLRDIVKKFKNEIREFMPWLEFEDAEG.........
125973736  1233  VWKAKVDSMIEMLKIELYTYMPWCDMIDELTEAFEKSEAD
118725340  1169  ......DNIEESFKNLLPAVLKLVDELDKSK.........
RAAC01621  1108  ........................................
```

```
76795700
114844102  1243  ...IFKRYKEVFEEHSSPKELEKVYKNYLLEIEEV...FE
20517160   1228  ......GYGEIFNECNSFEELKKVYEKYLEETFRA...KK
125973736  1273  IKEAFHGIIRKLNSDYSLKAMPVVYRETIKQIEKLRKKLK
118725340  1194  ............RTGYWFKKLDSNINTFNSEYTKYRGILF
RAAC01621  1108  ........................................
```

```
76795700       1        MLRK.................NLQSLIMI
114844102  1277  KATEEEKALLKSQKDKVARALEKIKNLEAEIENIKSIIEN
20517160   1259  EGLPEFKIKQIQR......AVEKIEELKERILKLKQEIED
125973736  1313  DGQQKNIEGLDRLKEALEGATESADKLVKRYVDLINRICR
118725340  1222  APLKNVPQELKRIQ..................QLQTKVQQ
RAAC01621  1108  ................................RLADAMEG
```

```
76795700      14  CWLR..................................K
114844102  1317  LVEKTEFRHLYDEKRQLFSIGYNVEEEKLTKSYYDLLASE
20517160   1293  IIEKTEFKHLYDEKRQLFSIGYNVEEEKLTKSYYDLLASE
125973736  1353  IADETEFVHLYDKKKQLFSIGYNIEENSLTNSYYDLLASE
118725340  1244  LIDAMEFKYLFDPARNLFTIGFDVEDGHASKSYYDLFASE
RAAC01621  1116  FAREIDFRPLYRPDLRLFSLGFHADRNELENIVYDLLASE
```

FIG 13F

```
76795700      19  QGKQVLLLLQKEKLIKKHWFKLGRMLAIENRYKGLVSWSG
114844102   1357  ARQASFIAIAKREIDKKHWFKLGRMLAIENRYKGLVSWSG
20517160    1333  ARQASFIAIAKREVDKKHWFKLGRMLTRANRSKGLVSWSG
125973736   1393  ARQTSYIAIARGEVDQQHWFKLGRTLTQIDRYKGMVSWSG
118725340   1284  ARQTSLVAIARGEAGRQHWFKLGRKLVRVNGMKGLASWTG
RAAC01621   1156  ARQASFIAIASGQVPASHWFALSRTMTRAGRYQPLLSWSG 76795700      59  TMFEYFMPLLIMKNYQNTLLDETYAFAVRVQKNYAKELGI
114844102   1397  TMFEYFMPLLIMKNYQNTLLDETYAFAVRVQKNYAKELGI
20517160    1373  TMFEYFMPLLIMKNYENTLLDETYSFAAKVQKEYGVKLGI
125973736   1433  TMFEYFMPLLIMKSHKNTLLDETYSFVVRSQKKYGKQRNL
118725340   1324  TMFEYLMPRLLIKSYSNTLIDKTYEFVVKTQIKYGLANKA
RAAC01621   1196  TMFEYLMPALLMRHLPHTLWEETYRGVVWRQIAYARERGV 76795700      99  PWGISESGFYAFDINLNYQYKAFGVPSLGLKRGLSHDKVV
114844102   1437  PWGISESGFYAFDINLNYQYKAFGVPSLGLKRGLSHDKVV
20517160    1413  PWGISESGFYAFDMSLNYQYKAFGVPILGLKRGLSHDKVV
125973736   1473  PWGISESGFYSFDINLDYQYKAFGVPWLGLKRGLVEDMVV
118725340   1364  PWGISESCYYAFDIGLNYQYRAFGVPHLGLKRGLANDFVA
RAAC01621   1236  PFGISESGFYAFDRDLNYQYRAFGVPGLGLDRGLEQHLVV 76795700     139  APYGSLLAIGVDVEGVLQNIRFLKKEGVEGKYGFYEAIDY
114844102   1477  APYGSLLAIGVDVEGVLQNIRFLKKEGVEGKYGFYEAIDY
20517160    1453  APYGSILAISVDPEGVMKNIEFLKKEGAEGEYGLYEAIDY
125973736   1513  SPYATMLVLPLVPRDAMDNLKRLIAEGAYGHYGMYEAIDY
118725340   1404  APYATVMALDIAPQECLENIHRFKEIGAFGNFGLYEAVDF
RAAC01621   1276  APYATMLALPFAPEQVAEALRQLRELGALGPYGYYEAVDF 76795700     179  TPERFPFGKKSAIVKSFMAHHQGMAFVALDNFINNNIMQK
114844102   1517  TPERFPFGKKSAIVKSFMAHHQGMVFVALDNFINNNVMQK
20517160    1493  TPERVPFGKKNAIVKSFMAHHQGMIFVAIDNFIHENIMQK
125973736   1553  TPERIPLGEKKGIVKSYMAHHQGMSILALNNYFNDNIMQK
118725340   1444  TNSRISKDQSYAVVKCYMVHHQGMSMLALVNFFKNNIMQE
RAAC01621   1316  TASRLPPGDRYKVVQSFMAHHQGMAFIAIANYLNRNLWVE 76795700     219  RFHKDPSIKAIQILLQEKMPMYLDITREEREEARKIQKVR
114844102   1557  RFHKDPRIKAAQILLQEKMPMYLDITREEREEARKIQKVR
20517160    1533  RFHRDPRVKATQILLQEKAPIYLDMTREEREEPRKIQKIR
125973736   1593  RFHADPVVDAAKLLLMEKVPSNIVFTKENKEKILPFKDVV
118725340   1484  RFHGNPLIKAVDSLLQEKFPAAAMITKEYREQPVGGMRKN
RAAC01621   1356  RFHRLPLVRAAEYMLYERMPKRPALLLKP......VHAAH 76795700     259  KEDGDFVRVLGESKTWLPEVHILSSGRYFVMLTEKGTGYS
114844102   1597  KEDGDFVRILGESKTWLPEVHILSSGRYFVMLTEKGTGYS
20517160    1573  KEDLDFVRVLGESRSWIPEVHIVSSGKYFVMLTEKGTGYS
125973736   1633  YDEKDFLRECGMPDPVLPKAHILSNGNYSVMVTDRGTGYS
118725340   1524  VNHKDTVIREYNKLSPYPGIHLLSNGNYYLMITDKGSGYA
RAAC01621   1390  APNFDRPVYARRRSGDDVAWNAVSNGSLTSFADARGEGGI
```

FIG 13G

```
76795700    299  KNNKGIFLTRWRKDLAQD.FGTFIFVQNINSNTVWSATYA
114844102  1637  KNSRGIFLTRWRKDLAQD.FGTFIFVQNINSNTVWSVTYA
20517160   1613  KNIKGIFLNRWRKDIAQD.YGTFIFIRNVDSNEVWSATFA
125973736  1673  R.WKNLDVTRWREDVTLDNYGMFFYIRDVQNDEVWTSTFA
118725340  1564  K.YHSMAVYRWINDYMQS.SGAFIYIRNLNSNEFWSTTYN
RAAC01621  1430  A.WRGIAVTRYRPDRHLPYRGPVMYVRDVDRGGVFRTTLH 76795700    338  PFYEKGQNYRVVFSADKAEYFKRVGNIDTHLEIVVSPEDD
114844102  1676  PFYEKGQNYRVVFSADKAEYFKRVGNIDTHLEIVISPEDD
20517160   1652  PFYQKGQHYRVVFSADKAEYFKRVGGIDSYLEITVSPEDD
125973736  1712  PGRKKPDEYKVEFTSGKAKYYRKDGDIDTLTEIVVCAGEN
118725340  1602  PTNTKPEAYKVIFAPHKAEFVRREGNIETNTEVIISSEDN
RAAC01621  1469  GG...GGHVEAEFRPDKSSWKRVVDGIESEWSVLVAPDRD 76795700    378  VEIRRLTLKNHSKHPRILEITSFGEISLIDLPTDVAHPAF
114844102  1716  VEIRRLTLKNHSKHPRILEVTSFGEISLIDLPTDVAHPAF
20517160   1692  VEIRRLTLKNHSKYPQILEITSFSEISLMDLPSDVAHPAF
125973736  1752  AEIRSITLANHGQESCVMEITSYFEPVLSHHGADIAHPAF
118725340  1642  TEVRRVSIHNHSSSKRIIELTSYMEVVLTQHEADSAHPAF
RAAC01621  1506  VEIRTLVLQNLGEDVRRLEVTYFAELALAKPAADIAHPSF 76795700    418  NKLFVKTEFLKEEDAILVCRKPREQGKNKLWAVHKVAVLS
114844102  1756  NKLFVKTEFLKEEDAILVCRKPREQGKNKLWAVHKVAVLS
20517160   1732  NKLFVKTEFLKDEDAIIVCRRPRDPEKSRLWALHKVVVLS
125973736  1792  GNLFIRTEFLAEHNCLIAGRRPRSEKEKPVWIMN.TVVLE
118725340  1682  SKLFVKTEYVDEYNGLLAMRRKRDDIKQTSWGYH.IASTN
RAAC01621  1546  QRLFVETGWDDARQVLWAQRRPESDDQPDVYAAFHLVAD.

76795700    458  GEIVGDTQFETDRAKFIGRGRSLKNPIALEADQPLSNTEG
114844102  1796  GEIVGDTQFETDRAKFIGRGRSLKNPIALEADQPLSNTEG
20517160   1772  GEAMGDTQFETDRLKFIGRGRSVRKPLALEPDQPLSNTEG
125973736  1831  GEGVGSLQYETDRMQFIGRGRNVSEPVALEPHRPLTNSVG
118725340  1721  GKAYGHVEYETDRSLFIGRNRNLAYPRAMEPDRPLSNSVG
RAAC01621  1585  EEAPAPVEWDSHRARFVGRGGSLAAPRGLWRRLRGE....

76795700    498  AVLDPIVSLRKRVKVMPGEVAKVVYISAITETKEKAIKIA
114844102  1836  AVLDPIVSLRKRVKVMPGEVAKVVYISAITETKEEAIKIA
20517160   1812  AVLDPIVSLRKRIRIMPGGVAKIAYISAITETKEEAVKIV
125973736  1871  AVLDPVMSFRQIVRVEPGKSVKISFVTAVANSREDVVEMA
118725340  1761  SVIDPVFSLRIRVTVEPGESTIVNFCMGACDNRKTAVEML
RAAC01621  1621  GVADPAAILRTAVTLAPGEKRALYVITALGEARDEVVETA 76795700    538  AKYKEENVVERDFEMSWTRSRVELDYLNLKPRELGLLQRM
114844102  1876  AKYKEENVVERDFEMSWTRSRVELDYLNLKPRELGLLQRM
20517160   1852  SKYKEENAIERAFEMSWTRSRVELEYINLKPRELGLFQRM
125973736  1911  TKFKSPQVIKDELGMAVTKSRVEARYLNLDTEEIELYQDM
118725340  1801  AKYSDPAAADRVIDMAWTRSIVEEGFINVDADEEKAYIKL
RAAC01621  1661  FEMRQPSARSRAAQLAWMRAQIDLRQLHLSPDDVEDAMEL
```

FIG 13H

```
76795700      578  LAHILFVSPQRRYREEMILKNVKGQSGLWAYGISGDLPIV
114844102    1916  LAHILFVSPQRRYREEMILKNVKGQSGLWAYGISGDLPIV
20517160     1892  LPYLIFASPQRKMREEMILKNTKGQSGLWAHGISGDLPIV
125973736    1951  ISHILFISPLQRQKQKWVMNNKKGQPGLWPYGISGDIPIV
118725340    1841  LPRLIFG.IDRREQAEYILSNSLSQSDLWPFGISGDLPIV
RAAC01621    1701  LSRFLSRHAFSPERRAAILQNELGQSGLWAHGISGDRPIV 76795700      618  LVEIEKMEEIEMVKWFLKAYEYWKMKGINIDLVILNKDKS
114844102    1956  LVEIEKMEEIEMVKWFLKAYEYWKMKGINIDLVILNKDKS
20517160     1932  LLEVEKMEEIELVKWFLKAYEYWRMKGINIDLVIVNKDKS
125973736    1991  LVMLDKTDDIDIVREVLKAHEYWRLKKLAVDLVILNEEEN
118725340    1880  LVTVKSRDSFEEIDWALKLHDFYRIKGVVFDLVILLTDEE
RAAC01621    1741  AVRLASAAEVPFVAKLARLTQYLAHMGFASDLVVIDETIS 76795700      658  GYLQPLHDKIKELINTTFSYDIFGKYGGVYLLQQNNLKEE
114844102    1996  GYLQPLHDKIKELINTTFSYDIFGKYGGVYLLQQNNLKEE
20517160     1972  GYLQPLNDKIKEVINTTFAYDVFGKYGGVYLLQENNLKED
125973736    2031  SYTNPVNSLLMDIIAESHADLINKPGGVFILKKSNMPPE
118725340    1920  SYIQPIFEMIRDMAVSGRSYELLDKRGGIFIRNSRQMKVE
RAAC01621    1781  SYRDEMRDRIRAEMARRGVHDAAT....LAVVKADQLSSA 76795700      698  DVYLLNTVVALKFEGGN.........ESIYDQIMIKETKN
114844102    2036  DVYLLNTVVALKFEGGN.........ESIYDQIMIKETKN
20517160     2012  DFYLLNAVAALKFDGKN.........ESIYDQIMVKVHKK
125973736    2071  DIDLICSVSRIILKGDA.........GDLKDQVKYARSIA
118725340    1960  QKNLLFASAKIILDADEGIPSLMEIIEGIEKSMDVEIHTP
RAAC01621    1817  ERALMESVAVATLRAGG.........PSVGAQLTGGRVRR 76795700      729  APKLK.....NWVKKVQNFEEIKLEELPLDYYNGFGGFSY
114844102    2067  APKLK.....NWVKKVQNFEEIKLEELPLDYYNGFGGFSY
20517160     2043  ALKPR.....SFQEKVSSCRDDGLEEIELQYYNGFGGFTP
125973736    2102  LAEFK.....QFEKKPASYDSKLAKDLELNFYNGLGGFGK
118725340    2000  LEPSEESSAPSLVSESEYSGKDVVTAAELFFNGFGGFTK
RAAC01621    1848  EESAR..LASDRLEPEPKRAPRDAGQVEGEFANGYGAFVD 76795700      764  DGKEYIIKWE.GKSTPAPWINVISNPSFGFQVSETGAGYT
114844102    2102  DGKEYIIKWE.GKSTPAPWINVISNPSFGFQVSETGAGYT
20517160     2078  DGKEYVIKWE.GKSSPAPWINIISNPNFGFQVSEVGAGYT
125973736    2137  DGKEYVIFLENGQNTPLPWINVISNQRFGFIVTESGSGYT
118725340    2040  DGREYVIQLSDGMSTPAPWVNVIANERFGFICTESGGGYI
RAAC01621    1886  DGRAYRMRVTRAKRPPRPWSNVLANPNFGALVTELGTGYT 76795700      803  WAENSREYKLTPWYNDPVLDPHGEVIYLTDEETGDRWSIT
114844102    2141  WAENSREYKLTPWYNDPVLDPHGEVIYLTDEETGDRWSIT
20517160     2117  WAENSREYKLTPWYNDPVLDPHGEVIYLIDEITGEKWTIT
125973736    2177  WFENSRENKLTPWSNDPVSDTPGEILYVMDEHAGDVWSVT
118725340    2080  WHLNSSQNKLTSWINDPITDTPSEIIYICNTQNGKVWSCT
RAAC01621    1926  WWRNSREFKLTPWHNDAAFDPPGEAVYIADLDRGIIASAT
```

FIG 13I

```
76795700      843  PLPAGKAKVHYIKHGFGYTSFETICCGLSQHLKMFVAKED
114844102    2181  PLPAGKAKVHYIKHGFGYTSFETICCGLSQHLKMFVAKED
20517160     2157  PHPAGNSGIYYIRHGFGYSTFESASCELKSRLTMFVPKED
125973736    2217  PLPVREKEPYMIRHGFGYTVFSHASHGIEQEMVQFVPVDD
118725340    2120  PLPVREAEPYTIRHGFGYTCFGHKSNGINQTLTQFAATEA
RAAC01621    1966  PSPAGDERTYDVTHRPGVTTFESDVEGVRVTLHVFVDSAE 76795700      883  SIKINLVTIKNLGNENRKLTVSYYIRPVLGVTDEITFPYL
114844102    2221  SIKINLVTIKNLGNENRKLTVSYYIRPVLGVTDEITSPYL
20517160     2197  SVKINLIKLKNTSKNSRKIQIVYYIRPVLGVTDEATSQYI
125973736    2257  SVKISILKLKNQSQENRGLSLTYYIRPVLGVSDQFTAMHI
118725340    2160  AVKFSILKLENITTSEMLLETAYYFRPLLGTEFPQTSPYI
RAAC01621    2006  PAKWMRVRLRNQSGEERRIRVAPYAEWVLGVDPFSNTPLV 76795700      923  FTKYDEKIGALMIKNVYNEDFANRLAFLSAS..EKINSFT
114844102    2261  FTKYDEKIGALMIKNVYNEDFTNRLAFLSAS..EKINSFT
20517160     2237  ASEFDKEERILYIRNVYNEDFVNRIAFLATS..EGINSYE
125973736    2297  NTKADN..GMIVIKNNYNDEFPGRVAFIDSS..LKVNSLT
118725340    2200  VTEFDETSNAIIIDNVYSADFRGLRAFLACS..ESGVSYT
RAAC01621    2046  VVRKMGEADAIAAENRYQEAFRGALGFLAVGGAGRTTGWL 76795700      961  GDRAEFIGVASSLTLPQALEYETLSNSTGISLDPCAAIQF
114844102    2299  CDRSEFIGVASSLTSPQALEYETLSNSTGISLDPCAAIQF
20517160     2275  SERGEFIGVGFDLSSPQALSYETLSNSEGLAVDPCSAIEF
125973736    2333  CDRKEFFGAG.DIANPEGIKRTSLSGTTGAGFDPCAAISV
118725340    2238  GSRLKFFGPGMEISNPAGMR.EELDSITGAGIDACAALKA
RAAC01621    2086  GDKTRFLGDG.SYARPDALLEDAWRGGDGPTPTPCAVLAR 76795700     1001  HVEVKAKEEKQFTILLGHGKNEEEVKRLILKYTNVENCQN
114844102    2339  HVEVKAYEEKQFAILLGHGKNEEEVARLISKYTNVENCKN
20517160     2315  SVEIGPGEEKEISILLGHAKEKKEAKDLVLKYLKVENCKK
125973736    2372  SVNLKPDEEKEIIFLLGAGRDEEEARQLSAKYKKLEEAKK
118725340    2277  SIRLRPGETKEILFIVGQEKSEK.VTEVISAFRNIENAKN
RAAC01621    2125  DLDLGPHEEAEVVILLGAAPDEHEAARLAR.LADPAAADR 76795700     1041  ELQRVQEFWQELLRRIQIKTPDKSMDLLVNGWLPYQTIAC
114844102    2379  ELQRVKEFWQYLLGRIQVKTPDRSMDLLVNGWLPYQTIAC
20517160     2355  ELEKVKGFWGEILGKLTVNTPDKSLDLLVNGWLPYQTIAC
125973736    2412  ALGEVKKFWELKLGALQFETPNTAMDILLNGWLLYQVVSC
118725340    2316  EMEKVKDSWNRRLGQIQVKTPDDSINLMLNGWLQYQVLSC
RAAC01621    2164  ALREVTRFWDDLLGRVQIRTPDRAFDILMNGWLVYQALAC 76795700     1081  RLWARSAFYQSGGAYGFRDQLQDAMNMVYLEPEFTKNQIV
114844102    2419  RLWARSAFYQSGGAYGFRDQLQDAMNMVYLEPEFTKNQIV
20517160     2395  RLWARSAFYQSGGAYGFRDQLQDAMNMVLNPEFTKRQII
125973736    2452  RLWTRSGFYQSGGAYGFRDQLQDSISLTHIWPEATRNQIL
118725340    2356  RIWARTGFYQAGGAFGFRDQLQDVMAVVYSLPELTKNQIL
RAAC01621    2204  RLWARTAFYQAGGAFGFRDQLQDALALIHARPDILRDQIL
```

FIG 13J

```
76795700    1121  NACQHQFVEGDVQHWWHPVLNKGIRTKFADDLLWLPYVTA
114844102   2459  NACQHQFVEGDVQHWWHPVLNKGIRTKFADDLLWLPYVTA
20517160    2435  NACEHQFIEGDVQHWWHPVLNKGIRTKFSDDLLWLPYVVA
125973736   2492  LHSRHQFIEGDVQHWWHEEKYKGTRTKFSDDLLWMPYATI
118725340   2396  LHCRHQFVEGDVQHWWHNQKMNGIRTRYSDDLLWLPYVTC
RAAC01621   2244  RAARHQYVEGDVQHWWHEELGKGIRTRFSDDLLWLPYAVS 76795700    1161  DYIEKTGDWPILDIEVNYLEDLRLKEEEEERYSTPRISET
114844102   2499  DYIEKTGDWPILDIEVNYLEDLRLKEEEEERYSTPRISET
20517160    2475  DYLEKTEDWAILEEKAGYLEDLPLKEEEEERYSVPSISSH
125973736   2532  EYIRITGDYDILYEETPFLEDEPLKEFEDEAYRVPRISHT
118725340   2436  DYINATGDFEILNLEERYITSPTLNENEHERYEVPSDSGL
RAAC01621   2284  RYLEATGDAALLDERAPYLVSAPLGDGELERYEDSVWSQE 76795700    1201  KGTVYEHCIRAIDYSLKFGEHGLPLMGAGDWNDGMNKVGN
114844102   2539  KGTVYEHCIRAIDYSLKFGEHGLPLMGAGDWNDGMNKVGN
20517160    2515  KGTVYEHCVKAIDYALKFGEHGLPLIGTGDWNDGMNKVGH
125973736   2572  VSTLYDHCIRAINRSLKFGEHGIPLIGSGDWNDGMNTVGN
118725340   2476  KGTVYDHCIRAIDKGLKFGIHGIPLMGGGDWNDGMNLVGV
RAAC01621   2324  EGTLAEHVARAVERALHFGDHGLPLIGIGDWNDGLSRVGA 76795700    1241  KGKGESVWLGWFLYTILQKFSPICQTKKDEEHAKKYQEIA
114844102   2579  KGKGESVWLGWFLYTILQKFSPICQTKKDEEHAKKYQEIA
20517160    2555  RGKGESVWLGWFLYTVLKKFASISEKMGDIERKEKYIKEA
125973736   2612  KGKGESVWLGWFLYSILKNFAPLCERMGDNELAKRYLDTA
118725340   2516  QGKGESIWLGWFMYCVLLRMIPICNKMGDVERAENYKTKA
RAAC01621   2364  KGRGESVWLAWFLADVVRRVAEIDHPEFAQHRAR.WLAMR 76795700    1281  NKLIKAIEENAWDGSWYRRAYFDDGTPLGSVDNSECKIDS
114844102   2619  NKLIKAIEENAWDGSWYRRAYFDDGTPLGSVDNSECKIDS
20517160    2595  ERLLKSIEENAWDGSWYKRAYFDDGTPLGSINNLECKIDS
125973736   2652  DRIVENIEKNAWDGKWYRRAYFDNGVPLGSIQNSECQIDS
118725340   2556  DAIIEAIEREAWDGSWYRRAYFDDGTPLGSMENDECKIDS
RAAC01621   2403  ERVLAAANESAWDGQWYRRAITDDGLWLGSAASPACRVDA 76795700    1321  ISQSWSVISKAGKEVRVKEAMKAVVNYLVNEEEGIIKLLT
114844102   2659  ISQSWSVISKAGKEVRVKEAMKAVVNYLVNEEEGIIKLLT
20517160    2635  ISQSWALISKGGRIERAKEAMKAVVNYLVNEEEGIIKLLT
125973736   2692  LAQSWAVISEGGDKERIAEAMSALENYLVKRDEGLIKLLT
118725340   2596  LSQSWAAITGAAKNSRVEEAMSAVEKYLVDRRNGLIKLLT
RAAC01621   2443  IAQSWAVISGGAPPDRAVRAMESFDRELVDRRLGVAHLLQ 76795700    1361  PPFDNGDLNPGYIKGYVPGVRENGGQYTHAAAWVILAFAE
114844102   2699  PPFDNGDLNPGYIKGYVPGVRENGGQYTHAAAWVILAFAE
20517160    2675  PPFDSGDLNPGYIKGYVPGVRENGGQYTHAAAWVILAFTE
125973736   2732  PPFDEGDLEPGYIKSYVPGVRENGGQYTHAAAWVVMAFAK
118725340   2636  PPFYDSELNPGYIKGYLPGVRENGGQYTHAATWVVYAFCK
RAAC01621   2483  PAFRDLRPSPGYIQGYPPGIRENGGQYTHGVIWSVIAWTR
```

FIG 13K

```
76795700    1401  LGEGDRAWQLYNMINPINHTRTPIECMKYKVEPYVMAADV
114844102   2739  LGEGDRAWQLYNMVNPINHTRTPIECMKYKVEPYVMAADV
20517160    2715  LGDGDTAWKLYNMINPINHTRTPIECMKYKVEPYVMAADV
125973736   2772  MGDGEKAMELFDLLNPINHSRTHIEYSRYKVEPYVMAADV
118725340   2676  LGDGERAWELFSMINPVNHARTKSESMTYKVEPYVMAADV
RAAC01621   2523  LGRADEAYELFSMLNPIHHADTPREVERYGNEPYVMSADV 76795700    1441  YAVEPHVGRGGWTWYTGAAGWMYRIAIENLLGLKKYGEKL
114844102   2779  YAVEPHVGRGGWTWYTGAAGWMYRIAIENLLGLKKYGEKL
20517160    2755  YAVDPHAGRGGWTWYTGAAGWMYRVAVEHILGLKKYGDKF
125973736   2812  YSVPPHTGRGGWTWYTGSAGWIYRVGFEYILGFKKRGETL
118725340   2716  YAVYPNEGRGGWTWYTGAAGWMYRIGIDHLLGIKKQGNSI
RAAC01621   2563  YTAEPNVGQGGWSWYTGAASWMYQAGLEAILGIRRHGTRL 76795700    1481  IIDPCIPKNWDKYVIEYNYKNTKYLIEVRNPEGVNKGVKE
114844102   2819  IIDPCIPKNWDKYVIEYNYKNTKYLIEVRNPEGVNKGVKE
20517160    2795  TVDPCVPRNWESFVIEYAHGHSKYVIKVINPDRVNKGVRE
125973736   2852  EIDPCIPGKWTDFTIKYRYYDTDYIIEVKNPEGVNTGVKK
118725340   2756  LLNPCIPQNMNEYSVRYVYGSSVYNITVKNPGHKNTTVER
RAAC01621   2603  LVEPCVPAHWPGFEVAYRYGSTLYRIRVERAPQG.AEARD 76795700    1521  VYIDGELVTDKTIDLTKEGNGHQVLVIMG
114844102   2859  VYIDGELVTDKTIDLTKEGNGHQVLVIMG
20517160    2835  IYLDGEPV.DKFVPLKDENKVFRVLVVMG
125973736   2892  VIVDGKVCDDGKVQLVNDKDTHKVEVYMGKK
118725340   2796  ITIDGKTTETNRIELIDDGRTHEVEAVM
RAAC01621   2642  SALTVEGVAPAEIDLVDDGQEHHVVVWLAAEGAEVLSDVQ 76795700
114844102
20517160
125973736
118725340
RAAC01621   2682  TVAARPREGARRYRMSSGARAFPASAAYRKRDPQP
```

FIG 14A

```
15616253
89099466    1                           MHFNRNVSERQEDL.
RAAC01755   1  MRWAAKRPRCSSICCRRARCHQARCCRRNSSCARRPEHFN
13470878    1                           MLSEFRLTVGGRS.
17227827    1  MTPDTLTNPDKIFLDGKTFIPADQLPIPEWPCVVSERPQ
72163378    1                           MKVWNISTGTSGEGS.
```

```
15616253    1        MDYRVIKENDVFLLTDEKGNIPENHS..YGAGLYT
89099466   15   .....MDYRVIKENDLFLLTDSKGNIPENHS..YGLGLYT
RAAC01755  41   WGRGIMHGWVIKENDLFWYGDAEGLSAHGVENVSGHGLYT
13470878   14   ................TSLLGASLSQDN............
17227827   40   PTLTVKDDDLFLVTDTIGNISGCSLSEGNPS....MGLFC
72163378   16   ......GAVTIVEGTSFAISAGDGSMLPDHP....HGVFY
```

```
15616253   34   KDTRFLSKLDLRINGEEPILLNSEAQNAYMASILLTNPHM
89099466   48   KDTRFLSRLDIRINGEEPILLSSDADENYMAKILLTNPHM
RAAC01755  81   RDTRVLSALVWRIEPDVWVALDALAESGSESVYRYTNRPP
13470878   26   ..................VLFTTNLTN...LPIESAAGRQ
17227827   76   CDTRFLNRLELQIDGRSPVLLSSTAEKGFALSVLCTNPRI
72163378   46   DDIRIVSKWEFSVDNQALEPLTVIVHDQPYQAVFLARARR
```

```
15616253   74   EKDGDLILWRESVELERKRFIANDVVYEKIRAKNYFPKPV
89099466   88   EKDGELILWRESVEIERVRFIYEEVLYETVKLKNYFPKEI
RAAC01755 121   RADHEPP..RESLLVERRQRVDGHCFQESGIVRNFGDRAV
13470878   45   IPQ.....GAMHIERVR..LLWEERLYERITLSNYSREHS
17227827  116   DER.....MKADSVSIRRELVLNGALFEEIEVANYSTTTV
72163378   86   GGR......TSNTIFVERERRVGTGMREDITLRNMGREPA
```

```
15616253  114   TFTVNLHFDCDFQDMFVVRGFQHGDVG........KRTGQ
89099466  128   EFNFSLRADADFADMFIVRGFQNGDIG........KRTGQ
RAAC01755 159   RLAVIYEVAADFADMFEVRGFQVEAPA........RAIRS
13470878   78   TILLSLRFAADFRDMFEVRGSTRLKRG........TADTA
17227827  151   AFELSISFDADFVDLFEVRGYNRDKRGKLLRLVEPIAEDG
72163378  120   ACTVTLVVDADFADLFEVKKGEPQNDG.........HYVF
```

```
15616253  146   SVTDN..............EMRFHYEGADEIQRTTLISWD
89099466  160   TCGRQ..............NLSFHYEGADGLERRTRISWD
RAAC01755 191   RVSGN..............VCGFSYSSSDGRTWETRVQLA
13470878  110   EIAGN..............AVVLRYEGLDKVVRTSAISFS
17227827  191   LVDGDGAAVHTQHFAHKEQSLTLAYQGLDGSVMESRIQFQ
72163378  151   RSEGT..............RIIVERWWRGMQRGVIIQAD
```

```
15616253  172   QTA...........QTVSDAGYLDFTCTLGHEESQEIVLT
89099466  186   KEG...........AEVESSGEVSFRFKLQHLEEEAVTFV
RAAC01755 217   AHPSHAGEMTPVRWTESAGVGRAELLITVDAGGAAEWTLT
13470878  136   QT............PDQLTSERADFVIAVTKRSSQTLYVE
17227827  231   HRQ...........PDDFKGYTAIWRLELPSHSTQKLGYR
72163378  176   DAT...........SVAHDRITFRAVVPERGQWSTTVL
```

FIG 14B

```
15616253    201  IAPILNG................EEP.TILPFDVALEQVK
89099466    215  IEPQTGQ................EATKEIQPAEKAKELLR
RAAC01755   257  VRPEVRGGTEFPAAGETGIGLSVSENVSSHPRGNAAEGLR
13470878    164  VGNATDDR...............PESRR.....FRAAAAR
17227827    260  VNMFTNNN...............SSSRVSAAVTLVQAKAS
72163378    203  VRPVVDGE................DLRPRFPKEQPVDESE 15616253    224  ..........ESYRAWNEGVTKVKTDHPRLQRLLDQGIT
89099466    239  ..........DSYQKWNDETTKVETDYEPLQRLVDRGID
RAAC01755   297  SRPARNAEDDASSARGWLNGAPTVS.GHEAFGRWYEQGMR
13470878    184  ........ARFGMRAKRRHGATLHSSGRVFNDWMERARA
17227827    285  ........EMMEEQNWVQKITNIRADKSIFNLVIERAEQ
72163378    227  ........PARRLREWQSNTPVVSTDNDALLAVLRRSQQ 15616253    253  DL...RVLLTDLGYGSFPVAGLPWFAVPFGRDSLIAALQM
89099466    268  DL...RVLLTDLGHGEFPVAGLPWFGVPFGRDSLIAALQM
RAAC01755   336  DI...RMLQSDFGFGPFLVAGVPWYAVPFGRDSLIAARQI
13470878    215  DV...ALLTTELATGPYPYAGIPWFSTAFGRDGVISALQM
17227827    316  DM...YLLRQSFDKYKTVSAGVPWFSALFGRDSLITASQT
72163378    258  DVGALRIFDSRHPQRSIVAAGAPWFMALFGRDSLLTAYMA 15616253    290  LPFQPEVAKGTIRTMAAYQGTKRDPWRDEEPGKIMHELRS
89099466    305  LAFCPEVAKGTLRTMASRQGDKLDPWRDEQPGKIMHELRF
RAAC01755   373  LSAAPEVARGTLATLAHFQGERVDTERDEQPGKILHELRD
13470878    252  LWLNPGLARGVLAFLAQHQATETSPFSDSEPGKIMHETRK
17227827    353  LMLNPEIAKETLMLLAAYQGKHEDEWREEAPGKILHELRL
72163378    298  LPLDPSLALGTLQTLADRQGVEENILTEEEPGRILHESRL 15616253    330  GELANTKQVPFSPYYGTIDATPLYLMLIVEYVKWTGDTTL
89099466    345  GELANTGQIPFTPYYGTIDATPLFLMLLTEYVKWTGDITI
RAAC01755   413  GELARSGKVPFRPYYGSIDATPLFLILLADYWRFTGDTPF
13470878    292  GEMVALSELPFGRYYGVDTTPLYIHLACAYADRTGDTAF
17227827    393  GEMARCQEIPHTPYYGTVDATPLWLMLYSEYYSWTHDRET
72163378    338  GKESGLWLGDGTVYYGTADATPLFVILLGELSRWGADPAE 15616253    370  LEELDSSIEAALRWIDKFGDRDGDGFVEYYQEAAKGIANQ
89099466    385  ADELGENIEAALNWIDEHGDRDGDLFVEYHQESSKGIANQ
RAAC01755   453  LTRMLPHAERALAWMADYGDRDGDGFIEYWREAEGGIANQ
13470878    332  IDTLWPSLCAAAEWIETASRSTG..FLTYQRAAESGLANQ
17227827    433  LEQLWPHALAAMDWIDRNMPSG..YLTYHRKSKRGLDNQ
72163378    378  IEKLLPHADRALEWIERYGDRDGDGFVEYRRRTDQGLVNQ 15616253    410  GWKDSGDSIVHRNGDYAKTPIALAEVQGYVYQAKTGLAEL
89099466    425  GWKDSGDSIVHRNGEYAKTPIALSEVQGYVYQAKRGIASI
RAAC01755   493  GWKDSGDSMVHADGSLAQGPIALAEVQAYAYMAYVAWREI
13470878    370  GWKDSFDSVFHADGRIPKGPIALVEVQGYVFAAFQGLAKL
17227827    471  GWKDSGDCIVDRKGDLANGSIALSEVQAYVYAAKTRLAEI
72163378    418  GWKDSWDGINFADGRIAEAPIALCEVQGYVYAAYLARAYL
```

FIG 14C

```
15616253    450  YEGLNRIDLARKLSEEAQQLSERFEQAFWMEDVGFYAIAL
89099466    465  YEQLGKEAEAVKLRNQAEKLKEKFNEAFWMEDQQFYAIAL
RAAC01755   533  YRELGEPEEAERLARLADGLRSRFLQHFWLEERNEIAMAL
13470878    410  ARLRGEAERAESWEIRADAIRQKVERHFWMEDLGYYALAL
17227827    511  ARMKKRLDLFERWQEEARSLKERFNQDFWIEDQDFCALAL
72163378    458  AHQTGDDQRARYWTERAADLKKAFNERFWQPELGYYAVAL
```

```
15616253    490  DQEKKQVGTITSNPGHLLFSNMLSKERAKQVSDQLVSNKL
89099466    505  DEKKQQVGTITSNPGHTLFSGIVEGERADAVSDMLVSPKM
RAAC01755   573  DGNKRPLCVASSNMGQVLWSDILPSEVAERVAKRLLQPDL
13470878    450  DGDGLPCKVRTSNAGHLLYVGLPGPDRARMVADQLLSASF
17227827    551  DGAGKQVDSITSNPGHCLLLGIFTPERAYSVAERLRAPDM
72163378    498  DHEKKPVDACTSNMGHCLWSGIVDEDKAPYVADRLLSPTM
```

```
15616253    530  FSGYGIRTMAEGEAGYNPMSYHDGSVWPHDNSIILLGMGR
89099466    545  YSGFGVRTMGEGEAGYNPMSYHDGSIWPHDNSMILLGMSK
RAAC01755   613  FSGFGIRTLSAKELRYNPMSYHNGSVWPHDTSLVFAGLVR
13470878    490  HSGWGLRTLADDAIFFNPMSYHNGSIWPHDTAICAAGLAR
17227827    591  FNGWGIRTLSSLSPAYNPMGYHIGSVWPHDNSLIAMGLRS
72163378    538  FSGWGIRTLATDMGAYDPVSYHNGSVWPHDNAIIASGLMR
```

```
15616253    570  LGHHEQANRVINGLIDSASSFEYDRLPELFCGYEKGE..R
89099466    585  LGKTAHASQVMEGLIKASASFEYDRLPELFCGYDASRG.K
RAAC01755   653  HGAWEEAEQIFEGLMRAQAQFPHHRLPELFCGFSREESPR
13470878    530  YGSRDSVVRLMSGTFESAVHFN.MRLPELFCGFTRAAGEA
17227827    631  LGLIDQALEIFQGLLDMTSQQPYQRPPELFCGYERNGDRS
72163378    578  YGFTEHAQRVATALFEAAEHFG.YRLPELFCGFDRTDYPK
```

```
15616253    608  AVKYPVACSPQAWAAGTPLVFIQTILGLEPNVPKGKIFFS
89099466    624  AVKYPVACSPQAWAAGTPLVFIQALLGLFPDSLKEEVRMS
RAAC01755   693  PVPYPVSCSPQAWAAAVPAIVLENLLGLRPDAPRGELTIF
13470878    569  PIAYPVACLPQAWSAGSAFMLQSCLGLQIDGWTGEIHVT
17227827    671  PVQYPVACTPQAWATGSIFQLIQMIVNLVPDAPNNCLRII
72163378    617  PVPYPTSCSPQAWAAATPIHLLRTLLRFDPWVPRGELRLA
```

```
15616253    648  .PSLPDGMKELTVENMKVGKGTISLTLKKKGQQTQLDVMS
89099466    664  .PSLLEGMNKLTVRNIKIGKGLLSLQAARTESGVKLEITE
RAAC01755   733  .PRLPASMQELKVHGLRLGRGKLSVEIARRDGCVLVDVVE
13470878    609  RPRLPIGIDNLVIRHLSVGQAAVDLTFQRVGDRVGAFLAE
17227827    711  DPALPESISRLSLHNLQVGTTVLDLEFERSGGTTACRVAR
72163378    657  .PSLPPGYTRLRIERLPIAGSQLTVDVTGDEVSVEGLPEG
```

```
15616253    687  NTTGLDVQCAS....VISQG
89099466    703  NTTGYQINIH
RAAC01755   772  NTTGLRVDVMDGAKEVMSAS
13470878    649  PHEGLVPLVVRS
17227827    751  .KRGNLRVVIEA
72163378    696  LRLVSEPRELDSLSLVE
```

FIG 15A

```
52081384     1  MAKLDETLMMLKELTDAKGIPANEKEPRQVMKSYIEPFAD
89098880     1  MAKLDETLTMLKELTDAKGIPGNEREVREVMKKYITEFAD
124521982    1  MAKLDETLSMLKDLTDAKGIAGNEAEVRAVVKKYIEPYAD
121533826    1      MDKTLAWLKEISEAPGVSGFEQPIRTLLTQKLSSIA.
RAAC01887    1      MHPHVEVLRDLCDAHGISGYESGVRKLFEERLRPLSE
15615819     1      MNQETQSLFKTLTELQGAPGFEHHIRRFVRGELEKYTN 52081384    41  EVTTDRLGSLIAKKTGQADGPKIMIAGHLDEVGFMVTRID
89098880    41  EVTTDGLGSLVAKKTGKEGGPKIMVAGHLDEVGFMITSID
124521982   41  ELDTDGLGSLIAKKTGQADGPKIMIAGHMDEVGFMVTQID
121533826   37  EVSSDNLGSVIFKKRGGSDTPKIMIAAHMDEIGFMVKYIT
RAAC01887   38  ELLRDRTGGVVGRKTGDPNGPKVLIAGHLDEIGFMVTHIT
15615819    39  EIVQDRLGSIFGVKRGNEQGPKVMVAGHMDEVGFMVTSIN 52081384    81  DRGYLRFQTVGGWWSQVMLAQRVTVVTKKGDITGIIGSKP
89098880    81  DKGFLRFQTVGGWWSQVMLAQRVTIVTSKGDVTGIIGSKP
124521982   81  ESGFLRFQTIGGWWSQVMLAQRVTVVTDKGDVTGVIGSKP
121533826   77  KEGFLKFTTLGGWWEQVMLGQRVTVHTTKGAIPGVIGSKP
RAAC01887   78  SEGFLKFQPIGGWWSQVVLAQRVIVQTRKGPLLGVTGSKP
15615819    79  EKGLIRFQTLGGWWSQVLLAQRVQIMTDEGPVIGVIGSTP 52081384   121  PHVLSQEARKKSVDIKDMFIDIGASSREEAME.WGVLPGD
89098880   121  PHILPPEARKKPVDIKDMFIDIGASSREEAME.WGVKPGD
124521982  121  PHILSPDARKKSYEIKDMFIDIGATSREEALE.WGVKPGD
121533826  117  PHILSPEERKKVVQKKDMYIDIGAEDEKEAKERFGVRPGN
RAAC01887  118  PHILPADERKKVVELKDVFVDIGATSKEHAEE.MGVRPGD
15615819   119  PHLLEEAQRKKPMDVKNMYIDIGADDKEDAQK.IGIKPGQ 52081384   160  QVVPYFEFTVMNNEKMLLAKAWDNRIGCAIAIDVLKNLKG
89098880   160  MAVPYFEFTVMNNEKMLLAKAWDNRIGCAIAIDVLKQLKD
124521982  160  MVVPYFEFTVMKNEKMLLAKAWDNRIGCAVVIDVLKNLHK
121533826  157  PVTPFSPFTTLANERLLMGKAWDNRIGCAIMAEVMEKLQH
RAAC01887  157  AIVPYSPFTQLGNPKMYVSKALDNRLGCATALCVLKELQG
15615819   158  QIVPICPFTPLANEKKIMAKAWDNRYGVGLAIELLKELQG 52081384   200  ADHPNVVYGVGTVQEEVGLRGAKTAAHTIKPDIAFGVDVG
89098880   200  AEHPNVVYGVGTVQEEVGLRGAKTAANLIEPDIGFGVDVG
124521982  200  ENHPNIVYGVTNVQEEVGLRGAKTAASKVKPDIAFALDVG
121533826  197  EMHANTVYGVGTVQEEVGLRGAKTSAGVIHPDIAFAVDTC
RAAC01887  197  QAHPNIVFAGATAQEEVGLRGAKTLVHLVDPDIAISIDVG
15615819   198  ETTPNILYSGATVQEEVGLRGAATSAQMIEPDIFYALDAS 52081384   240  IAGDTPGIT..EKESASKMGKGPQIILYDASMVSHKGLRD
89098880   240  IAGDTPGIS..EKEALSKMGKGPQIILYDASLVSHKGLRD
124521982  240  IAGDTPGIS..EKEALSKMGKGPQIVIYDASMVAHKGLRD
121533826  237  VAGDTPGVT..SDQASSKLGKVAISIYDSSLIPHTGLRD
RAAC01887  237  VAGDTPGIESGERQHLGDAKGPLLMIYDHSMIPNNRFRD
15615819   238  PANDATAGK....DAFGQLGKGALVRIYDRTMVTHRGIRD
```

FIG 15B

```
52081384    278  FVTNVADEAGIPYQFDALSGGGTDSGSIHLTANGVPALSI
89098880    278  LVTDTADEMNIPYQFDSIAGGGADSGAIHLSHNGVPSLAI
124521982   278  TVVKVAEELNIPYQFESIPGGGTDAGSIHLTGSGIPSLAI
121533826   275  FVVEVAEQNHIPYQLEFTEGGGTDAGRIHLHAQGVPSLVL
RAAC01887   277  FVLDIAATENIPVQLSSLAGGGTDAGSFHLHGIGVPSVNI
15615819    274  FVLDTAETENIPYQF.FISQGGTDAGRVHLSGNGVPSAVI 52081384    318  TIATRYIHTHAAMLHRDDYEHAVKLITEVIKRLDKETVQN
89098880    318  TIATRYIHSHAAMLHRDDYENAVKLIVEVIKRLDKETVDR
124521982   318  TIATRYIHSHAGILHRDDYENTVKLITEVIKRLDRKTVNH
121533826   315  SIPTRYIHSHNSIVHRDDYDAAVRLLVAVIKQLDQNKYQE
RAAC01887   317  GFATRYIHSHNGVVHEDDYLQAIRLVTAMVKALDKDMVTE
15615819    313  GICSRYIHTAASIIHVDDYAAAKALLVKLVKTTDKAAVET 52081384    358  ITFD
89098880    358  ITFD
124521982   358  IIFD
121533826   355  LVK
RAAC01887   357  IQAW
15615819    353  ILANG
```

FIG 16A

```
13470513     1                                    MMTIHPLSPEDAPALAA
21221842
13471782     1                                    MASIESEANRN..HYAA
RAAC01897    1                                    MPSLQALSVRS..MLQQ
16329563     1  MVYAPRPLPSRSLPVPASVSPALKKAIAQSLQGAMEAIKN
15600577     1                                    MAAKYPLSPAMWRFVEH
```

```
13470513    18  MRQAASAHKGEKLGPEARPMFDAMFAATPAAADVQVEAAT
21221842     1                                          MVSRRTV
13471782    16  IG..ANAGKLSPQAFVEFNDSSWTALTG.EPGGVDYIEVD
RAAC01897   16  MR..ASQNLAEQSLEVQRAGLDQMGRTIPKPENVKVERTS
16329563    41  IPPLEDKPAWQTLIAAYDQASQVLWQKLRQQFPVTLTKKS
15600577    18  SRAFASDSPRLDAQRAAYAR.MCQAFAPPRPAGLRVLDSC
```

```
13470513    58  AGGIAGFWLRP......VSARSGAHILYLHGGGYVLGSAG
21221842     8  LGGRPALELAP......DTASGPGRLLYLHGGGYLAGSPD
13471782    53  AGGVPGLWVVP......KGADERRVLFYAHGGGFLGGSIY
RAAC01897   54  FGGVPGEWIAM......ADEPTARVILYLHGGAYYMGSCE
16329563    81  IAGVNVYRVTPPII...SPENSQRIWVHLHGGGYALAGGE
15600577    57  LPAAPPVRVRRYRPDRPAPPGGWPALLYLHGGGWMLGGLD
```

```
13470513    92  ALTNFAGQIASRVGADTFVPDYRLAPEHPFPAAIDDAVAA
21221842    42  THAGLAGELARRAGLRAVSVDYRLAPEHPFPAAVDDGLAA
13471782    87  THRKLVGHLAKAVGCRALLYGYPLASQAKYPAQLEAAMAA
RAAC01897   88  SHRSLAWRLAQASGSRVALIEYRLAPEHKFPATVEDAVKA
16329563   118  LGTGEAVLAAHYGQVGVISIDYRQPPNYPFPAALEDALVM
15600577    97  SHDFICADLAARLGLLVLAVDYRLAPEHPFPAALQDCLRA
```

```
13470513   132  YRGL....VADGAER..IVVVGDSAGGGLTLSLLSALAAD
21221842    82  YREL....LSTGTDPQDLVLAGDSAGGGLG...IATLLAA
13471782   127  WDWL....IDQDFDTRRIALAADSCGAVLT...YGVLQRL
RAAC01897  128  YESL....LAQGIAPDRIAIAGDSAGGGLT...MATLISL
16329563   158  WQEL....VKT.HDVNRLALFGTSAGGGLL...LALVCQL
15600577   137  WQALSLGELDEALDGRRLLVAGDSAGGNLA...AALCLAL
```

```
13470513   166  KTNGMVQPVGAAVMSPWTDLALTGDSLGTRAEAD..PIFT
21221842   115  REAGLPQPAAVALFSPWVDLTLTGGSIRSKEGAD..PIFT
13471782   160  RAQERPLPAATLIISGWFDMALTAASYETNREKD..PFFA
RAAC01897  161  RDAGKPLPACAALLSPWTDLAGTGPSMESRAAHD..PWLD
16329563   190  RQLNLPLPAAIAPLSPWVDLKTGDTHFTNEYVDRTAISY
15600577   174  RDGGAPSPAAQILLYPLLSAAPS....PSRIDCADAPLLG
```

```
13470513   204  GGVLQGFADMYLQGQDAK.NPKASPLYA.RLNGLPPIRID
21221842   153  EADVRAYADLYVGAGDRA.APLASPVFA.DLAGLPPLLVQ
13471782   198  KGGVDWLVTSFIGDYDRL.DPEVSPLYA.DLSGFPPVFLQ
RAAC01897  199  PEGIRKAPLLYCSAEQLT.HPLVSPLYA.DLAGLPPILIH
16329563   230  DGLIEGLARLYAGELPLT.HPLISPIYN.DLAGLPPTLLI
15600577   210  LGDVQACLDAYLPLAALHRQPLALPLEAADFTGLPPAFVA
```

FIG 16B

```
13470513    242  VGDDELLLADSVRYADRARAAGVEVTLSVWQGMPH..VFQ
21221842    191  AGANEVLLDDAVRLAGRAGADDVEVTLEVGPGLPH..VYQ
13471782    236  AGADETLVDESRMFAERARQAGVETRLDIFDDMLH..SFQ
RAAC01897   237  VGHDECLLDDSVRLHEKLRQAGVDARLHVWEDMWH..VFH
16329563    268  SGTRDLLLSDTARLQRKLRQNKVPVDLQLFEGLSH..AEY
15600577    250  VAEFDPLRDDGERYGAALRAAGGEAGFYPGSGLVHGCLRG
```

```
13470513    280  SSLGHFLAAERSVDAIVD.FLRQRLVGTSPSNSTASEA
21221842    229  LHYGRLEEADAALDRAAR.FLTAHLGAGHPDAGRLAPVR
13471782    274  MMAGRAPEADDAIGRLAA.WVRPRLGLPDAGDNAVSDKVA
RAAC01897   275  SFP..IPEADEALKEIGD.FMKEKIPD
16329563    306  LYEFDTPESAEVFRELSQ.FFNRHLQK
15600577    290  HGIDEVEALHEALRRAVQGFLAEDSGERQAGEESTAEHQP
```

```
13470513
21221842
13471782    313  GRAA
RAAC01897
16329563
15600577    330  GE
```

FIG 17A

```
39654242     1          MNSSLPSLRDVFANDFRIGAAVNPVTIEMQKQ
61287936     1          MPTEIPSLHAAYANTFKIGAAVHTRMLQSEGE
3201483      1          MSTEIPSLSASYANSFKIGAAVHTRMLQTEGE
134266943    1         MSVSQSLPSLREVFANDFRIGAAVNPVTIESQKQ
RAAC01917    1           MTDQAPSLKEAYASRFRVGAAVNAATVHTHAH
114054545    1  MVGGGGMKMNSSLPSLRDVFANDFRIGAAVNPVTIEMQKQ 39654242    33  LLIDHVNSITAENHMKFEHLQPEEGKFTFQEADRIVDFAC
61287936    33  FIAKHFNSITAENQMKFEEIHPEEDRYSFEAADQIVDFAV
3201483     33  FIAKHYNSVTAENQMKFEEVHPREHEYTFEAADEIVDFAV
134266943   35  LLISHVNSLTAENHMKFEHLQPEEGRFTFDIADRIVDFAR
RAAC01917   33  LLARHFSSVTPENEMKWERIHPAEDTYSFSAADQIVLFAR
114054545   41  LLIDHVNSITAENHMKFEHLQPEEGKFTFQEADRIVDFAC 39654242    73  SHRMAVRGHTLVWHNQTPDWVFQDGQGHFVSRDVLLERMK
61287936    73  AQGIGVRGHTLVWHNQTSKWVFEDTSGAPASRELLLSRLK
3201483     73  ARGIGVRGHTLVWHNQTPAWMFEDASGGTASREMMLSRLK
134266943   75  SHHMAVRGHTLVWHNQTPDWVFQDGQGHFISRDVLLERMK
RAAC01917   73  DHGMFVRGHTLVWHNQTPSWVFLDSLGQPAPAKLVEARLE
114054545   81  SHRMAVRGHTLVWHNQTPDWVFQDGQGHFVSRDVLLERMK 39654242   113  CHISTVVRRYKGKIYCWDVINEAVADEGDELLRPSKWRQI
61287936   113  QHIDTVVGRYKGQIYAWDVVNEAVEDKTDLFMRDTKWLEL
3201483    113  QHIDTVVGRYKDQIYAWDVVNEAIEDKTDLIMRDTKWLRL
134266943  115  SHISAVVRRYKGKVYCWDVVNEAVADEGSEWLRSSKWRQI
RAAC01917  113  QHIAEVVGHYRGAALCWDVVNEAVIDQGDGWLRPSPWRQA
114054545  121  CHISTVVRRYKGKIYCWDVINEAVADEGNELLRPSKWRQI 39654242   153  IGDDFMEQAFLYAYEADPDALLFYNDYNECFPEKREKIFA
61287936   153  VGEDYLLQAFSMAHEADPNALLFYNDYNETDPVKREKIYN
3201483    153  LGEDYLVQAFNMAHEADPNALLFYNDYNETDPVKREKIYN
134266943  155  IGDDFIEQAFLCAHEADPDALLFYNDYNECFPKKREKIYT
RAAC01917  153  LGDDYIEMAFRLAHQADPGALLFYNDYNETKPDKRDRILR
114054545  161  IGDDFMEQAFLYAYEADPDALLFYNDYNECFPEKREKIFA 39654242   193  LVKSLRDKGIPIHGIGMQAHWSLTRPSLDEIRAAIERYAS
61287936   193  LVRSLLDKGAPVHGIGLQGHWNIHGPSIEEIRMAIERYAS
3201483    193  LVRSLLDQGAPVHGIGMQGHWNIHGPSMDEIRQAIERYAS
134266943  195  LVKSLRDKGIPIHGIGMQAHWSLTRPSLDEIRAAIERYAS
RAAC01917  193  LLEHLLDRGVPVHGVGLQMHVSLDDPPIEEMEEAIERYRA
114054545  201  LVKSLRDKGIPIHGIGMQAHWSLTRPSLDEIRAAIERYAS 39654242   233  LGVVLHITELDVSMFEFHDRRTDLAAPT....SEMIERQA
61287936   233  LDVQLHVTELDMSVFRHEDRRTDLTAPT....SEMAELQE
3201483    233  LDVQLHVTELDLSVFRHEDQRTDLTEPT....AEMAELQQ
134266943  235  LDVVLHITELDVSMFEFHDHRKDLAAPT....NEMIERQA
RAAC01917  233  LGLRLHVTELDVSVYPWVHEPDRPQAPARPYDDELAERLA
114054545  241  LGVVLHITELDVSMFEFHDRRTDLAAPT....SEMIERQA
```

FIG 17B

| | | |
|---|---|---|
| 39654242 | 269 | ERYGQIFALFKEYRDVIQSVTFWGIADDHTWLDNFPVHGR |
| 61287936 | 269 | LRYEEIFNLFREYKSSITSVTFWGVADNYTWLDHFPVRGR |
| 3201483 | 269 | KRYEDIFGLFREYRSNITSVTFWGVADNYTWLDNFPVRGR |
| 134266943 | 271 | ERYEQIFTLFKEYRDVIESVTFWGMADDYTWLDHFPVQGR |
| RAAC01917 | 273 | ARYEALFALYLRHQDAIDNVTLWGVADDSTWRDDFPVKGR |
| 114054545 | 277 | ERYGQIFALFKEYRDVIQSVTFWGIADDHTWLDNFPVHGR |

| | | |
|---|---|---|
| 39654242 | 309 | KNWPLLFDEQHKPKPAFWRAVSV |
| 61287936 | 309 | KNWPFVFDQQLQPKVSFWRIINSMS |
| 3201483 | 309 | KNWPFVFDTELQPKDSFWRIIGQD |
| 134266943 | 311 | KNWPFLFDEQHEPKSAFWRVASI |
| RAAC01917 | 313 | KDWPLLFDVHHRPKEAFWRVVRLAQN |
| 114054545 | 317 | KNWPLLFDEQHKPKPAFWRAVSV |

FIG 18A

| | | |
|---|---|---|
| RAAC02404 | 1 | MRKLSHSGKSMAIPPRERVGMQRAVELEVDGLVLRGMEHV |
| 58338090 | 1 | MSR.ITIERDGLTLVGDR.. |
| 76796576 | 1 | MQKAVEITYNGKTLRGMMHL |
| 114845181 | 1 | MQKHVEFTYNGKTLRGMMHL |
| 15896898 | 1 | MWGKIIMQKSVEIKSKSLTLRGVLHM |
| 15806073 | 1 | MEMFAQFSVEGQRMYGMLHT |

| | | |
|---|---|---|
| RAAC02404 | 41 | P......DEAANRPVPAAILFHGFTGTHIEPHQLFVKLSR |
| 58338090 | 18 | .......EEPFGEIYDMAILMHGFTANRNTP..LLRQIAD |
| 76796576 | 21 | P......DDVKGK.VPMVIMFHGFTGNKVESHFIFVKMSR |
| 114845181 | 21 | P......DGIHGK.VPMVAIFHGFTGNKMEPHFIFVKLSR |
| 15896898 | 27 | P......LEAREK.LPIVVIYHGFCGNKMGPHFIFVKLAR |
| 15806073 | 21 | PDGSATGQQAPPQGWPSVVIVHGFTGDKVSSHRLLVLLAR |

| | | |
|---|---|---|
| RAAC02404 | 75 | ALEAEGVAAFRFDFAGSGDSDGEFQDMTASSEIRDAKAIL |
| 58338090 | 49 | NLRDENVASVRFDFNGHGESDGAFEDMTVCNEIADAQKIL |
| 76796576 | 54 | ALEKVGIGSVRFDFYGSGESDGDFSEMTFSSELEDARQIL |
| 114845181 | 54 | QLEKVGIGSVRFDFYGSGESDGDFSEMTFSGELEDARQII |
| 15896898 | 60 | ELEKLGIATIRFDFAGTGESDGEFVDMTFSNEVYDANVIL |
| 15806073 | 61 | RLTAAGIAALRFDCRGSGESQGDFSEMTVGREVQDVEAAF |

| | | |
|---|---|---|
| RAAC02404 | 115 | DWVRRDPRIDPDRVSLIGLSMGGYVASIVAGDEPDKVDRL |
| 58338090 | 89 | EYVRTDPHVR..NIFLVGHSQGGVVASMLAGLYPDIVKKV |
| 76796576 | 94 | KFVKEQPTTDPERIGLLGLSMGGAIAGIVAREYKDEIKAL |
| 114845181 | 94 | KFIKNEPMADVENIGILGLSMGGAVAGVIASELKEEIKAL |
| 15896898 | 100 | DYVKTLEFVDKDRISILGFSMGGAIASVIAGDRKDEINTL |
| 15806073 | 101 | DYVRHQPGLDPERVMLLGYSMGGLVSALAAEKVRP..HRF |

| | | |
|---|---|---|
| RAAC02404 | 155 | VLLAPAGNMADIAEK.....QAEALGAAADADVVDLGGNL |
| 58338090 | 127 | VLLAPAAQLKDDALNGD..TQGATYNPEHIPAAIPFHGKK |
| 76796576 | 134 | VLWAPAFNMPELIMHES...VKQYGAIMEQLGFVDIGGHK |
| 114845181 | 134 | ALWAPAFNMPELILEQSKSADEKMLGMLEREGIIDIGGLA |
| 15896898 | 140 | CLWAPAGNMEQIILSDT.YIGDKYDEIMEK.GIYDVEGLL |
| 15806073 | 139 | ALWSPALPELWLRHLRG.........GLLPPVISDYGGWP |

| | | |
|---|---|---|
| RAAC02404 | 190 | VGRGLYEDLKQIDAFERAKPFRGKVLIIHGMEDQAVPYEV |
| 58338090 | 165 | LGGFYLRTAQVLPIYEIAKHYTNPVSIIVGSNDQVVAPKY |
| 76796576 | 171 | LSKDFVEDISKLNIFELSKGYDKKVLIVHGTNDEAVEYKV |
| 114845181 | 174 | LSKEFIDDLIKLNIFEFSKGYDKPVLIVHGTEDAAVKYEV |
| 15896898 | 178 | LGKKFLEDIKKVNIFDRASAYNKQSLIIHGTSDEIVPLST |
| 15806073 | 170 | LGRAFLQEVVQTRPLEAAARWGGVAHVFHGDRDQTCPVEW |

| | | |
|---|---|---|
| RAAC02404 | 230 | SLKYQNEVYGERARLHLIEEADHTFNNRHWESEVIRETVR |
| 58338090 | 205 | SKKYD.EVY.ENSELHMVPDADHSFTG.QYKDSAVDLTAE |
| 76796576 | 211 | SDRILKEVYGDNATRVTIENADHTFKSLEWEKKAIEESVE |
| 114845181 | 214 | SDKILEEVYRGNAKRITIEGADHTFNKLEWEKKAIEESIN |
| 15896898 | 218 | SERYL.EMYGENTSLELVEGANHIFEKNSWENRVIDLTKK |
| 15806073 | 210 | GVRTPKPCAATPPRFPARGTRMTRSNR |

FIG 18B

```
RAAC02404    270  FLTDVDRSQ
58338090     242  FLKPLF
76796576     251  FFKKELLKG
114845181    254  FFK.ENLKG
15896898     257  YFSGKLVKF
15806073
```

FIG 19A

| | | |
|---|---|---|
| 124521931 | 1 | MKTAIVETVFGKARGYEEKGVQIWKGIPYAKPPIGPLRFR |
| 33311865 | 1 | MTKTIVGSVYGKLQGEQVDGVCSWKGVPYAKPPVGALRFR |
| 134105165 | 1 | MERTVVETRYGRLRGEMNEGVFVWKGIPYAKAPVGERRFL |
| 56421584 | 1 | MERTVVETRYGRLRGVVNGSVFVWKGIPYAKAPVGERRFL |
| 138896639 | 1 | MGTVIVETKYGRLRGGTNEGVFYWKGIPYAKAPVGERRFL |
| RAAC02424 | 1 | MDVIVETRYGKVMGREEDGVRVFLGVPYAKAPQGERRFL |

| | | |
|---|---|---|
| 124521931 | 41 | PPELPEPWAGVKDCTQFGPIAWQPPVELMD.FLGNPAENM |
| 33311865 | 41 | APERPDSWEGVRQATSFSPVAPQTQREIME.FFGNDISNM |
| 134105165 | 41 | PPEPPDAWDGVREATSFGPVVMQPSDPIFSGLLGRMSEAP |
| 56421584 | 41 | PPEPPDAWDGVREAAAFGPVVMQPSDPIFSGLLGRMSEAP |
| 138896639 | 41 | PPEPPDAWDGVREATSFGPVVMQPSDSMFSQLLGRMNEPM |
| RAAC02424 | 40 | PPEPVEPWADVLDARAHGPICPQVANPLNP....VDGFVQ |

| | | |
|---|---|---|
| 124521931 | 80 | DEDCLNLNIWTPGADGERRPVMVWIHGGAFANGAGSAPSY |
| 33311865 | 80 | NEDCLYLNVWSPGADDKKRPVMVWIHGGAFVSGSGSSSWY |
| 134105165 | 81 | SEDGLYLNIWSPAADGKKRPVLFWIHGGAFLFGSGSSPWY |
| 56421584 | 81 | SEDGLYLNIWSPAADGKKRPVLFWIHGGAFLFGSGSSPWY |
| 138896639 | 81 | SEDGLYLNIWSPAADGKKRPVLFWIHGGAFLFGSGSFPWY |
| RAAC02424 | 76 | SEDCLRLNIYAP.AEGTGHPVMVWIHGGAFVFGSGQSPWY |

| | | |
|---|---|---|
| 124521931 | 120 | DGSAFAKNGDVVVVTINYRLGALGFLYLGEMGG.EYEASG |
| 33311865 | 120 | DGASFAAQGDVVVVTINYRLGILGFLHLGEIGGEEYATSG |
| 134105165 | 121 | DGTAFAKHGDVVVVTINYRMNVFGFLHLGDSFGEAYAQAG |
| 56421584 | 121 | DGTALAKHGDVVVVTINYRMNVFGFLHLGDLFGEAYAQAG |
| 138896639 | 121 | DGTAFAKHGDVVVVTINYRMSVFGFLYLGDAFGETYAQAG |
| RAAC02424 | 115 | DGRAFARDG.VVLVSINYRLGPLGFLHLAHLGGEAYASSG |

| | | |
|---|---|---|
| 124521931 | 159 | NCGILDQIAALKWVKENIAAFGGDPDCVTIFGESAGAMSV |
| 33311865 | 160 | NCGILDQVAALQWVQENIASFGGDPNNVTVFGESAGAMSI |
| 134105165 | 161 | NLGILDQVAALRWVKENIAAFGGDPDNITIFGESAGAASV |
| 56421584 | 161 | NLGILDQVAALRWVKENIEAFGGDPDNITIFGESAGAASV |
| 138896639 | 161 | NLGILDQVAALRWVKENIEAFGGDPDNITIFGESAGAASV |
| RAAC02424 | 154 | NAGILDQVAALTFVRDTIEAFGGDPNRVTVAGESAGAWSV |

| | | |
|---|---|---|
| 124521931 | 199 | AALLSSPAASGLFHKAILESG.AANFTATPERAAKNARRI |
| 33311865 | 200 | GVLLGFPSAQGLFHNAILQSG.AAANVHSSETATKVAGHL |
| 134105165 | 201 | GVLLSLPEASGLFRRAMLQSGSGSLLLRSPETAMAMTERI |
| 56421584 | 201 | GVLLSLSEASGLFRRAILQSGSGALLLRSPKTAMAMTERI |
| 138896639 | 201 | GVLLSLPEASGLFRRAILQSGSGSLLLRSPETAMALTERI |
| RAAC02424 | 194 | GTLLVMESARGLFQQAILQSG.IPFAYRTPEFAEWWTTQL |

| | | |
|---|---|---|
| 124521931 | 238 | LETLGLEKKDVAKLAEVPAKNLAEAVNSL...PFMSLLPV |
| 33311865 | 239 | LAALQVEPTNLSKLEELSVEQLIQVADLV...PPMSLGPV |
| 134105165 | 241 | LDKAGIRPGDRERLLSIPAEELLRAALSLG..PGVMYGPV |
| 56421584 | 241 | LERAGIRPGDRGRLLSIPAEELLRSALSLG..PGIMYGPV |
| 138896639 | 241 | LERAGIRPGDRDRLLSIPAAELLQAAMSLG..PGITYGPV |
| RAAC02424 | 233 | LDALGINQASWHRLFDVPAADLVAAAARIPARDGLNLRPV |

FIG 19B

```
124521931    275  TDGIVLPEHPERALEN.AAKDIPVLIGTNKDEYRLFTVFD
33311865     276  IDGVSLPKHPQEAIADGSAKDVSILVGTNKDEYNIFSVFD
134105165    279  VDGRVLRRHPIEALRYGAASGIPILIGVTKDEYNLFTLTD
56421584     279  VDGRVLRRHPIEALCDGAASGIPILIGVTKDEYNLFTLTD
138896639    279  VDGHVLRRHPIEALHDGAASDIPILIGVTKDEYNLFSLTD
RAAC02424    273  LDGVTLTRSFWDALREGQAAHVPTLAGSNREELMLWMARD 124521931    314  PVWKRQDPKEMQDVFQKTFAKYWDALS...AKITDPSAFT
33311865     316  PEWKNADEAKVTALFEKTFGPLVQVIS...KFIPG..GLN
134105165    319  PSWTKLGEKELLDRINREVGPVPEEAIRYYKETAEPSAPT
56421584     319  PSWMKLGEHELLDRINREVGPVPEAAIRYYAETAEPSAPD
138896639    319  PSLTRLEEKELLDRMNREVGPIPEEAVRYYAETADRSAPA
RAAC02424    313  PEWRTLSDEERIARVDRMWGPLGDRAR..DYYVDGRTGDE 124521931    351  QELYDR.IMTYFVFTGPALKLADTRAQTGEKVWMYQFDWE
33311865     351  QDLFNK.LLTDTIFTNPAQKLAELQVNQGTPVWMYRFDWE
134105165    359  WQTWLR.IMTYRVFVEGMLRTADAQAAQGADVYMYRFDYE
56421584     359  WQTWLR.IMTYRVFVEGMLRTADAQAAHGADVYMYRFDYE
138896639    359  WQTWLR.IMTYLVFVDGMLRTADAQAAQGANVYMYRFDYE
RAAC02424    351  LETWLVRFASMRSFTYPTIRAAEIQSEY.APVYLYRFDYR 124521931    390  SPVYNGTLKACHALEIPFVWHTLEQPGTENLTGNAPGRHA
33311865     390  TPVFGGALKSTHALEIPFVFNTLRTPNTENFTGSSPERQQ
134105165    398  TPVFGGQLKACHALELPFVFHNLHQPGVANFVGNRPEREA
56421584     398  TPVFGGQLKACHALELPFVFHNLHQPGVANFVGNRPEREA
138896639    398  TPAFGGQLKACHTLELPFVFHNLHQPGVENFVGNRPEREA
RAAC02424    390  P....SQLGAAHALEIPFVFGTYAHPSARVLVGDRPSHAA 124521931    430  LADQMHQAWIAFAQNGDPNCSLLPE.WPPYNTRQRPAMIF
33311865     430  IADQMHQRWINFAKSGHPNSDRLLE.WPSYDMNNRSTMIF
134105165    438  IANEMHYAWLSFARTGDPNGAHLPEAWPAYTNERKAAFVF
56421584     438  IANEMHYAWLSFARTGDPNGAHLPEKWPIYTNERKPVFVF
138896639    438  IASEMHGAWLSFARTGNPNGAHLPEKWPVYTKEHKPVFVF
RAAC02424    426  VSDAMHAAWVAFVRHGSPQAPHLPE.WPTYDPKRRSTMIF 124521931    469  GQDCRVEKDPHQAERALWGGLGE
33311865     469  NNESIVVNDPNREDRLKWEQLSMVMKG
134105165    478  SAASHVEDDPFGRERAAWQGR
56421584     478  SAASHVEDDPFGCERAAWMTRA
138896639    478  SAASHVEDDPFGREREAWQGRL
RAAC02424    465  DETSRVEEDPDTAERELWSEMMSLSM
```

FIG 20A

| | | |
|---|---|---|
| 29377189 | 1 | MKTWENYKVDSINRLPGRAHFSSFPSK |
| 116493950 | 1 | MTTAKLWEKPELTDINRMAPRSHFQTFFP. |
| 40745013 | 1 | MASLSAVSGWPTYLPDWSNLNVLHRNTLPPRAHFYSYPNE |
| RAAC02616 | 1 | MEVMRVEQKYVESFYPPSDY......RLPPRAFFIPHSTE |
| 49176308 | 1 | MNRWENIQLTHENRLAPRAYFFSYDSV |

| | | |
|---|---|---|
| 29377189 | 28 | ETALL.NENKYTQAYKNLNGCWHFLFLEAPEYSPENFFAT |
| 116493950 | 30 | ......GENRQPRHYQLLNGTWQFKFLDAPEYAPEDFMAV |
| 40745013 | 41 | EAALT..FNRDEGLFQSLNGTWKFHYDASPFEAP...IWN |
| RAAC02616 | 35 | REALARGFYRASTQVLPLEGKWKFRLFDNPRAVPTDVTWI |
| 49176308 | 28 | AQART.FARETSSLFLPLSGQWNFHFFDHPLQVPEAFTSE |

| | | |
|---|---|---|
| 29377189 | 67 | DFDTSQMDQITVPGNWQVQGYGKMHYSDLWYNFPINPPYV |
| 116493950 | 64 | DFNDQDWDQIPVPSNWQLQGYGKMHYSDLWYNFPINPPFV |
| 40745013 | 76 | TANTTEWDDIIVPGVWQMQGYGRPQYTNIHYPIPVTPPNV |
| RAAC02616 | 75 | DFDDSSWEEIHVPSNWQMEGYGRPHYTNVMYPFPVDPPRV |
| 49176308 | 67 | LMAD..WGHITVPAMWQMEGHGKLQYTDEGFPFPIDVPFV |

| | | |
|---|---|---|
| 29377189 | 107 | PTENPTGIYKRTFAIDETFHDKKIILRFCGVDSAYHVWVN |
| 116493950 | 104 | PSENPTGLYRRTFTVDEVAVNEQYIIGFDGADSAFKLYLN |
| 40745013 | 116 | SYMNPTGSYWREFDVPADWGQQIRLRYEGVDSAFHVWVN |
| RAAC02616 | 115 | PSENPTGCYRTKFFLTHHDVG.RVHLRFEGVDGLYQVYVN |
| 49176308 | 105 | PSDNPTGAYQRIFTLSDGWQGKQTLIKFDGVETYFEVYVN |

| | | |
|---|---|---|
| 29377189 | 147 | GHEVGYSKGARNEAEFDITPYAKIGETNDLTVRVYQWSDG |
| 116493950 | 144 | GDFIGCSKGARLPSEFDVTKALKQG.TNTIAVEVVQWSDG |
| 40745013 | 156 | GEEVGYSQGSRNPSEFDITGYLSSEGTNTLATRVYQWSDG |
| RAAC02616 | 154 | GHDIGFGYGSRLPSEFDITDFVHA.GDNVLVVVVCQWSAQ |
| 49176308 | 145 | GQYVGFSKGSRLTAEFDISAMVKTG.DNLLCVRVMQWADS |

| | | |
|---|---|---|
| 29377189 | 187 | TYLEDQDMWWLSGIFRDVELLGVPENGLEDFFIISDLDDS |
| 116493950 | 183 | TYLEDQDMWWLSGLFRDVSLYRPQNGLYDVRVRTYLLKD |
| 40745013 | 196 | TYLEDQDQWWLSGIFRDVYLVPFPSSAITDFFIQPEVDDG |
| RAAC02616 | 193 | SYLEDQDMWWLSGIFRDVYILKRPQIYLSDVRVRALLGTD |
| 49176308 | 184 | TYVEDQDMWWSAGIFRDVYLVGKHLTHINDFTVRTDFDEA |

| | | |
|---|---|---|
| 29377189 | 227 | YQNGHLAITGKFWQDKGQQ....VQLELMD...QQGKTVL |
| 116493950 | 223 | YRAGELVVTPTLSGAVPSK....IHYELT....KDGATLI |
| 40745013 | 236 | FASGTLKVNVTIQGEHGN.....LSVKVLS...PGGN.VV |
| RAAC02616 | 233 | GRTGCLHVEVEIGGILSRDKPVPLRFKLID...SIGDSEI |
| 49176308 | 224 | YCDATLSCEVVLENLAASPVVTTLEYTLFDGERVVHSSAI |

| | | |
|---|---|---|
| 29377189 | 260 | KETVAGNQGTVEFSASLPSVTAWSAEKPYLYQLFITVFSE |
| 116493950 | 255 | DQTLSTD...VSLDVTLNDIQAWSAEAPNLYDLTMTVLQN |
| 40745013 | 267 | DEWTGSSSTIYSKDIKGDDFLLWSAETPNLYTVLIEFN.. |
| RAAC02616 | 270 | LENTMLSDGFATYEAEIPNVRPWTAETPNLYTLLVSIDPD |
| 49176308 | 264 | DHLAIEKLTSASFAFTVEQPQQWSAESPYLYHLVMTLKDA |

FIG 20B

| | | |
|---|---|---|
| 29377189 | 300 | .GEVVEVIPQKVGFRNIHVSGETFLVNGVAIKLKGMNRHD |
| 116493950 | 292 | .DAPLEVVRQRIGFRQIELNGKTFLVNGKAIKFKGVNMHD |
| 40745013 | 305 | ....GRTISQKVGFRRVEMSGSNFLVNGQPIIIYGVNRHE |
| RAAC02616 | 310 | .SLYAEHVALQVGFRRIEIADGQLKINGVPIVLKGVNRHE |
| 49176308 | 304 | NGNVLEVVPQRVGFRDIKVRDGLFWINNRYVMLHGVNRHD |

| | | |
|---|---|---|
| 29377189 | 339 | YNPKNGRVVSREEIEKDIRLMKQFNINAIRTSHYPASAYF |
| 116493950 | 331 | YSATEGRVMSEADFKKNIISMKRNNINAIRTAHYPKAPYF |
| 40745013 | 341 | HNYTSGRTVPYESMRADLIRMKQSNINAIRTAHYPQHPSF |
| RAAC02616 | 349 | HDARLGRALTLDVMIRDVQMMKQNNINAVRTSHYPHHPVF |
| 49176308 | 344 | NDHRKGRAVGMDRVEKDLQLMKQHNINSVRTAHYPNDPRF |

| | | |
|---|---|---|
| 29377189 | 379 | YDLCDEYGMYVIDETDLECHGFELTGEYDW.....ISNDP |
| 116493950 | 371 | YDLCDELGMYVIDETDLECHGFELTERYDW.....ITDDP |
| 40745013 | 381 | YDVADELGFYVITEADLECHGFRDIAGSEENAAAWTSDNP |
| RAAC02616 | 389 | YDLCDRYGLYVLDEADLECHGFALTGNWDR.....LSDDP |
| 49176308 | 384 | YELCDIYGLFVMAETDVESHGFANVGDISR.....ITDDP |

| | | |
|---|---|---|
| 29377189 | 414 | EWETAYVSRMVRMIQRDKNHPSILFWSLGNESAFGHNFIE |
| 116493950 | 406 | RWKTAYVDRMRRTLQRDKNHPAIIMWSLGNESDFGDNFRA |
| 40745013 | 421 | EWTHAYLDRAEQLVERYKNHPSVIMWSLGNECQYGQNQAA |
| RAAC02616 | 424 | QLEQAYVDRLERMICRDRNHACVIMWSLGNESGYGRNHRA |
| 49176308 | 419 | QWEKVYVERIVRHIHAQKNHPSIIIWSLGNESGYGCNIRA |

| | | |
|---|---|---|
| 29377189 | 454 | MARIAKEMDPTRLVHYEGDFE..........AEVTDVYST |
| 116493950 | 446 | MAAYCKAEDPTRLVHYEGDFE..........AEVSDVYST |
| 40745013 | 461 | MYKWIKERDPSRLVHYEQDHN..........AETADIYSQ |
| RAAC02616 | 464 | MAERARAIDPTRPVHYEGETRRLLELGSDLQHAVMDVYST |
| 49176308 | 459 | MYHAAKALDDTRLVHYEEDRD..........AEVVDIIST |

| | | |
|---|---|---|
| 29377189 | 484 | MYTWLEHPTRELLMNTIIENSKKPHILCEYCHAMGNGPGN |
| 116493950 | 476 | MYTWLEHDT.KMTMADVLQKTQKPHILCEYAHSMGNGPGN |
| 40745013 | 491 | MYS.....SPDTMLEHMANHTDKPLILCEFAHAMGNGPGG |
| RAAC02616 | 504 | MYT.....SVDELSRLGELELPKPHILCEFAHAMGNGPGG |
| 49176308 | 489 | MYT.....RVPLMNEFGEYPHKPRIICEYAHAMGNGPGG |

| | | |
|---|---|---|
| 29377189 | 524 | LKEYQELFYAHDKLQGGFIWEWFDHGIESVTDNGEVYYRY |
| 116493950 | 515 | LKEYQDLFYGHQQLQGGFIWEWFDQGVAAQQGD.QTYYRY |
| 40745013 | 526 | LKEYIELFRSHPLSQGGLVWEFNNHGLLKKEGD.LEYYAY |
| RAAC02616 | 539 | LKEYVELFYQQRRLQGGFVWEWIDHGILAYTSDGRPYFAY |
| 49176308 | 524 | LTEYQNVFYKHDCIQGHYVWEWCDHGIQAQDDHGNVWYKF |

| | | |
|---|---|---|
| 29377189 | 564 | GGDFGDDPSNKDFCIDGMLPDRTPSPSLYEYKKVIEPIT |
| 116493950 | 554 | GGDFGDQPNNSNFCIDGLIRPDGQPSTALTEVKKTFEPFQ |
| 40745013 | 565 | GGDFGDEPNDADFVMDGLTLSDHTPMPSLLEYAKIIQPVS |
| RAAC02616 | 579 | GGDFGDVPNDLNFVIDGLLFPDRTPSPGLFEYKKAIEPVR |
| 49176308 | 564 | GGDYGDYPNNYNFCLDGLIYSDQTPGPGLKEYKQVIAPVK |

FIG 20C

```
29377189    604  TSAIDVLSGEFSLLSRFDFENLAIFKLVYTITEDQTVIQS
116493950   594  MTVRDLPTQTITVTNRLDFLSSDQFNFGYELEADGKLMAT
40745013    605  VNLTDDSS.SMVITNHYAFVDLSGLDVSWHIVQDGETTEA
RAAC02616   619  VLEFDRSSGIIKVQNRYDFLCLDCLVAEWSLQDEQSVLAG
49176308    604  IHARDLTRGELKVENKLWFTTLDDYTLHAEVRAEGETLAT 29377189    644  GTVAVPAIAARAEGRLHLPYHLDFPKKAGAAYYLTLSYQL
116493950   634  GKIDLPTIMAGTTKTIKLDIELP.KLDPEVIYNLHVLTEL
40745013    644  QELDLPPVP...AGESRTVDLPLDPSSLSKETWLTIEFKL
RAAC02616   659  GILELEPVPPRSIGQIRVPCAEILNRHRDRCLTLTVRFLL
49176308    644  QQIKLRDVAP....NSEAPLQITLPQLDAREAFLNITVTK 29377189    684  KETTAYASAGHELATAQFELPIA.........TPGIEITP
116493950   673  KNQTSWADAGTVLSQTVVNLQRP.........QHHMTHQQ
40745013    681  KEDKAWAVRGHVVAWDQLYFPGSSASTSSSKRSTPISRQT
RAAC02616   699  RHPTDYAPAFHEVASFCEYVERSCQNAS.....IDIYRPV
49176308    680  DSRTRYSEAGHPIATYQFPLKENTAQP......VPFAPNN 29377189    715  VGSLMAKEIGPHLYIEGPNFSINFDKVKGALTNVTRDGKK
116493950   704  TTALQASENATTIMVTGGQNEYRFDKIKGTFS.LTHDGHK
40745013    721  SGGLEVKQNQTSLRIITGTSIFGFNLIQGNVTWEAN.GAS
RAAC02616   734  TR.FEIVEKGSSLCIYDDSFSVEFDLLRGRISGVGYRGSQ
49176308    714  ARPLTLEDDRLSCTVRGYNFAITFSKMSGKPTSWQVNGES 29377189    755  LLHKGPKFTFWRAPISND......MEIIDEMKKKYFLHLE
116493950   743  LIADGIKMNFWRAPIDND......MYLLDDYYNKYFLNLW
40745013    760  LFQRGPELSFIRAMTQNDEGQS....GNEAEWDDAWVGTM
RAAC02616   773  IIMSPLSMSFWRAPTDNDDPPNREMFSVAKVWRDYGVDRL
49176308    754  LLTREPKINFFKPMIDNH......KQEYEGLWQPNHLQIM 29377189    789  HEIVRSFEWKKVD..DFIQVIVKTINGTTNSAWHYQCTYQ
116493950   777  HESTREVQLHPQTNGDYVVNLTKQVG.TTNSGWYYLIQQQ
40745013    796  HTQVRDVTWRSSD..TEAIVHFKVRVAPQVLEWGVEADLI
RAAC02616   813  SESVSNIEIKKHD..NVVRALVESRVAPAGLSWGMALQYE
49176308    788  QEHLRDFAVEQSD..GEVLIISRTVIAPPVFDFGMRCTYI 29377189    827  YLIAPNG...EIFFDLKGSPAGKIENAPDMLPRLGVTLHL
116493950   816  YTMHQDG...SFDLDVIGKASGKRDMAPEMLPRIGVKMTL
40745013    834  YTISTEDSVPTLHIHATGEFVG..TNTPSVVPRIGLQTIL
RAAC02616   851  YIFLRGG...LVMVRICKPEG..AYPP.TLPRIGLLTTI
49176308    826  WRIAADG...QVNVALSGERYG...DYPHIIPCIGFTMGI 29377189    864  DKSLSEVKYFGKGPRENYVDSQEAGLLGVYDATVAEMFTN
116493950   853  PKAYQQVSYDGLGPTENYSDSHQAAYYSHFTSSVDDLFVN
40745013    872  PSSFNFVRWLGRGPGENYKDSKQACRIGEYSATVEELFTH
RAAC02616   885  HLDFEYVSWFGRGPGESYRDSKESQLIGRYRRLADELYTP
49176308    860  NGEYDQVAYYGRGPGENYADSQQANIIDIWRSTVDAMFEN
```

FIG 20D

```
29377189    904  YVVPQANGNHMATKWSAFTD..........DRGQGVVATA
116493950   893  YVKPQENGNHMDTDQIALTD..........GQDQ.LTVTM
40745013    912  YDYPQENGNREDLRWLQISDPGTGVTLDARRADASTNQTA
RAAC02616   925  YVYPQENGNRTDVYWISITN..........KYMEGLFITG
49176308    900  YPFPQNNGNRQHVRWTALTN..........RHGNGLLVVP 29377189    934  ADSYNFSVSYFEEQALDVAKHTNELQESEYVVLNIDYKQN
116493950   922  AKPLNFSVSNYADETLEAAKHTIDLKKSDALNLYLDFRQN
40745013    952  VEVFSFTASQYMPIDLNNAKHPFDLKPLDMTILWLDYDNH
RAAC02616   955  PQPLNFQVSRFSVEDLERARHPYELEESPWRYLRIDFSHH
49176308    930  QRPINFSAWHYTQENIHAAQHCNELQRSDDITLNLDHQLL 29377189    974  ALGSYSCGQWQLEKYRTTFEEFQLAFRLTPFNNKEIQAAD
116493950   962  GLGTNSCGQNQLKRHRCKFDDFELGFNFKVN
40745013    992  GLGSASVGPQPFEQYRCKTEPFDFAFELSLLS
RAAC02616   995  GLGSASCGPGPLPEHQLRTEPFEWTLCFAPLARHEIDESI
49176308    970  GLGSNSWGSEVLDSWRVWFRDFSYGFTLLPVSGGEATAQS 29377189   1014  VAHERVKRPTIS
116493950
40745013
RAAC02616  1035  LHQVVTERLKFI
49176308   1010  LASYEFGAGFFSTNLHSENKQ
```

FIG 21A

```
15642830    1                          MDYRMCWLEYRGLP.ADVAGKLK
148270004   1                          MDYRMCWLEYRGLP.ADVAKKLK
15613624    1          MNR........GETGYETWLRYEEITDSALHTQYR
118725970   1          MYKSNVNDELYGANGYNCWLGYHLLENGELRENYS
RAAC02661   1               MTNIPEGDLDYRAWLQESPLPRAVPEAARR
116621784   1 MSFKFLALLLTIPAVHAETGYDAWLRYAPLSDAAARPYLT
```

```
15642830    23 DWFSSVSILEPGS..SVLKDEIRRFSERSIGITPRFYSRP
148270004   23 DWFSSVSILEPGS..SVLKDEIRRFSERSIGITPGFYSRP
15613624    28 AYFQTIEIKGNSPIIESAKEELMQGLRSLLGVTPKCLSAT
118725970   36 QWASNIVISKEPDEIKIALSELKSGINGILGVDAVVVTRE
RAAC02661   31 ...MAVYGPADDPLLCTAAAEWGRAVRAACGESPARLARD
116621784   41 ALPAAVTVYGASPVVQSAQRELLRGVRGMLGRTLRMESKL
```

```
15642830    61 LKKE...KYIMVGRLESLP......IKLD..VNLGEEGFM
148270004   61 LKKE...KYIMVGRLESLP......IKFD..ENLGEEGFM
15613624    68 GEQA...SCL.IGTIADVAE.VSQAIK....ERLREEGYA
118725970   76 PEQS...SCIALGVLGRGQN.IDSYVKYDEVVQIGNEGFI
RAAC02661   68 PGGAPSVPCVAMGLLSAMPRGLREAAQAALAGAPSDEAYA
116621784   81 PAER....AILLGTAGDLQA...AIPQLHLPPDLPADSYL
```

```
15642830     90 LRTIEWNGSKILLVTGETKKALVYGIFDLMKRIRLGEDIE
148270004    90 LRTLEWNGSKILLVTGETKKALVYGIFDLMKIIRLGEDIE
15613624     99 IYSEKGR....LVLVGKTETGVLYGTFHLLRLLQMRDHLH
118725970   112 IKAFKTGNSEIVVVAGTTTKGLLYGVFSLLRLLQTEATIS
RAAC02661   108 ILPVDGQG...VAVVSRTPAGVLYGVFHLIRRLRLGEPLH
116621784   114 VTTVTANGAPHLVIAGANDRAVLYGVFALLRKIGTGQTLN
```

```
15642830    130 KMNVLAKPKAKFRMLNHWDNLDGTIERGYAGNSIFFKDNR
148270004   130 KMNVLEKPKAKFRMLNHCDNLDGTIERGYAGNSIFFKDNR
15613624    135 DLRIVENPRNQLRMINEWDNMDGSIERGYAGGSIFFEHNK
118725970   152 GILKIENPANQLRIINHWDNIDGSIERGYAGKSIFFTDNK
RAAC02661   145 EP.CVSSPKNAWRMLDHWDNADGTIERGYAGKSLFYRGGQ
116621784   154 DDDPVQTPYAPVRWVNEWNNLDGTIERGYGGRSIFWDNNR
```

```
15642830    170 IIIN.QRTKDYARLLASIGINGVVINNVNVKKREVYLIDS
148270004   170 IIIN.QRTKDYARLLASIGINGVVINNVNVKKREVYLIDS
15613624    175 VTNNLQRIKDYARILSSIGINAIAFNNVNVHEEETKLITR
118725970   192 VTEDLGRIKDYARLLCSVGINSIVINNVNVHKYESMLITD
RAAC02661   184 IDFDEGRVRDYARLLASVGVNAIAINNVNVHETETRFLTE
116621784   194 ARADLTRVADYGRMLASLGIQACSINNVNAN...PRVLAS
```

```
15642830    209 IYLKKLKKLADIFREYGIKIYLSINFASPVYLGGLDTADP
148270004   209 IYLKRLKKLADIFREYGIKIYLSINFASPVYLRGLDTADP
15613624    215 KFLPDVAKVANIFRQYGIKTFLSINYASPIQLGKLETADP
118725970   232 KYLNDVASLAQIFRDYGIKLYLSANFASTIEIGGLATADP
RAAC02661   224 AHLPGVARLADVFRPYGIRVFLSINFASPVDLGDLPTADP
116621784   231 DFLPEIVRIAEAFRPWGIRVALAVDFGSPKTIGGLDTFDP
```

FIG 21B

```
15642830    249  LDERVARWWREKARGIYDYIPDFGGFLVKADSEFNPGPHM
148270004   249  LDERVAHWWREKAREIYDHIPDFGGFLVKADSEFNPGPHM
15613624    255  LDEKVRAWWKETVADIYRYIPDFGGFLVKADSEHRPGPFT
118725970   272  LDPQVRKWWKEKADEIYSLIPDFGGFLIKADSEFRPGPFT
RAAC02661   264  LDPRVEDWWRATADRIYRHIPDFGGFLVKADSEFRPGPFT
116621784   271  VDPKVAAWWKSKIDELYRAVPDLAGIVLKADSEGRVGPST
```

```
15642830    289  FGRTHAEGANMLARALAPFGGVVIWRAFVYNCLQDWRDYK
148270004   289  FGRTHAEGANMLARALAPFGGVVIWRAFVYNCLQDWRDYK
15613624    295  YGRNHAEGANMLAEALAPFGGIVLWRCFVYNCLQDWRDRK
118725970   312  YGRTHADGANMLAEALEPYGGLVIWRCFVYNCMQDWRDRI
RAAC02661   304  YGRDHADGANMLARALAPHGGVVIWRAFVYNCLMDWRDRR
116621784   311  YGRTHADAANVVARGLQPHGGLLFYRGFVYDHHMDWKNPK
```

```
15642830    329  TDRAKAAYDNFKPLDGQFDDNVIIQIKYGPMDFQVREPVN
148270004   329  TDRAKAAYDNFKPLDGQFDDNVIIQIKYGPMDFQVREPVN
15613624    335  TDRARAAYDHFKPLDGLFHDNVVLQIKNGPMDFQVREPVS
118725970   352  TDRARAAYDNFMPLDGLFRENVLLQIKNGPMDFQVREPVS
RAAC02661   344  ADRARAAYDHFVPLDGRFLDNVLIQIKNGPMDFQVREPVS
116621784   351  NDRGRAAYDNFQPLDGKFDANVIVQIKHGPIDFQVREPAS
```

```
15642830    369  PLFGGMEKTNQILELQITQEYTGQQIHLCFLGTLWKEILE
148270004   369  PLFGGMERTNQILELQITQEYTGQQIHLCFLGNLWKEILE
15613624    375  PLFGAMPKTNQMLEFQITQEYTGQQKHLCYLVPQWKEILD
118725970   392  PLFGGLQKTNQLLELQITQEYTGQQKHLCYLVPMWKEILD
RAAC02661   384  PLFGGLSATNVMLEFQITQEYTGQQRHVCYLAPMWKEVLD
116621784   391  PLFAALEKTNQAIELQITQEYFGQSRHNVFLVPMWKTALD
```

```
15642830    409  FDTFAKGEGSYVKRIVDGTLFDRENNGFAGVSNVGDSVNW
148270004   409  FDTFAKGEGSYVKRIVDGTLFDRKNNGFAGVSNVGDSVNW
15613624    415  FDTFANGKESPVKSIVDGSQYDYKVSGITAVSNVGNDENW
118725970   432  FDTMAKGRNTSVKKIITGSVFNNKLGGMAAVTNIGNDLNW
RAAC02661   424  FDTHARGPGSTVAEIASGRLFGRPHGGVAGVANVGDDVNW
116621784   431  FDMQAGG.TTPVKALAAGKVFHRPIGGFVGVSNIGLDDNW
```

```
15642830    449  TGHDLAQANLYAFGRLAWNPDEEIERIVEEWIKLTFGDDE
148270004   449  TGHDLAQANLYAFGRLAWNPDEEIERIVEEWIKLTFGDDE
15613624    455  TGHLLAQANLYGYGRLTWNPNLSTEEVTTEWTRATFGDNE
118725970   472  TGHQMAQSNTYGYARLCWNPDLSAEKITDEWVRMTYSNYE
RAAC02661   464  TGHSLAQANLYAFGRLAWDPSLDPAGIAREWARLTYGDDP
116621784   470  SGNQLSQANLYGFGRLAWNPDLTSQQIIDEWTRLTFGNEP
```

```
15642830    489  KVLENVSYMLMKSHRTYEKYTTPFGLGWMVN.PGHHYGPN
148270004   489  KVLENVSYMLMKSHRTYEKYTTPFGLGWMVN.PGHHYGPN
15613624    495  EVIQTIHEMLLQSWLIYESYTAPLGVGWMVE.PGHHYGPN
118725970   512  KVVNTVKEMLLGSWRTYENYTSPLGIGWMVN.PNHHYGPN
RAAC02661   504  DVVRTVVGILMASWPAYEAYTAPLGVGWMVN.PGHHDGPN
116621784   510  KTVETITAMQLASWPVFEKYTGPLGLQTLTDIVGDHYGVA
```

FIG 21C

```
15642830    528  PEGYEYSKWGTYHRANWEAIGVDRTSR.GTGYTLQYHSPW
148270004   528  PEGYEYSKWGTYHRANWEAIGVDRTSR.GTGYTLQYHSPW
15613624    534  VDGYEYSVWGTYHYADCHGIGVDRTVATGTGYTAQYFAEN
118725970   551  VDGYEYDKWGTYHRADHKGIGVDRTVKSGTGYAGQYHKDV
RAAC02661   543  PEGYEYSKWGTYHYADWRGVGVDRTMATGTGYTGQYHEPM
116621784   550  VEASEHNGWGQWHNADEKGVGMDRTVATGTGYIGQYRPPV 15642830    567  KEIYDDINTCPEDLLLFFHRVRYDHRLKSGKTLLQTMYDL
148270004   567  KEIYDDINTCPEDLLLFFHRVRYDHRLKSGKTLLQTIYDL
15613624    574  YELYEHLETCPDSLLLFFHHVPYTHKLKSGVTVIQHIYDT
118725970   591  AGIYEDMDKCPEELLLFFHHMPYDYILKSGETLIQYIYNT
RAAC02661   583  RSLYEHLETCPDELLLFFHHVPYTHVLHSGKTVIQHIYDA
116621784   590  AKMYESLETCPDDLLLFLHHVPYTYKLHSGKTVIQYLYDS 15642830    607  HFEGVEEVEEFIKKWEELKDRVSPDIFERVKERLHMQLEH
148270004   607  HFEGVEEVEEFIKKWEELKDRVPPDIFERVKERLHMQLEH
15613624    614  HFSGAEQAEQLLESWRSLEGKVDSERFQQVLERLEHQAEH
118725970   631  HFKGVEEVEELRNKWFSLKGWISEEIFLHVLERLDGQLEH
RAAC02661   623  HFDGVEAVAWMIEAWRRLQGRIDPVRFERVLARLEDQMQR
116621784   630  HYEGADAVAAWVRDFQSLRGHIDDQRYNEVLAQLRYQAAH 15642830    647  AKEWRDVINTYFYRRTGIPDEKGRK...............
148270004   647  AKEWRDVINTYFYRRTGIPDEKGRK...............
15613624    654  AKEWRDVINTYFYRKSGIPDEKKRT...............
118725970   671  SKEWRDVINTYFYRKTGISDELGRK...............
RAAC02661   663  AVEWRDVINTYFYRKCGIPDARGLH...............
116621784   670  VEVWRDAVNNWFHRESGIADAKGRVGNHPGRSEAEAMKLE 15642830    672  ......IYP
148270004   672  ......IYP
15613624    679  ......IYPI
118725970   696  ......IY
RAAC02661   688  ......IYP
116621784   710  GYTVAEITPWESASGGKAVTCPASKCTASMQFSGAPGWYT 15642830
148270004
15613624
118725970
RAAC02661
116621784   750  LRVQYFDLNGPVSSFKLWVGNQLVDEWSATDHLPARKLDA 15642830
148270004
15613624
118725970
RAAC02661
116621784   790  SSSTRREVSGIALRPGDQVRIEAIPEGRELAALDYLEILP
```

FIG 21D

```
15642830
148270004
15613624
118725970
RAAC02661
116621784    830 NEPRQ
```

FIG 22A

```
RAAC02925
52080473
17552962
15292329
66851010      1  MFKPPLCSEFRCRTARNRGIGDVLGSKTVHLVQLPAEENQ
40739053

RAAC02925
52080473
17552962
15292329
66851010     41  TARKTPRSSVHPKRRNDFLSRVISTNFLHFHSLSLSPQRR
40739053

RAAC02925
52080473
17552962      1                   MAATVRNLPALFR.........
15292329      1              MGPIQRLVYTFGHRTCSQLPMIGG.........
66851010     81  TVVCLDVTSTQFLPLTNAGELDLAGFITNASPRQSDESSF
40739053      1              MPLR..AKVTNPGFAATSN.........

RAAC02925     1                            MDSVLFRQTG
52080473      1                            MSDDVLFSVNQ
17552962     14  ...........GLHSKEVCQKMSFSVSAAAKSEILVDTHG
15292329     25  ...........ATISQTKPTTMALSVRQSS.SSVLATESS
66851010    121  RGCCEGMLYSLSLFAMSTAPELPKELPGDEPDDVLFSSLY
40739053     18  ..............MSTASNPDIPKAQHGDEPDDVLFNSLF

RAAC02925    11  .TVAWLGLNRPKQLNALSLEMIRLLRRHLDEMAQDPSVEL
52080473     12  NGAAAIVLNRPKALNSLTYDMVRLIGEKLNEWETDQNVSI
17552962     43  .SKKVVTLNRPKALNALNLEMVREFYPKLQAWNSSSDVDL
15292329     53  .NKGMIILNRPKALNAINLEMVRKIYKHLKKCEKSK..SL
66851010    161  .GVRLIELNRPKKLNSLNGSMARKILPRLKEWEKSQLANI
40739053     45  .GVRLVELNRPKKLNSLNGSMVRKILPRLKEWEKSQLANI

RAAC02925    50  VVLYGEGDRAFCAGGDIRALYDAKD.EPNLETAA...AFF
52080473     52  VVIKGAGPKGLCAGGDIKALYEARSSKQALQDAE...RFF
17552962     82  VILKGSGDKAFCAGGDVLAVVRSFKDSESGKECTMHKDFF
15292329     90  VIIKGTGDKAFCAGGDVRALVEAGPTDES.......KSFF
66851010    200  VMLSGAGTKALCAGGDVASLALQNEQGPEGQQKS..TDFF
40739053     84  IMVAGAGTKALCAGGDVAALALQNEKGPEGQQAS..TDFF

RAAC02925    86  SEEYALDDRVARFPKPVVALWDGIVMGGGVGLTYGATWKV
52080473     89  ETEYEVDMAVHRFSKPIIACLDGIVMGGGVGLTYGASHRI
17552962    122  REEYILNHLIGTLNKQYVCLIDGIVMGGGCGLSVNGRFRV
15292329    123  REEYSTNALIGNYKIPYIAIIDGITMGGGVGLSVHGKYRV
66851010    238  GLEYRLDHIIATYTKPFISVMDGITMGGGVGLSVHAPFRI
40739053    122  GLEYKLDHVIATYSKPFISVMDGITMGGGVGLSVHAPFRI
```

FIG 22B

```
RAAC02925   126  ATDRTRFAMPETGIGFFPDVGMCHALSRMQGGLGHYLALT
52080473    129  VTERTKWAMPEMNIGFFPDVGAAYFLNKAPGRLGRYLGLT
17552962    162  ATEKTMLAMPETALGLFPDVGGSYFLSRLKGNLGMYLALT
15292329    163  ASDRTLFAMPETAIGLFPDVGGSYFLPRLQGKLGLYLGLT
66851010    278  ATERTVFAMPETTIGFFPDVGGSFFLPRLDGEIGTYLALT
40739053    162  ATERTVFAMPETTIGFFPDVGGSFFLPRLDGEIGTYLALT
```

```
RAAC02925   166  GESVGADVLLAAGLANGWLPSGERPSFEAELVKRGEQGE.
52080473    169  ASVIHAADVLYINGADAYMESGALERLLQAVEQTDWRLA.
17552962    202  GYRLLGADAFHAGLATHFVESSELAKLEKELVNIKDVTEN
15292329    203  GYRLRGADVYYSGIATHYCESSKIPDLETALLNCPDADD.
66851010    318  SERLNGVQALYAGIATHYFHSSVLSNLTARLAELVFRDHA
40739053    202  SARLTGVQALYAGIATHYFDSSVLGNLTQRLSELVFRDSA
```

```
RAAC02925   205  TAEQLQRWLAARLAVEHR.........PSEAVADFLRRVQ
52080473    208  SVEEKLDQLIRESKTEPS.........QESTLARDQQAID
17552962    242  SVDEVIRSFEPKKIPEFS............LSKNLAQIR
15292329    242  .VPELLQKYHSPPEKPFS.............LQPVLEQIN
66851010    358  SLAERLDLVN.KTMAEFSVGLPPVEQEPIQLAGSLRSAID
40739053    242  TLQERLDLIN.RTMAEFATGLP....EEPQLAGQLRSAID
```

```
RAAC02925   236  AYFDSPSLSDILARLREGSSRDPFAAQALEILRQRSPLSL
52080473    239  RHFKYDKLEEILQSLE..SEGSTFSSNVKKTMLSKSPFSL
17552962    269  DSFKAKSVEEILASLEKDG..SDWAKKQAATLGKMSPTSL
15292329    268  KNFSADSVEGILENLQNDG..SEWAKKTLETLSKMSPTSM
66851010    397  RCFKHNTVEEIFRALEQETVHKEWAQKTLETLSSRSPTSL
40739053    277  RCFRHDTVEQIMKALEREKKCKKWAQETLETMSQRSPTSL
```

```
RAAC02925   276  AVTFEALRRAGNATYREVLETDLTLALQFIRRGDFVEGVR
52080473    277  KITLKQLADGRQKTLEECFATDLVLAKNFLKHNDFFEGVR
17552962    307  KVTHRQITEGSKMSYAKIFTMEYRLTQRFLADKDFHEGCR
15292329    306  KVTFRQLELGSQLSLAQCLIMEYRLAVRHLERSDFKEGVR
66851010    437  KVTLRQMRVGKKWSISETFQREYQIAAQFMKHPDFVEGVK
40739053    317  KVALRQMRVGQAWGIRETFQREYEIAARFMQHPDFVEGVK
```

```
RAAC02925   316  AQLVDKD.RRPRWRHADLASVTAEEVEAFFEPIAHLSIPF
52080473    317  SVLIDRD.QSPNYKYRNVSDVTDEAVDRFFQPSE...SVRF
17552962    347  AILVDKD.RKPKWNPATLADVKDSVVDNYFSPLPNNSDLK
15292329    346  ALLIDKD.QKPQWQPTKLADVTEEHVQWFFRKLPDTEELK
66851010    477  ARLMSKPPRQATWQPATLEEVTNDAVDAFFKLPADKSRLT
40739053    357  ARLMSKPPRQASWQPATLAEVSEKDVDEFFKIPQGKERIQ
```

```
RAAC02925   355  AD
52080473
17552962    386  L
15292329    385  L
66851010    517  LFNKTDYKQYPHAYGLPSEAEIEKFVRDSS....ESASKT
40739053    397  LLSQENWRSYPHSYGLPSEKAIEKFIREADPKSRASKGEV
```

FIG 22C

```
RAAC02925
52080473
17552962
15292329
66851010    553  VADFVEKWGHKEGVREKVAEVLARRTVQTPEGLRWE
40739053    437  IEHFVKEFEHKEGVKEKVAEVLARKTTKSAEGLIWQGEGA

RAAC02925
52080473
17552962
15292329
66851010
40739053    477  ETDGQ
```

FIG 23A

```
125973771    1  MAVDIKKIIKQMTLEEKAGLCSGLDFWHTKPVERLGIPS
RAAC03001    1   MSYRDLVSRLTLEEKASLCSGLNFWQTKPIERLGIPS
116334524    1  MDIERTL...AELTLPEKAALVSGKNNWYTAAVDRLDLPA
116617985    1  MSTEFNLSFVQGLTVREKAELVTGKDFWFTAENIENDIPK
116494248    1  MGVVVSNFHLAKITAEEKVKLTSGKDFWTSEHLADKGIPS
66851551     1  MVQLDVEKTIEELTLGEKVALTAGIDFWHTAAVPRLNIPS 125973771   40  IMMTDGPHGLRKQREDAEIADINNSVPATCFPSAAGLACS
RAAC03001   38  LCMTDGPHGVRLQRQGGSFTDSE...PATCFPTAAALASS
116334524   38  LMMTDGPSGLRKQINSGTTN.INDAIQAITYPAAALSAST
116617985   41  IMVTDGPSGLRKQASSADALGLNQSVEAIAFPSSALMASS
116494248   41  FRMSDGPHGLRYQALAADHLGINDSVPSTSFPTASASAAA
66851551    41  LRMSDGPNGVRGTR.......FFNGVPAACFPCATALGAT 125973771   80  WDRELVERVGAALGEECQAENVSILLGPGANIKRSPLCGR
RAAC03001   75  WDPALVERIGQALGDECRALGHVLLGPGANIKRSPLCGR
116334524   77  WNESLMHQLGEHLGIEARAEQVSLLLGPGVNMKRSPLGGR
116617985   81  FNVDMLYQLGQNLGTASRAENVSVLLGPGINIKRSPLAGR
116494248   81  WDPDLIQAMGKAIGLEAQSLGVDMVLGPGVNMKRNPLCGR
66851551    74  WDTKLLYEVGRLMGEESIAKGAHVVLGPTINTQRSPLGGR 125973771  120  NFEYFSEDPYLSSELAASHIKGVQSQGVGACLKHFAANNQ
RAAC03001  115  NFEYFSEDPLLSSEMAAAHIRGVQSRGVGSSLKHFAANNQ
116334524  117  NFEYLAEDPLVAGKLGSAYVQGVQSQHVGVAVKHFAANNR
116617985  121  NFEYFSEDPYLTGELGSAYVKGVQSQGVGVSVKHFAANNR
116494248  121  NFEYFSEDPFLAGKLGAAWINGIQSQGIAACLKHFAANNQ
66851551   114  GFESFAEDGVLSGILAGHYCKGLQETGVAATLKHFVCNDQ 125973771  160  EHRRMTVDTIVDERTLREIYFASFENAVKKARPWVVMCAY
RAAC03001  155  EYRRMTTSAEVDERTLREIYLASFEGAVKGGRPWTVMCAY
116334524  157  ENQRFTASSDMSERTLRELYLRTFEIIVKSAYPATIMTSY
116617985  161  EDQRFTSSSNVDERALREIYLLAFEKIVKEAHPATLMCSY
116494248  161  ENDRLSSDSLVDPTALHEIYLEAFRIAVTESHPEAVMCSY
66851551   154  EHERLAVDSIVTMRAMREIYLLPFQLAMRICKTACVMTAY 125973771  200  NKLNGEYCSENRYLLTEVLKNEWMHDGFVVSDWGAVNDRV
RAAC03001  195  NRLNGTYCSEHPWLLTQVLRREWGFDGVVVSDWGAVNDRV
116334524  197  NKINGVLNSQNERLLRRILRDEWGFHGAVMSDWGAVANTV
116617985  201  NAINGVLNSQNYRLLTEILRNEWGYTGVVMSDWGAVADNI
116494248  201  NKINGTYASDNLYLMTQVLRQQFGFGGAVITDWGALNDKV
66851551   194  NKVNGTHVSENKQIITDILRKEWGWDGLVMSDWFGTYSTC 125973771  240  SGLDAGLDLEMPTSHGITDKKIVEAVKSGKLSENILNRAV
RAAC03001  235  QGLAAGLDLEMPGGPYAQDAEIVQAVRDGRLDEAVLDAAV
116334524  237  QALKAGLDLEMPGKGQASINDIIRAVHTGELDEGTLNKAV
116617985  241  ASLKAGLDLEMPGNGAYSIDRIVSAVQNGQLEESKLDISV
116494248  241  AALNAGTDLEMPGDDHLFDGEALQAYQQGTLKLASLDRAV
66851551   234  DAINAGLDLEMPGPTRWRGTALAHAVSSNKAFEFVMDERV
```

FIG 23B

```
125973771  280  ERILKVIFMAL....ENKKENAQYDKDAHHRLARQAAAES
RAAC03001  275  ERLLALIDRAY....RPQGDSA..DLDAHHRLARQAAAES
116334524  277  RHLLHVVDDW.....LPADHAQPYDHAAHHQFARKLADDG
116617985  281  LRVLALVEKFR....VSEDDSTDYDKNNQHEFARKAAEDS
116494248  281  TKIAEIARKQR....PKFQGSREQLLQANGQLAQKIAESA
66851551   274  RNILNLHNFVEPLGIPENAPEKALNRPEDQALLRRAAAES 125973771  316  MVLLKNEDDVLPLK..KSGTIALIGAFVKKPRYQGSGSSH
RAAC03001  309  MVLLKNDGAVLPIA..PGRRVAVIGAFAVSPRYQGGGSSH
116334524  312  IILLKNHEDELPLDPQTTGKVVVIGELAENPRFQGSGSSH
116617985  317  IALLKNDDDVLPIK..QTEKIALIGELAQNPRYQGGGSSH
116494248  317  IVLLKNEAALLPLQ..ATDTVAVIGELAKATRFQGAGSSH
66851551   314  VVLIKNQDNILPLK..KEKPILVIGPNAKTAAYCGGGSAS 125973771  354  ITPTRLDDIYEEIKKAGG......................
RAAC03001  347  VNPARLDEPLAEMRRAFG......................
116334524  352  VNPTKLVSPLDELAGS........................
116617985  355  VNAYKVVTPHEVASNS........................
116494248  355  INASEIVSVLDGLKQK........................
66851551   352  LDAYYTVTPFEGVAAQSQGEVTFSQGVYSYKELPLLGPLL 125973771  372  ........................DKVNLVYSEGYRLE
RAAC03001  365  ........................DQL.VLYAPGYALD
116334524  368  ........................GLKADYYPGYRLD
116617985  371  ........................DYNVTYTAGYSLS
116494248  371  ........................KVSFDYAAGYRLD
66851551   392  KTDDGKKGFKFRVYNEPPSEPNRQLIDELHLESSSGFLMD 125973771  386  ........................................
RAAC03001  378  ........................................
116334524  381  ........................................
116617985  384  ........................................
116494248  384  ........................................
66851551   432  YKHPKIKTFTFYVDMEGYFTPEEDGIYDFGVTVVGTGKLF 125973771  386  ........................................
RAAC03001  378  ........................................
116334524  381  ........................................
116617985  384  ........................................
116494248  384  ........................................
66851551   472  VDDELVVDNSKNQRQGTAMFGNATVEEKGSKELKAGQTYK 125973771  386  ..............................NDGIDEELI
RAAC03001  378  ..............................DDAPRLELI
116334524  381  ..............................QSETNGDLA
116617985  384  ..............................EEKGNLDLE
116494248  384  ..............................DQD.DSQAT
66851551   512  VVLQFGTAPTSDLDMRGVVIFGPGGFRFGAARRVSQEELI
```

FIG 23C

```
125973771   395  NEAKKAASSSSDVAVVFAGLPDEYESEGFDRTHMSIPENQN
RAAC03001   387  EEAVRAAAQADVAAIFAGLPESWESEGYDRPHMRMPDAHV
116334524   390  EAALTAAKTADHVIIFAGYPEAAESEGFDKASLMLPENQS
116617985   393  QQAESIAELSDKIIFFAGVPEQDESEGFDKKTIDLPENQV
116494248   392  AEALALARNHDKVVFVAGLPDNYESEGFDRQNMALPKVQN
66851551    552  SKAAELASQTSQVVIFAGLTSEWETEGYDRDHMDLPPGSD 125973771   435  RLIEAVAEVQSNIVVVLLNGSPVEMPWIDKVKSVLEAYLG
RAAC03001   427  ALIEAVTSAQPRTVVVLSNGAPVEMPWIHRVPAVIEAYLA
116334524   430  DLIGSLAKANVHTTVVLQNGSAVEMPWIHSVAAVVETYLA
116617985   433  NLIQKLSAINPNIIVVLQNGSAVATPWRNKVKAIVETYLA
116494248   432  DLLQAVTAVNPNVIVLLVAGAPVELPWVDQVKAVVNLSLG
66851551    592  EMISRVLDANPDTVVVIQSGTPVTMPWAHKAKALLQAWFG 125973771   475  GQALGGALADVLFGEVNPSGKLAETFPVKLSHNPSYLNFP
RAAC03001   467  GQAFGGAIADVLSGAVNPSGKLAETFPLRLEHNPSHPYFP
116334524   470  GEAVGEATWDIITGAVNPSGHLTETFPRRLTDTPMAPTFG
116617985   473  GEAVGEATWNILTGQTNPSGKLAETFPEKIEDTPAYGTFN
116494248   472  GERIGAAAANVLTGAVNPSGKLAESYPLKYQDVPSADVYD
66851551    632  GNECGNGIADVLYGNVNPAAKLPLSFPVRLQDNPSYLNFR 125973771   515  GEDDRVEYKEGLFVGYRYYDTKGIEPLFPFGHGLSYTKFE
RAAC03001   507  GEGDRSEYREGVFVGYRYYDTKEMDVLFPFGHGLSYTTFE
116334524   510  QDPHHEYYTEGIFMGYRYYDTHEMHVLFPFGHGLSYTTFE
116617985   513  ASVDEENYHEGIFVGYRHYDLKRKEVAFPFGHGLSYTDFK
116494248   512  KKPRSVPYVESTYIGYRYYDKAKVPVAFPFGFGLSYTSFA
66851551    672  SERGRVLYGEDIYVGYRYYEKVDLAPLFPFGHGLSYTTFS 125973771   555  YSDISVDKKDVS....DNSIINVSVKVKNVGKMAGKEIVQ
RAAC03001   547  YEAIRMSREQVR....DDDVLTVQVDVRNTGQRAGKEVVQ
116334524   550  YTNLKLTQN........ERGATVTFDVTNTGARSGQAVPQ
116617985   553  YDDLEIVANT.......KKHVTGKIKITNVGSIYGKETAQ
116494248   552  LKNIQLSSDHVT....DDQPLTISLQVTNTGQVDGAEVVQ
66851551    712  RSDLSLATTPEKPQLEDGEPITVTVSVTNTGSVAGAEIVQ 125973771   591  LYVKDVKSSVRRPEKELKGFEKVFLNPGEEKTVTFTLDKR
RAAC03001   583  VYVEPRSSRVVRPRRELRAFAKVALAPGETRTVEFQLGKR
116334524   582  LYIANHASHVPMPTKELRAFTKVAIAPGETETVTLALDRR
116617985   586  IYIQNLESRVEKPRQELKAFVKVGLNPGESKTVEFFLDRR
116494248   588  VYVQEQQPRPLRPEKSLKAFKKVFVKAGQTVNVALELKAQ
66851551    752  LWVAPPPTGVNRPVRELKGFTKVFLQPGETKKVEIVVEKK 125973771   631  .AFAYYNTQIKDWHVESGEFLILIGRSSR..DIVLKESVR
RAAC03001   623  .AFAYYDVDAGDFAVESGWYEIRVGSSSR..DLRLTASVE
116334524   622  .DFSWWCEPKARWQADSGDYEVMIGESSR..DIRLQVKLT
116617985   626  .SFAWYNVKKSIWQVDQGDYNLKIGSSSR..DIRLEKTVS
116494248   628  .AFKEWREQTQTWVLPEAQKAIAVGTSVTNIDAVLPVSFT
66851551    792  LATSWWDEQREKWASEKGTYEVLVTGTGD...........
```

FIG 23D

```
125973771    668  ............................VNSTVKIR.KR
RAAC03001    660  ............................VTSAAPRRPVS
116334524    659  ........................MDFKNSP.APITTET
116617985    663  ........................LEMGTTNNRPISGDT
116494248    667  GETFNNFATIPNWYTTLSGKPSVQDFEQLTDQKVPAPHEF
66851551     821  .......................................
```

```
125973771    678  FTVNSAVEDVMSDSSAAAVLGPVLKEITDALQID....MD
RAAC03001    671  VHANAALGDLLDDPATGPVLRELLKEKLADSPLG....SE
116334524    673  YMAAIVKNPQLRDLFKQVVLAPEYAGPENFLAIT...DDQ
116617985    678  YISEIIN....RDGLHESLVASGLQTAIESISAS...DSN
116494248    707  VPGEFTRLNTPREMKKHSLLLRLVAWITVKIRTKDYIDKQ
66851551     821  .................EVLKSSFEVEKTRYWLGL
```

```
125973771    714  N.AHDMMAANIKNMPLR...SLVGYSQGRLSEEMLEELVD
RAAC03001    707  MDANPMFEAFMRFTPIGRVTTLFGVPRD.ENERVLAKLRA
116334524    710  GSLQIFQDRMFMNMPLR...AVVALGG...PQALITDFIT
116617985    711  R.......ELMENLPLR...AIIMIGA...NVDQVNKFIE
116494248    747  GPEAKFQQAIVLDTPLI...RLAQQASGALKLSMVDRLVA
66851551
```

```
125973771    750  KINNVE
RAAC03001    746  AQEEGQPEEGRG
116334524    744  RANTLLRQ
116617985    738  LANN
116494248    784  AANHQYVKMIFR
66851551
```

FIG 24A

| | | |
|---|---|---|
| RAAC02913 | 1 | MTTRLWRHPNPRVMRMEGCLMKPRQLALGLCAGACAWMFG |
| 15614969 | 1 | MKKILIHGCVFAIILLMTYGAVQNPFSSQYI |
| 124523066 | 1 | MNKAKR.LIALGLIAILALLLAGNPLSTRYL |
| 114843671 | 1 | MKIFYIKYPKKSFWIIFSLAILLLI |
| 89101184 | 1 | MKKLAG....MLLIGAFSLMLVNNPFTDLYV |
| 2634042 | 1 | MYKKFVPFAVFLFLFFVSFEMMENPHALDYI |
| | | |
| RAAC02913 | 41 | AGLWIRADAPPQPTPAPSERVWEEVSRAWANPPIDARRDR |
| 15614969 | 32 | GQLKEEALPVAKMTDSLYEEIKDRAPE.YEQPAIDAKIDR |
| 124523066 | 31 | ....QERAAFSTKENELQEKIEQAAER.FYRPPENAKIDR |
| 114843671 | 26 | FLIYIITRSVS............................ |
| 89101184 | 28 | SQLKMDSLAVTAESDSLLQRIEKESEN.YYIAPQDARIDP |
| 2634042 | 32 | GAMKKDTVTVTASKDPLYEELLQKAPE.YEVKPQNARIDK |
| | | |
| RAAC02913 | 81 | VWHNIPGLSGFALDTAASERETARF.HDGALHLVWRTVPP |
| 15614969 | 71 | VWKAIPGYNGLEVDVESSYNRMKQEGRFDERYLVFRETKP |
| 124523066 | 66 | VWKAIPGYNGVEVDKKASYSKMKQDGRYDERKLVFKQIPP |
| 114843671 | 37 | ............................VFNSNEP |
| 89101184 | 67 | VWKAIPGYNGVKVDVEASYKKMKGEKKFDPDKLVLEQIEP |
| 2634042 | 71 | VWKSIPGYNGLKVNIEQSYKKMKQHGKFREKDLVYSQVKP |
| | | |
| RAAC02913 | 120 | RVRLRDLPPDVIYRGPAEEKSVALMVNVSWGEAYVPRMLQ |
| 15614969 | 111 | SVHLDDLPPSPVFRGNPEKPMVTLLVNVAWGNEHLPTMLK |
| 124523066 | 106 | AVHLKDLDPAPVYTGNPDKPMVAFLINVAWGNEYLPDMLK |
| 114843671 | 44 | ..........IYKGDTKEKKIAFACNVAWGDEYIPKMLD |
| 89101184 | 107 | EKKLGDLPPAPIYKGNPDKPMVSFIINVAWGNEYLSGMLA |
| 2634042 | 111 | SVHLESLQPEPIYKGNPDKPMVAFLINVAWGNEYLEKMLP |
| | | |
| RAAC02913 | 160 | ILRDAHVKATFFVDGAWAKKFPDLVRAMAQDGHAVESHGS |
| 15614969 | 151 | TMNKYDVKSTFFLDGSWVKKHPQLATMIVEEGHEIGNHAY |
| 124523066 | 146 | TLKKHHLHATFFLEGRWAKENPELARMIVSGGHETGNHSY |
| 114843671 | 73 | IFKDNNIHITFFFEGKWAEKNPDVVKDIYQKGHEIGSHGY |
| 89101184 | 147 | TLKKHKVTATFFLEGRWVQQNPELAKMITEAGHEAGNHSF |
| 2634042 | 151 | ILQKHQVKATFFLEGNWVRNNVQLAKKIAKDGHEIGNHSY |
| | | |
| RAAC02913 | 200 | GHPDFRRLNDAKLAAQIDETNRVLAAITGRAPRLIAPPAG |
| 15614969 | 191 | SHPDMQRLTRERMDEEIVQTNEVIKATIEVTPKWFAPPSG |
| 124523066 | 186 | THPDFSTLPESKIKSQLVKTNRVLEAITEEKVKWFAPPSG |
| 114843671 | 113 | THVKYTNLSRQQYEEDIKKSGEILEKITGTKPTLFAPPYG |
| 89101184 | 187 | THPDMKTISSARIREEIEKTNQVIKATTGQEVTWFAPPSG |
| 2634042 | 191 | NHPDMSKLTTGRISEQLDKTNEQIEQTIGVKPKWFAPPSG |
| | | |
| RAAC02913 | 240 | SYDARLAPLAKSRGMYAILWTADTVDWKNPPPAAIVERVQ |
| 15614969 | 231 | SYNDLVVQRAAEHGMRTIMWSVDTIDWRNPDPNEMVDRVL |
| 124523066 | 226 | SYRDEAVSIAKSMGMETIMWTVDTVDWQNPSPETIVERVT |
| 114843671 | 153 | DFNDEVVKVAEQLGYKVILWSLDTIDWNNPSPQTIVDRVM |
| 89101184 | 227 | SYRDETVRIAAEKKLKTVMWSLDTVDWRKPSPEELLNRVV |
| 2634042 | 231 | SFRKAVIDIAAEKQMGTVMWTVDTIDWQKPAPSVLQTRVL |

FIG 24B

```
RAAC02913   280 RGAEPGALVLMHPTASTVEALPVMIRWLEARGYRMKTVED
15614969    271 SKVHPGAMILMHPTESSAAGLENLIRGIQDRGLHIGTVSD
124523066   266 AKAQGGSLILMHPTASTAKALEPLIARLEKKNLQVGTVSK
114843671   193 TKYHNGAIVLMHPTQNTVEALPQIIKQLKEKGYKITKVSE
89101184    267 PKVHNGAIILMHPTDSTAKSLDSMITQIKGKDFEIASVSR
2634042     271 SKIHNGAMILMHPTDPTAESLEALITQIKDKGYALGTVTE

RAAC02913   320 VIDERPAVTPPTILARETIRL
15614969    311 LMDESRINAGVTP
124523066   306 LLDEERIIKNEDGTFLNSEKDPADTKDGTE
114843671   233 VIVDNN
89101184    307 LLSEERIMDKK
2634042     311 LMDETRLLK
```

FIG 25A

```
595264      1                                    MNELIPL
20803949    1                                    MRRLDDR
17380381    1                                    MKHLDYI
128438      1                                    MKRPAYM
1001913     1                                    MKNLNII
RAAC02839   1   MFDASYIHRGDLCGREGRHVSRRMGSALIGLLAASSFVTY 595264      8   SAVRCNYGDVSGSRSVYLTFDDGPNPFCTPLVLDVLTQHR
20803949    8   WEVQSECADGTGRRSVYLTFDDGPNPCFTPQILDVLAQNR
17380381    8   HEVPSNCDYGTEDRSIYLTFDDGPNPHCTPEILDVLAEYG
128438      8   SEVPVNHTSGQEARCVYLTFDDGPNPFCTPQILDVLAEHR
1001913     8   DSVDVDAG..ADDPCVYLTFDDGPNPFCTPHILDVLAQHA
RAAC02839   41  GTPIVHATPSGQAKVVYLTFDDGPSQRYTPKLLDILRNQH 595264      48  VPATFFVIGTYAADQPELIRRMIAEGHEVANHTMTHPDLS
20803949    48  VPATFFVIGAYAAEHPDLIQRMIAEGHEVGNHTMSHPDLS
17380381    48  VPATFFVIGTYAKSQPELIRRIVAEGHEVANHTMTHPDLS
128438      48  VPATFFAIGSYVKDHPELIRRLVAEGHDVANHTMTHPDLA
1001913     46  VSATFFVIGANAEVHPGLVQRIVSEGHGVANHTMTHPDLA
RAAC02839   81  ISATFFVVGYRCEQFPDIVRRIQREGHEIGNHGFSHLDPK 595264      88  RCEAAEIHDEVLTASRAIRLACPQALPRHMRAPYGIWTED
20803949    88  KCGLGEVQREVFEANQAIMLACPQASIRYIRAPYGAWSEE
17380381    88  TCGPHEVEREIVEASEAIIAACPQAAVRHIRAPYGVWSEE
128438      88  TCDPKDVKREIDEAHQAIVSACPQALVRHLRAPYGVWTED
1001913     86  TCSRPQVEREIDEANRAIISACPGASIRHIRAPYGKWTEE
RAAC02839   121 KHALEEFILDIRKTDTAVVKACG.TKPLYYRPPYGSIDAS 595264      128 VLATSAKAGLAAVHWSVDPRDWSRPGVDSIVKSVLAAVRP
20803949    128 VLTASEIAGLAALHWSIDPRDWSRPGTDAIVDAVLASVRP
17380381    128 ALTRSASAGLTAIHWSADPRDWSRPGANAIVDAVLDSVRP
128438      128 VLSASVRAGLGAVHWSADPRDWSCPGVDVIVDEVLAAARP
1001913     126 ALVKSASLGLAPVHWSVDPRDWSCPGVDAIVDRVLAAAKP
RAAC02839   160 EIDCVHKLGHPIALWTVDSMDWKAKSANAIVSQVERHAQP 595264      168 GAIVLLHDGYPPGEEASCIDS...............TSREQ
20803949    168 GAIVLLHDGCPPDESTRSTQA...............SLRNQ
17380381    168 GAIVLLHDGCPPD..ESGALT...............GLRDQ
128438      168 GAIVLLHDGCPPDEVEQCSLA...............GLRDQ
1001913     166 GSIVLLHEDGPPGAADPTKLP...............TLRDQ
RAAC02839   200 GSIILFHDGISSSRYTIEAMPRIIRDFRRDGYTFKTLPIR 595264      194 TVRALAYLIPALQLRGFEIHPLPQLH
20803949    194 TVMALSNLIPALDACGYEIRSLPEHH
17380381    192 TLMALSRIVPALHERGFAIRPLPPHH
128438      194 TLIALSRIIPALHSRGFEIRSLP
1001913     192 TLAAISAIIKSLRSRGLTIRSLP
RAAC02839   240 DSLRIEAFVPKTDDDAILPRDTHDVQRKHRPSVGTRCIGR
```

FIG 25B

```
595264
20803949
17380381
128438
1001913
RAAC02839    280 QSRD
```

FIG 26A

| | | |
|---|---|---|
| RAAC00961 | 1 | MGVVHPRVGHAVPHHLWPQSSTGAPLLRDSERARPRVRVY |
| 124523411 | | |
| 15806097 | | |
| 21219643 | | |
| 13475158 | | |
| 21219455 | | |

| | | |
|---|---|---|
| RAAC00961 | 41 | QRDREVHGDGGSHRHEAGRADADGVHRDAPAPPHLSADSR |
| 124523411 | | |
| 15806097 | | |
| 21219643 | | |
| 13475158 | | |
| 21219455 | | |

| | | |
|---|---|---|
| RAAC00961 | 81 | SGGGECAVRRAGGCGGVREVSGGSSGVLALGARRPVHPEP |
| 124523411 | | |
| 15806097 | | |
| 21219643 | | |
| 13475158 | | |
| 21219455 | | |

| | | |
|---|---|---|
| RAAC00961 | 121 | HARGVQRDAELWRGGAHRAKDHAVCHEEASVPLRVAGVAA |
| 124523411 | | |
| 15806097 | | |
| 21219643 | 1 | MNRPEAPR |
| 13475158 | | |
| 21219455 | | |

| | | |
|---|---|---|
| RAAC00961 | 161 | RASSDVRGSAVIGWLVAVVLAVLVVYAGLPFVWTRGLGRS |
| 124523411 | 1 | MEVIIWVLILFILIYAIIPYVLAAKLGFW |
| 15806097 | 1 | MKRGVRGLLLGAALYIGLPYLLVQVGNLG |
| 21219643 | 9 | TRHGFPTGRAVYAVAPVVAAALAHIGPAATWLPELRRRRF |
| 13475158 | 1 | MRRLDDRWKVQSE |
| 21219455 | 1 | MR........SEP |

| | | |
|---|---|---|
| RAAC00961 | 201 | CIRRTPKP.GCVALTFDDGPHPVYTPRLLNALREAGARAT |
| 124523411 | 30 | VCWKGKKD.AEIALTFDDGPDPVYTPVLLDLLKRERIKAT |
| 15806097 | 30 | LVREGRRARREVALTFDDGPDPQTTPAVLAALREADMHAT |
| 21219643 | 49 | PGLAGRGSPGHVALTFDDGPDPASTPRFLDTLDGLGVRAT |
| 13475158 | 14 | CADGTGR..RSVYLTFDDGPNPCFTPQILDVLAQNRVPAT |
| 21219455 | 6 | ILRMTGRG.RTMLLTFDDGPHPEYTPKILDTLAKYEVRAT |

| | | |
|---|---|---|
| RAAC00961 | 240 | FFVIAEHALRHPEIVERMLAEGHEVQVHGYRHWFVPLLPP |
| 124523411 | 69 | FFLVGERAARYPELVLRMSREGHCIGLHNYKQCNWLISP |
| 15806097 | 70 | FFVIAGKAQAHPDLIRQMLEEGHEVEAHADKHVHAWIRTP |
| 21219643 | 89 | FFVLGENALRHPALTRELVRRGHELAVHGWTHDRPWWPSP |
| 13475158 | 52 | FFVIGAYAAEHPELIQRMIAEGHEVGNHTMSHPDLSKCGL |
| 21219455 | 45 | FFVCGEMADYNRDLLTRMADEGHVVGNHTWSHPLLTKLTR |

FIG 26B

```
RAAC00961   280  GLTARQCVGARDILAQRFGIDP.RVYRPTWGACNLATLVM
124523411   109  WKNARTLEQSARIIENITGERP.VFYRPPWGMMHLLDFFL
15806097    110  WGAALDPLRAVRAVG.AMTGRPVRFHRPPHGAYTLSTWLG
21219643    129  ARDTRELLRAVRVVDEVSGRAP.RWYRPPYGILTSGRWAA
13475158     92  GEVQREVFEANQAIMLACPQASIRYIRAPYGAWSEEVFTA
21219455     85  RRIRSEMERTSEVVEQAYGEAP.RWFRAPYGAWNRAAFQL

RAAC00961   319  LRRSRMSMLLWSVMVGDWRRTP.PEELARRILAKLDARSV
124523411   148  HK..QFRMVHWSKMFRDWKRKGGSKKVSNGLITRVESGDV
15806097    149  QRLAGVRGAHWSIEGCDWHPESIPDTVRERLAALLVPGAV
21219643    168  ARRAGLRPVLWTAWGKDWRHDATPASVRATVAADLCGGGT
13475158    132  SEIAGLAALHWSIDPRDWSRPG.TDAIVDAVLASVRPGAI
21219455    124  GSELGMEPLAWTVDTLDWTTPG.TGTIVDRVEEGAAPGVV

RAAC00961   358  IVLHDSDESP....GAERGAPESVIAAIPAVVEEVRRRGY
124523411   186  ILLHDCGVTP....GADEDAPQYTIEGLRVAIPALKARGF
15806097    189  IVLHDAGPG..........ARVTVPLLPSLLADLKARGY
21219643    208  VLLHDTDHAS......APGSWRATLGALPDIVRDCREAGL
13475158    171  VLLHDGCPPDESTRSTQASLRNQTVMALSNLIPALDACGY
21219455    163  VLSHDAGGD..........RSQSVRALRRYLPELLDSGY

RAAC00961   394  TFVLASECE
124523411   222  RFVRMDEMFDKHFSIKTSHRRKEIEP
15806097    218  RSVTLAELGGAAPQDWPGLKRRGFLALDAVFDRLGHIHFA
21219643    242  AVGPLGEHGAGGATGTPGTAAVAGTAGTAGTAASFRSPAP
13475158    211  EIRSLPEHH
21219455    192  HL.TVPRRRLI

RAAC00961
124523411
15806097    258  GGRADNLFRIARVPFPLEGARLADGTPIPHGAPALEFHVN
21219643    282  G
13475158
21219455

RAAC00961
124523411
15806097    298  NPILVDLGPRASVRQARREDFRVVARELQTRPEYADVGYV
21219643
13475158
21219455

RAAC00961
124523411
15806097    338  FCLSAVSPLLGLLGFENHDLPAADARRLRRWANVLRRAYG
21219643
13475158
21219455
```

FIG 26C

```
RAAC00961
124523411
15806097    378 NDPNAKAPRLSVLTREEFLALYGS
21219643
13475158
21219455
```

FIG 27A

| | | |
|---|---|---|
| RAAC00361 | 1 | MFPTRGPESRQLLPTARSRPPRSPPARGPRALLRSRPLQR |
| 52078651 | | |
| 16077225 | | |
| 89100305 | | |
| 15612806 | | |
| 121535454 | | |

| | | |
|---|---|---|
| RAAC00361 | 41 | AKKRLRERLVSLVRRMNRIAEQAQIPELPTSVVLDIGRLV |
| 52078651 | | |
| 16077225 | | |
| 89100305 | | |
| 15612806 | | |
| 121535454 | | |

| | | |
|---|---|---|
| RAAC00361 | 81 | PAKRLVGLHHHEPVTKRDPADAIVVLLRHLLGQGEIRKGI |
| 52078651 | 1 | MNHFYVWHIKRIKQLIIIM |
| 16077225 | 1 | MNHFYVWHIKRVKQLIIIL |
| 89100305 | 1 | MNFFYVVNGKAIKQGLLIM |
| 15612806 | 1 | MKFFWVLRAKKIKQLTIIL |
| 121535454 | 1 | MIVDLRRFMGHRHLFFGI |

| | | |
|---|---|---|
| RAAC00361 | 121 | VEGRNTERAVRAFAPFHQALHVLLRAAHDVLNEIGSPRED |
| 52078651 | 20 | IAA..................................... |
| 16077225 | 20 | IAA..................................... |
| 89100305 | 20 | IAS..................................... |
| 15612806 | 20 | LTA..................................... |
| 121535454 | 19 | IG...................................... |

| | | |
|---|---|---|
| RAAC00361 | 161 | RRRASQEIVSADHERDDLGLLDDTGREVLKRFEQLPRRPP |
| 52078651 | 23 | ........................................ |
| 16077225 | 23 | ........................................ |
| 89100305 | 23 | ........................................ |
| 15612806 | 23 | ........................................ |
| 121535454 | 21 | ........................................ |

| | | |
|---|---|---|
| RAAC00361 | 201 | RLRLDMQRRADLAGEAGAKALRKALLRRTRTVAICNGVAE |
| 52078651 | 23 | ........................................ |
| 16077225 | 23 | ........................................ |
| 89100305 | 23 | ........................................ |
| 15612806 | 23 | ........................................ |
| 121535454 | 21 | ........................................ |

| | | |
|---|---|---|
| RAAC00361 | 241 | REHQHDHRLLGESLIVSYGLSRRLVTRGAHAPVARSHRRC |
| 52078651 | 23 | ........................................ |
| 16077225 | 23 | ........................................ |
| 89100305 | 23 | ........................................ |
| 15612806 | 23 | ........................................ |
| 121535454 | 21 | ........................................ |

FIG 27B

| | | |
|---|---|---|
| RAAC00361 | 281 | GRCKHCRQNHKGGWPMRSFWKRLRAGVAALTAACVCAVSC |
| 52078651 | 23 | ...............................FATASF |
| 16077225 | 23 | ...............................FAAASF |
| 89100305 | 23 | ...............................FFTAWF |
| 15612806 | 23 | ...............................FFCASL |
| 121535454 | 21 | ...............................IFAIST |

| | | |
|---|---|---|
| RAAC00361 | 321 | MSLQAGSVRAADTKAQAPKAVYKVDTKEKVVALTFDISWG |
| 52078651 | 29 | FYVQNLLPLPVFSTEGGAKAVYRGDSDTNEVALTFNISWG |
| 16077225 | 29 | FYIQRAVPLPVFSTDTGPKAIYKGETDSKDISLTFDISWG |
| 89100305 | 29 | LYMENIIHMPVFSANDGPKAIYKGE...KDAALTFNIGWG |
| 15612806 | 29 | LYLERS.HLMVFSTPEGPQAFHKAETDEKVAALTFNISWG |
| 121535454 | 27 | LYVQAANIIAG.....GPIAIAGTNTDHKVVALTFDHSWG |

| | | |
|---|---|---|
| RAAC00361 | 361 | HRTPEPVLETLKKCGVTKATFFLSGPWTMHHPEIAKKIKA |
| 52078651 | 69 | DQKAMPILDTLKANGIKDATFFLSASWAERHPDVVERIRK |
| 16077225 | 69 | DERAEPILNTLKANGIKNATFFLSASWAERHPDTVARIVK |
| 89100305 | 66 | DEKAEPILDVLKKQNVKAATFFLSGSWAERHPELVARIVK |
| 15612806 | 68 | EQRVKPIIDVLQSKKVEEATFFISASWAERHPELVELIQE |
| 121535454 | 62 | NKFTPSILDTLKRHNL.KVTFFIMGPWAKKYPEVAQRMVA |

| | | |
|---|---|---|
| RAAC00361 | 401 | MGYEIGSHGYLHKDYSNYPDSWIREQAMLADKAIQQVTGV |
| 52078651 | 109 | DGHQIGSMGYAYKNYSQMKKSEIKKDLAKARHSFQKLGLD |
| 16077225 | 109 | DGHQIGSMGYAYKNYANLESSEIKKDMNRAQTAFEKLGVK |
| 89100305 | 106 | EGYEIGMLGYDYKDYTDLEESKIRQDLAKGQEAFKKLNVK |
| 15612806 | 108 | AGYHIGSHGYQYKNYTTWEDEKIRKDLRQSQQVISSITGE |
| 121535454 | 101 | DGHEIASHGYRHENYGDMTTEWVKEDILKAHALIKEVTGV |

| | | |
|---|---|---|
| RAAC00361 | 441 | KPKLFRTPNGDLNLRVIRCLTSMGYTVVQWNTDSLDWKNP |
| 52078651 | 149 | DLTLLRPPTGQFNKDVLDVAKQYGYTVVHYSINSDDWTNP |
| 16077225 | 149 | DIQLLRPPTGQFNKVLKVAKQYNYTVVHYSVNSQDWTNP |
| 89100305 | 146 | DIKLVRAPTGHFDQKTLNVAEKMGYTVVHWSIDSKDWTNP |
| 15612806 | 148 | KPTLLRPPNGDFDKRVLNLAESYDYTVVHWSINSRDYENP |
| 121535454 | 141 | DPTLIRPPNGHYSQRSLKAADELGYKTIIWNVDSLDWKNP |

| | | |
|---|---|---|
| RAAC00361 | 481 | GVDAIVNRVTKRVVPGDIVLMHASDSSKQIVEALPRIVEN |
| 52078651 | 189 | GVQKIVQNVNGTVNAGDIVLFHASDSAKQTKEALPEIVHH |
| 16077225 | 189 | GVEKIIDNVTKQVSGGDIILLHASDSAKQTEEALPDIIHQ |
| 89100305 | 186 | GVERIAENAAKAGK.GDIILLHASDSAKQTAKALPAIIGN |
| 15612806 | 188 | GVDAIVRQVVDHISPGDIVLMHASDSAKQTHKALPIIIDQ |
| 121535454 | 181 | GRDVIIERVMKRLKPGAIILMHASDTPVQTAEALPILLEK |

| | | |
|---|---|---|
| RAAC00361 | 521 | LRQQGYRFVTVSELLAGANVQSKVQ |
| 52078651 | 229 | LRSKGLKNVTVSELIANTDAKSSEVK |
| 16077225 | 229 | LKEKGLKNVTVGDLIANSDAKSAEVK |
| 89100305 | 225 | YKDKGLKLVSVSEMMANASTKSNEIK |
| 15612806 | 228 | LKGKGYHFRSIEELMADAHPTHDEIK |
| 121535454 | 221 | IKAEGYQIVTVSELLSKYSEKGIQRH |

THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS

RELATED APPLICATIONS

This application is a divisional of U.S. patent application Ser. No. 12/322,359, filed Jan. 29, 2009, issued Dec. 28, 2010, as U.S. Pat. No. 7,858,353, which application claims the benefit of the filing date of U.S. Provisional Patent Application Ser. No. 61/025,136, filed Jan. 31, 2008, for "THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS," the entire disclosure of each of which is hereby incorporated herein by this reference.

GOVERNMENT RIGHTS

This invention was made with government support under Contract Number DE-AC07-99ID13727 and Contract Number DE-AC07-05ID14517 awarded by the United States Department of Energy. The government has certain rights in the invention.

STATEMENT ACCORDING TO 37 C.F.R. §1.52(e)(5)-SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "SEQ LIST III.ST25.txt," which is 1,829 KB and was created on Nov. 8, 2010.

TECHNICAL FIELD

The present invention relates generally to biotechnology. More specifically, the present invention relates to isolated and/or purified polypeptides and nucleic acid sequences encoding polypeptides from *Alicyclobacillus acidocaldarius* and methods for their use.

BACKGROUND

Dilute acid hydrolysis to remove hemicellulose from lignocellulosic materials is one of the most developed pretreatment techniques for lignocellulose and is currently favored (Hamelinck et al., 2005) because it results in fairly high yields of xylose (75% to 90%). Conditions that are typically used range from 0.1 to 1.5% sulfuric acid and temperatures above 160° C. The high temperatures used result in significant levels of thermal decomposition products that inhibit subsequent microbial fermentations (Lavarack et al., 2002). High temperature hydrolysis requires pressurized systems, steam generation, and corrosion resistant materials in reactor construction due to the more corrosive nature of acid at elevated temperatures.

Low temperature acid hydrolyses are of interest because they have the potential to overcome several of the above shortcomings (Tsao et al., 1987). It has been demonstrated that 90% of hemicellulose can be solubilized as oligomers in a few hours of acid treatment in the temperature range of 80° C. to 100° C. It has also been demonstrated that the sugars produced in low temperature acid hydrolysis are stable under those same conditions for at least 24 hours with no detectable degradation to furfural decomposition products. Finally, sulfuric acid typically used in pretreatments is not as corrosive at lower temperatures. The use of lower temperature acid pretreatments requires much longer reaction times to achieve acceptable levels of hydrolysis. Although 90% hemicellulose solubilization has been shown (Tsao, 1987), the bulk of the sugars are in the form of oligomers and are not in the monomeric form. The organisms currently favored in subsequent fermentation steps cannot utilize sugar oligomers (Garrote et al., 2001) and the oligomer-containing hydrolysates require further processing to monomers, usually as a second acid or alkaline hydrolysis step (Garrote et al., 2001).

Other acidic pretreatment methods include autohydrolysis and hot water washing. In autohydrolysis, biomass is treated with steam at high temperatures (~240° C.), which cleaves acetyl side chains associated with hemicellulose to produce acetic acid that functions in a similar manner to sulfuric acid in acid hydrolysis. Higher pretreatment temperatures are required as compared to dilute acid hydrolysis because acetic acid is a much weaker acid than sulfuric. At temperatures below 240° C., the hemicellulose is not completely hydrolyzed to sugar monomers and has high levels of oligomers (Garrote et al., 2001). In hot water washing, biomass is contacted with water (under pressure) at elevated temperatures of 160° C. to 220° C. This process can effectively hydrolyze greater than 90% of the hemicellulose present and the solubilized hemicellulose was typically over 95% in the form of oligomers (Liu and Wyman, 2003).

BRIEF SUMMARY OF THE INVENTION

Embodiments of the invention relate to purified and/or isolated nucleotide sequences of the genome of *Alicyclobacillus acidocaldarius*, or a homologue or fragment thereof. In one embodiment of the invention, the nucleotide sequence is selected from SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, 463 or a homologue or fragment thereof. In another embodiment of the invention, the homologue is selected from the group consisting of a nucleotide sequence having at least 80% sequence identity to SEQ ID NOs:1, 18, 51, 68, 85, 101, 118, 135, 152, 167, 184, 201, 218, 235, 252, 269, 286, 303, 320, 336, 353, 370, 387, 404, 421, or 438; at least 93% sequence identity to SEQ ID NO:461; at least 94% sequence identity to SEQ ID NO:35; at least 96% sequence identity to SEQ ID NO:459; at least 99% sequence identity to SEQ ID NO:463; at least 99.6% sequence identity to SEQ ID NO:457; and at least 99.7% sequence identity to SEQ ID NO:455.

Embodiments of the invention may further relate to an isolated and/or purified nucleic acid sequence comprising a nucleic acid sequence encoding a polypeptide selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464;

at least 99.6% sequence identity to SEQ ID NO:458; and at least 99.7% sequence identity to SEQ ID NO:456.

Embodiments of the invention also relate to isolated and/or purified polypeptides encoded by a nucleotide sequence of the genome of *Alicyclobacillus acidocaldarius*, or a homologue or fragment thereof. In one embodiment, the nucleotide sequence is selected from the group consisting of a nucleotide sequence having at least 80% sequence identity to SEQ ID NOs:1, 18, 51, 68, 85, 101, 118, 135, 152, 167, 184, 201, 218, 235, 252, 269, 286, 303, 320, 336, 353, 370, 387, 404, 421, or 438; at least 93% sequence identity to SEQ ID NO:461, at least 94% sequence identity to SEQ ID NO:35; at least 96% sequence identity to SEQ ID NO:459; at least 99% sequence identity to SEQ ID NO:463; at least 99.6% sequence identity to SEQ ID NO:457; and at least 99.7% sequence identity to SEQ ID NO:455.

In another embodiment of the invention, the nucleotide sequence is selected from SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, 463 or a homologue or fragment thereof. In still another embodiment, the polypeptide has the amino acid sequence of SEQ ID NOs:2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464. In yet another embodiment, the polypeptide is selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464; at least 99.6% sequence identity to SEQ ID NO:458; and at least 99.7% sequence identity to SEQ ID NO:456.

In embodiments of the invention, the polypeptides may be acidophilic and/or thermophilic. In further embodiments, the polypeptides may be glycosylated, pegylated, and/or otherwise post-translationally modified.

Embodiments of the invention include methods of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups. Such methods may comprise placing a polypeptide selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464; at least 99.6% sequence identity to SEQ ID NO:458; and at least 99.7% sequence identity to SEQ ID NO:456 in fluid contact with a polysaccharide, lignocellulose, cellulose, hemicellulose, lignin, starch, chitin, polyhydroxybutyrate, heteroxylan, glycoside, xylan-, glucan-, galactan-, and/or mannan-decorating group.

These and other aspects of the invention will become apparent to the skilled artisan in view of the teachings contained herein.

BRIEF DESCRIPTION OF THE SEVERAL VIEWS OF THE DRAWINGS

FIGS. 1A and 1B depict a sequence alignment between SEQ ID NO:2 (RAAC00169), an esterase of the alpha-beta hydrolase superfamily, and gi|121533815, gi|89099582, gi|16078568, gi|15615150, and gi|124524344 (SEQ ID NOs: 3-7, respectively), which are all esterases of the alpha-beta hydrolase superfamily. Amino acids common to three or more of the sequences aligned are indicated in bold.

FIGS. 2A and 2B depict a sequence alignment between SEQ ID NO:19 (RAAC00501), an alpha beta hydrolase, gi|125974699, gi|15613871, gi|5457696, gi|14520481, and gi|40744233 and (SEQ ID NOs:20-24, respectively), which are all alpha beta hydrolases. Amino acids common to three or more of the sequences aligned are indicated in bold.

FIGS. 3A, 3B, and 3C depict a sequence alignment between SEQ ID NO:36 (RAAC00568), an alpha-glucosidase, and gi|6686567, gi|4586418, gi|89098051, and gi|14844717 (SEQ ID NOs:37-40, respectively), which are all alpha-glucosidases. Amino acids common to three or more of the sequences aligned are indicated in bold.

FIGS. 4A, 4B, and 4C depict a sequence alignment between SEQ ID NO:52 (RAAC00594) and gi|16131527, gi|52081844, gi|52787233, gi|16504867, and gi|16422318 (SEQ ID NOs:53-57, respectively), which are all alpha-xylosidases. Amino acids common to three or more of the sequences aligned are indicated in bold.

FIGS. 5A and 5B depict a sequence alignment between SEQ ID NO:69 (RAAC00602), an alpha-L-arabinofuranosidase, and gi|6079924, gi|89095985, gi|15614424, gi|52081375, and gi|52786751 (SEQ ID NOs:70-74, respectively), which are all alpha-L-arabinofuranosidases. Amino acids common to three or more of the sequences aligned are indicated in bold.

FIGS. 6A and 6B depict a sequence alignment between SEQ ID NO:86 (RAAC00798), a cell wall-associated hydrolase, and gi|15893601, gi|15896196, gi|15893600, and gi|16513351 (SEQ ID NOs:87-90, respectively), which are all cell wall-associated hydrolases. Amino acids common to three or more of the sequences aligned are indicated in bold.

FIGS. 7A and 7B depict a sequence alignment between SEQ ID NO:102 (RAAC01076), an altronate hydrolase, and gi|15613053, gi|121533397, gi|52081816, gi|52787203, and gi|15893984 (SEQ ID NOs:103-107, respectively), which are all altronate hydrolases. Amino acids common to three or more of the sequences aligned are indicated in bold.

FIGS. 8A and 8B depict a sequence alignment between SEQ ID NO:119 (RAAC01219) and gi|125973125, gi|76796625, gi|20515428, gi|114843317, and gi|76795342 (SEQ ID NOs:120-124, respectively), which are all cellulase/endoglucanase Ms. Amino acids common to three or more of the sequences aligned are indicated in bold.

FIGS. 9A and 9B depict a sequence alignment between SEQ ID NO:136 (RAAC01220) and gi|125973126, gi|20515429, gi|76796624, gi|114843316, and gi|15893508 (SEQ ID NOs:137-141, respectively), which are all cellulase/endoglucanase Ms. Amino acids common to three or more of the sequences aligned are indicated in bold.

FIG. 10 depicts a sequence alignment between SEQ ID NO:153 (RAAC01221), a cellulase/endoglucanase M, and gi|20515430, gi|76796623, gi|125973127, and gi|125973126 (SEQ ID NOs:154-156 and 137, respectively), which are all cellulase/endoglucanase Ms. Amino acids common to three or more of the sequences aligned are indicated in bold.

FIGS. 11A-11C depict a sequence alignment between SEQ ID NO:168 (RAAC01275), a polygalacturonase, and gi|89098529, gi|116623151, gi|116620373, gi|52081815, and gi|52787202 (SEQ ID NOs:169-173, respectively), which are all polygalacturonases. Amino acids common to three or more of the sequences aligned are indicated in bold.

FIGS. 12A-12C depict a sequence alignment between SEQ ID NO:185 (RAAC01615), an alpha-galactosidase, and gi|15614786, gi|90961985, gi|148544139, gi|76796346, and gi|114844315 (SEQ ID NOs:186-190, respectively), which are all alpha-galactosidases. Amino acids common to three or more of the sequences aligned are indicated in bold.

FIGS. 13A-13K depict a sequence alignment between SEQ ID NO:202 (RAAC01621), a cellobiose phosphorylase, and gi|125973736, gi|114844102, gi|20517160, 0176795700, and gi|118725340 (SEQ ID NOs:203-207, respectively), which are all cellobiose phosphorylases. Amino acids common to three or more of the sequences aligned are indicated in bold.

FIGS. 14A-14C depict a sequence alignment between SEQ ID NO:219 (RAAC01755) and gi|15616253, gi|89099466, gi|17227827, gi|72163378, and gi|13470878 (SEQ ID NOs: 220-224, respectively), which are all glycogen debranching enzymes. Amino acids common to three or more of the sequences aligned are indicated in bold.

FIGS. 15A and 15B depict a sequence alignment between SEQ ID NO:236 (RAAC01887), a cellulase/endoglucanase M, and gi|52081384, gi|124521982, gi|89098880, gi|121533826, and gi|15615819 (SEQ ID NOs:237-240, respectively), which are all cellulase/endoglucanase Ms. Amino acids common to three or more of the sequences aligned are indicated in bold.

FIGS. 16A and 16B depict a sequence alignment between SEQ ID NO:253 (RAAC01897), an acetyl esterase/acetyl hydrolase, and gi|21221842, gi|13470513, gi|13471782, gi|16329563, and gi|15600577 (SEQ ID NOs:254-258, respectively), which are all acetyl esterase/acetyl hydrolases. Amino acids common to three or more of the sequences aligned are indicated in bold.

FIGS. 17A and 17B depict a sequence alignment between SEQ ID NO:270 (RAAC01917), a beta-1,4-xylanase, and gi|14054545, gi|134266943, gi|39654242, gi|61287936, and gi|3201483 (SEQ ID NOs:271-275, respectively), which are all beta-1,4-xylanases. Amino acids common to three or more of the sequences aligned are indicated in bold.

FIGS. 18A and 18B depict a sequence alignment between SEQ ID NO:287 (RAAC02404), a cinnamoyl ester hydrolase, and gi|76796576, gi|114845181, gi|15896898, gi|5806073, and gi|58448090 (SEQ ID NOs:288-292, respectively), which are all cinnamoyl ester hydrolases. Amino acids common to three or more of the sequences aligned are indicated in bold.

FIGS. 19A and 19B depict a sequence alignment between SEQ ID NO:304 (RAAC02424), a carboxylesterase type B, and gi|56421584, gi|134105165, gi|124521931, gi|33311865, and gi|138896639 (SEQ ID NOs:305-309, respectively), which are all carboxylesterase type Bs. Amino acids common to three or more of the sequences aligned are indicated in bold.

FIGS. 20A-20D depict a sequence alignment between SEQ ID NO:321 (RAAC02616), a beta galactosidase/beta-glucuronidase, and gi|29377189, gi|16493950, gi|40745013, and gi|49176308 (SEQ ID NOs:322-325, respectively), which are all beta galactosidase/beta-glucuronidases. Amino acids common to three or more of the sequences aligned are indicated in bold.

FIGS. 21A-21D depict a sequence alignment between SEQ ID NO:337 (RAAC02661), a xylan alpha-1,2-glucuronidase, and gi|15613624, gi|118725970, gi|148270004, gi|15642830, and gi|116621784 (SEQ ID NOs:338-342, respectively), which are all xylan alpha-1,2-glucuronidases. Amino acids common to three or more of the sequences aligned are indicated in bold.

FIGS. 22A-22C depict a sequence alignment between SEQ ID NO:354 (RAAC02925), a 3-hydroxyisobutyryl-CoA hydrolase, and gi|52080473, gi|17552962, gi|15292329, gi|66851010, and gi|40739053 (SEQ ID NOs:355-359, respectively), which are all 3-hydroxyisobutyryl-CoA hydrolases. Amino acids common to three or more of the sequences aligned are indicated in bold.

FIGS. 23A-23D depict a sequence alignment between SEQ ID NO:371 (RAAC03001), a beta-glucosidase B-related glycosidase, and gi|125973771, gi|116617985, gi|116494248 gi|116334524, and gi|66851551 (SEQ ID NOs:372-376, respectively), which are all beta-glucosidase B-related glycosidases. Amino acids common to three or more of the sequences aligned are indicated in bold.

FIGS. 24A and 24B depict a sequence alignment between SEQ ID NO:388 (RAAC02913), a chitooligosaccharide deacetylase, and gi|15614969, gi|124523066, gi|114843671 gi|89101184, and gi|2634042 (SEQ ID NOs:389-393, respectively), which are all chitooligosaccharide deacetylases. Amino acids common to three or more of the sequences aligned are indicated in bold.

FIGS. 25A and 25B depict a sequence alignment between SEQ ID NO:405 (RAAC02839), a chitooligosaccharide deacetylase, and gi|595264, gi|20803949, gi|7380381 gi|128438, and gi|1001913 (SEQ ID NOs:406-409, respectively), which are all chitooligosaccharide deacetylases. Amino acids common to three or more of the sequences aligned are indicated in bold.

FIGS. 26A-26C depict a sequence alignment between SEQ ID NO:422 (RAAC00961), a chitooligosaccharide deacetylase, and gi|124523411, gi|158060979, gi|21219643 gi|13475158, and gi|21219455 (SEQ ID NOs:423-427, respectively), which are all chitooligosaccharide deacetylases. Amino acids common to three or more of the sequences aligned are indicated in bold.

FIGS. 27A and 27B depict a sequence alignment between SEQ ID NO:439 (RAAC00361), a chitooligosaccharide deacetylase, and gi|52078651, gi|16077225, gi|89100395 gi|15612806, and gi|121535454 (SEQ ID NOs:440-444, respectively), which are all chitooligosaccharide deacetylases. Amino acids common to three or more of the sequences aligned are indicated in bold.

DETAILED DESCRIPTION OF THE INVENTION

Lignocellulose is a highly heterogeneous three-dimensional matrix comprised primarily of cellulose, hemicellulose, and lignin. Many fuels and chemicals can be made from these lignocellulosic materials. To utilize lignocellulosic biomass for production of fuels and chemicals via fermentative processes, it is necessary to convert the plant polysaccharides to sugar monomers, which are then fermented to products using a variety of microorganisms. Direct hydrolysis of lignocellulose by mineral acids to monomers is possible at high temperatures and pressures, leading to yield losses due to thermal decomposition of the sugars. Utilizing existing commercially available enzymes, a first strategy to reduce these yield losses is to perform the pretreatment at a reduced severity to produce soluble oligomers, followed by the use of cellulases and hemicellulases to depolymerize the polysaccharides at moderate temperatures. In a second approach, the addition of acid stable thermotolerant hydrolytic enzymes including cellulases, xylanases and other hemicellulases to the biomass slurry during the pretreatment allows the use of further reduced temperatures and pressures during the pretreatment, as well as cheaper materials of construction, reducing both the capital and energy costs. An extension of this second approach is to combine the enzyme-assisted reduced severity pretreatment together with fermentation under the same conditions, which further reduces costs.

For commercially available enzymes to be utilized, the first strategy must be used. The second approach represents a significant improvement in the art because the pretreatment and bioconversion of the polysaccharides to products can be achieved in fewer steps/vessels and without intermediately altering the process conditions.

Embodiments of the invention relate in part to the gene sequences and protein sequences encoded by genes of *Alicyclobacillus acidocaldarius*. Genes included are those necessary to depolymerize biopolymers including lignocellulosic polysaccharides, starches, chitin, polyhydroxybutyrate, and the like, to monomers or oligomers. Intracellular enzyme activities will be thermophilic in nature and general examples of similar genes are described in the literature. Extracellular enzyme activities will be thermoacidophilic (simultaneously thermophilic and acidophilic). The following classes of enzymes are included for polysaccharide depolymerization: glycosyl hydrolases (or glycoside hydrolases), esterases including acetylxylan esterases and p-cumaric acid esterases and ferulic acid esterases, and uronidases. An additional class of enzymes for biopolymer depolymerization includes polyhydroxybutyrate-degrading enzymes.

The present invention relates to isolated and/or purified nucleotide sequences of the genome of *Alicyclobacillus acidocaldarius* selected from the sequences SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments.

The present invention likewise relates to isolated and/or purified nucleotide sequences, characterized in that they are selected from: a) a nucleotide sequence of a specific fragment of the sequence SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and a nucleotide sequence modified by a nucleotide sequence such as defined in a), b), c), d) or e).

A "nucleotide, polynucleotide, or nucleic acid sequence" will be understood according to the present invention as meaning both a double-stranded or single-stranded DNA in the monomeric and dimeric (so-called "in tandem") forms and the transcription products of the DNAs.

Aspects of the invention relate to nucleotide sequences in which it has been possible to isolate, purify or partially purify, starting from separation methods such as, for example, ion-exchange chromatography, by exclusion based on molecular size, or by affinity, or alternatively, fractionation techniques based on solubility in different solvents, or starting from methods of genetic engineering such as amplification, cloning, and subcloning, it being possible for the sequences of the invention to be carried by vectors.

An "isolated and/or purified nucleotide sequence fragment" according to the invention will be understood as designating any nucleotide fragment of the genome of *Alicyclobacillus acidocaldarius*, and may include, by way of non-limiting example, a length of at least 8, 12, 20 25, 50, 75, 100, 200, 300, 400, 500, 1000, or more, consecutive nucleotides of the sequence from which it originates.

A "specific fragment of an isolated and/or purified nucleotide sequence" according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

A "homologous isolated and/or purified nucleotide sequence" in the sense of the present invention is understood as meaning an isolated and/or purified nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

A "specific homologous nucleotide sequence" in the sense of the present invention is understood as meaning a homologous nucleotide sequence having at least one nucleotide sequence of a specific fragment, such as defined above. The "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. The homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino acids or nucleotidic sequences are said to be "identical" if the sequence of amino acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well defined and only one value for the sequence identity between two compared sequences, which value corresponds to the value obtained for the best or optimal alignment.

In the BLAST N or BLAST P "BLAST 2 sequence," software that is available on the worldwide web at ncbi.nlm.nih.gov/gorf/b12.html, and habitually used by the inventors and in general by a skilled person for comparing and determining the identity between two sequences, gap cost, which depends on the sequence length to be compared, is directly selected by the software (i.e., 11.2 for substitution matrix BLOSUM-62 for length>85).

Complementary nucleotide sequence of a sequence of the invention is understood as meaning any DNA whose nucleotides are complementary to those of the sequence of the invention, and whose orientation is reversed (antisense sequence).

Hybridization under conditions of stringency with a nucleotide sequence according to the invention is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments as described above are advantageously obtained by the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example, a temperature of 37° C. in the presence of a 2×SSC buffer, respectively, require a globally less significant complementarity for the hybridization between the two sequences.

The stringent hybridization conditions described above for a polynucleotide with a size of approximately 350 bases will be adapted by a person skilled in the art for oligonucleotides of greater or smaller size, according to the teachings of Sambrook et al., 1989.

Among the isolated and/or purified nucleotide sequences according to the invention, are those that can be used as a primer or probe in methods allowing the homologous sequences according to the invention to be obtained, these methods, such as the polymerase chain reaction (PCR), nucleic acid cloning, and sequencing, being well known to a person skilled in the art.

Among the isolated and/or purified nucleotide sequences according to the invention, those are again preferred that can be used as a primer or probe in methods allowing the presence of SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463, one of their fragments, or one of their variants such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

"Modified nucleotide sequence" will be understood as meaning any nucleotide sequence obtained by mutagenesis according to techniques well known to a person skilled in the art, and containing modifications with respect to the normal sequences according to the invention, for example, mutations in the regulatory and/or promoter sequences of polypeptide expression, especially leading to a modification of the rate of expression of the polypeptide or to a modulation of the replicative cycle.

The modified nucleotide sequence will likewise be understood as meaning any nucleotide sequence coding for a modified polypeptide such as defined below.

The present invention relates to isolated and/or purified nucleotide sequences of *Alicyclobacillus acidocaldarius*, characterized in that they are selected from the sequences SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments.

Embodiments of the invention likewise relate to isolated and/or purified nucleotide sequences characterized in that they comprise a nucleotide sequence selected from: a) nucleotide sequences of SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID NOs:8-12, 25-29, 41-45, 58-62, 75-79, 91-95, 108-112, 125-129, 142-146, 157-161, 174-178, 191-195, 208-212, 225-229, 242-246, 259-263, 276-280, 293-297, 310-314, 326-330, 343-347, 360-364, 377-381, 394-398, 411-415, 428-432, or 445-449 or fragments thereof and any other isolated and/or purified nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or fragments thereof. The homologous sequences can comprise, for example, the sequences corresponding to the genomic sequences *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide.

Embodiments of the invention comprise the isolated and/or purified polypeptides encoded by a nucleotide sequence according to the invention, or fragments thereof, whose sequence is represented by a fragment. Amino acid sequences corresponding to the isolated and/or purified polypeptides can be encoded according to one of the three possible reading frames of the sequence SEQ ID NOs:1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463.

Embodiments of the invention likewise relate to the isolated and/or purified polypeptides, characterized in that they comprise a polypeptide selected from the amino acid sequences SEQ ID NOs:2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464 or one of their fragments.

Among the isolated and/or purified polypeptides, according to embodiments of the invention, are the isolated and/or purified polypeptides of amino acid sequence SEQ ID NOs: 13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454 or fragments thereof or any other isolated and/or purified polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID NOs:2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464 or fragments thereof.

Embodiments of the invention also relate to the polypeptides, characterized in that they comprise a polypeptide selected from: a) a specific fragment of at least five amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the invention, the isolated and/or purified polypeptides according to the invention may be glycosylated, pegylated, and/or otherwise post-translationally modified. In further embodiments, glycosylation, pegylation, and/or other post-translational modifications may occur in vivo or in vitro and/or may be performed using chemical techniques. In additional embodiments, any glycosylation, pegylation and/or other post-translational modifications may be N-linked or O-linked.

In embodiments of the invention, any one of the isolated and/or purified polypeptides according to the invention may be enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5, 4, 3, 2, 1, and/or 0. In further embodiments of the invention, glycosylation, pegylation, and/or other post-translational modification may be required for the isolated and/or purified polypeptides according to the invention to be enzymatically active at a pH at or below 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

Aspects of the invention relate to polypeptides that are isolated or obtained by purification from natural sources, or else obtained by genetic recombination, or alternatively, by chemical synthesis and, thus, they may contain unnatural amino acids, as will be described below.

A "polypeptide fragment" according to the embodiments of the invention is understood as designating a polypeptide containing at least five consecutive amino acids, preferably ten consecutive amino acids or fifteen consecutive amino acids.

In the present invention, a specific polypeptide fragment is understood as designating the consecutive polypeptide fragment encoded by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the invention.

"Specific homologous polypeptide" will be understood as designating the homologous polypeptides, such as defined above, and having a specific fragment of polypeptide according to the invention.

In the case of a substitution, one or more consecutive or nonconsecutive amino acids are replaced by "equivalent" amino acids. The expression "equivalent" amino acid is directed here as designating any amino acid capable of being substituted by one of the amino acids of the base structure without, however, essentially modifying the biological activities of the corresponding peptides, such that they will be defined by the following. Examples of such substitutions in the amino acid sequences of SEQ ID NOs:2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464 may include those isolated and/or purified polypeptides of amino acid sequence SEQ ID NOs:13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454.

These equivalent amino acids can be determined either by depending on their structural homology with the amino acids which they substitute, or on results of comparative tests of biological activity between the different polypeptides, which are capable of being carried out.

By way of nonlimiting example, the possibilities of substitutions capable of being carried out without resulting in an extensive modification of the biological activity of the corresponding modified polypeptides will now be mentioned, the replacement, for example, of leucine by valine or isoleucine, of aspartic acid by glutamic acid, of glutamine by asparagine, of arginine by lysine etc., the reverse substitutions naturally being envisageable under the same conditions.

In a further embodiment, substitutions are limited to substitutions in amino acids not conserved among other proteins which have similar identified enzymatic activity. For example, the figures herein provide sequence alignments between certain polypeptides of the invention and other polypeptides identified as having similar enzymatic activity, with amino acids common to three or more of the sequences aligned indicated in bold. Thus, according to one embodiment of the invention, substitutions or mutation may be made at positions that are not indicated as in bold in the figures. Examples of such polypeptides may include, but are not limited to, those found in the amino acid sequences of SEQ ID NOs:13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454. In a further embodiment, nucleic acid sequences may be mutated or substituted such that the amino acid they encode is unchanged (degenerate substitutions and/mutations) and/or mutated or substituted such that any resulting amino acid substitutions or mutation are made at positions that are not indicated as in bold in the figures. Examples of such nucleic acid sequences may include, but are not limited to, those found in are the nucleotide sequences of SEQ ID NOs:13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454 or fragments thereof.

The specific homologous polypeptides likewise correspond to polypeptides encoded by the specific homologous nucleotide sequences such as defined above, and thus comprise in the present definition the polypeptides that are mutated or correspond to variants that can exist in *Alicyclobacillus acidocaldarius*, and which especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, as having at least one of the characteristics of polypeptides according to the invention. In certain embodiments, the peptide is capable of acting as an Alpha beta hydrolase, Alpha-glucosidase, Glucan 1,4-alpha-maltohydrolase, Glycosidase, Amylase, Acetyl esterase, Beta-galactosidase, Alpha amylase, Acetyl esterase, Alpha-xylosidase, Cyclomaltodextrinase; Neopullulanase; Maltogenic alpha-amylase, Family 31 of glycosyl hydrolase, Alpha-L-arabinofuranosidase, Cell wall hydrolase, Altronate hydrolase, poly-1,4-alpha-D-galacturonide, Xylan alpha-1, 2-glucuronosidase, Cellulase/Endoglucanase M, Polygalacturonase, Glycosyl hydrolase, Peptidoglycan hydrolase, N-acetylglucosaminidase, Endochitinase, Alpha-galactosidase, Endo-beta-1,4-mannanase, Cellobiose phosphorylase, Cyclic beta-1,2-glucan synthase, Glycogen debranching enzyme, Acetyl hydrolase, Beta-1,4-xylanase, Beta-glucosidase, 6-phospho-beta-glucosidase, Cinnamoyl ester hydrolase, Beta-glucuronidase, Xylan alpha-1,2-glucuronosidase, 3-hydroxyisobutyryl-CoA hydrolase, Beta-glucosidase B-related glycosidase, and/or Chitooligosaccharide deacetylase.

The polypeptide fragments according to embodiments of the invention can correspond to isolated or purified fragments naturally present in an *Alicyclobacillus acidocaldarius* or correspond to fragments that can be obtained by cleavage of the polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, or from hosts transformed by an expression vector according to the invention containing a nucleic acid allowing the expression of the fragments and placed under the control of appropriate regulation and/or expression elements.

"Modified polypeptide" of a polypeptide according to an embodiment of the invention is understood as designating a polypeptide obtained by genetic recombination or by chemical synthesis, as will be described below, as having at least one modification with respect to the normal sequence. These modifications may or may not be able to bear on amino acids at the origin of specificity, and/or of activity, or at the origin of the structural conformation, localization, and of the capacity of membrane insertion of the polypeptide according to the invention. It will thus be possible to create polypeptides of equivalent, increased, or decreased activity, and of equivalent, narrower, or wider specificity. Among the modified polypeptides, it is necessary to mention the polypeptides in which up to five amino acids can be modified, truncated at the N- or C-terminal end, or even deleted or added.

The methods allowing modulations on eukaryotic or prokaryotic cells to be demonstrated are well known to the person of ordinary skill in the art. It is likewise well understood that it will be possible to use the nucleotide sequences coding for the modified polypeptides for the modulations, for example, through vectors according to the invention and described below.

The preceding modified polypeptides can be obtained by using combinatorial chemistry, in which it is possible to systematically vary parts of the polypeptide before testing them on models, cell cultures or microorganisms, for example, to select the compounds that are most active or have the properties sought.

Chemical synthesis likewise has the advantage of being able to use unnatural amino acids, or nonpeptide bonds.

Thus, in order to improve the duration of the life of the polypeptides according to the invention, it may be of interest to use unnatural amino acids, e.g., in D form, or else amino acid analogs, especially sulfur-containing forms, for example.

Finally, it will be possible to integrate the structure of the polypeptides according to the invention, its specific or modified homologous forms, into chemical structures of polypeptide types or others. Thus, it may be of interest to provide at the N- and C-terminal ends compounds not recognized by proteases.

The nucleotide sequences coding for a polypeptide according to the invention are likewise part of the invention.

The invention likewise relates to nucleotide sequences utilizable as a primer or probe, characterized in that the sequences are selected from the nucleotide sequences according to the invention.

It is well understood that the present invention, in various embodiments, likewise relates to specific polypeptides of *Alicyclobacillus acidocaldarius*, encoded by nucleotide sequences, capable of being obtained by purification from natural polypeptides, by genetic recombination or by chemical synthesis by procedures well known to a person skilled in the art and such as described in particular below. In the same manner, the labeled or unlabeled mono- or polyclonal antibodies directed against the specific polypeptides and encoded by the nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least eight nucleotides, preferably of at least twelve nucleotides, and even more preferentially at least twenty nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievits et al. in 1991; the SDA technique (Strand Displacement Amplification) (Walker et al., 1992); the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al., as well as by Stone et al. in 1996.

In the case where the target polynucleotide to be detected is possibly an RNA, for example an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least twelve nucleotides, in particular of at least twenty nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive element ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes that are utilizable for numerous applications.

Examples of nonradioactive labeling of nucleotide sequences are described, for example, in French Patent No. 7810975 or by Urdea et al. or by Sanchez-Pescador et al., both in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used by being immobilized on a support and can thus serve to capture, by specific hybridization, the target nucleic acid obtained from the biological sample to be tested. If necessary, the solid support is separated from the sample and the hybridization complex is formed between the capture probe. The target nucleic acid is then detected with the aid of a second probe, a so-called "detection probe," and labeled with an easily detectable element.

Another aspect of the present invention is a vector for the cloning and/or expression of a sequence, characterized in that it contains a nucleotide sequence according to the invention.

The vectors according to the invention, characterized in that they contain the elements allowing the expression and/or the secretion of the nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by a person skilled in the art, and it will be possible to introduce the clones resulting therefrom into an appropriate host by standard methods, such as, for example, lipofection, electroporation, and thermal shock.

The vectors, according to the invention, are, for example, vectors of plasmid or viral origin. One example of a vector for the expression of polypeptides of the invention is baculovirus.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector, such as defined above, and then the culturing of the cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example, Sf9 insect cells (Luckow, 1993).

Embodiments of the invention likewise relate to organisms comprising one of the transformed cells according to the invention.

The obtainment of transgenic organisms according to the invention overexpressing one or more of the genes of *Alicyclobacillus acidocaldarius* or part of the genes may be carried out in, for example, rats, mice, or rabbits according to methods well known to a person skilled in the art, such as by viral or nonviral transfections. It will be possible to obtain the transgenic organisms overexpressing one or more of the genes by transfection of multiple copies of the genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of the chimeras.

The transformed cells, as well as the transgenic organisms according to the invention, are utilizable in procedures for preparation of recombinant polypeptides.

It is today possible to produce recombinant polypeptides in a relatively large quantity by genetic engineering, for example, using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of the transformed cells according to the invention are themselves comprised in the present invention.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among the procedures for preparation of a polypeptide of the invention in recombinant form, the preparation procedures include employing a vector, and/or a cell transformed by the vector and/or a transgenic organism comprising one of the transformed cells, containing a nucleotide sequence according to the invention of coding for a polypeptide of *Alicyclobacillus acidocaldarius*.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of nucleotide sequence according to the invention; b) if need be, recovery of the recombinant polypeptide.

When the procedure for preparation of a polypeptide of the invention employs a transgenic organism according to the invention, the recombinant polypeptide is then extracted from the organism.

The invention also relates to a polypeptide which is capable of being obtained by a procedure of the invention, such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively, several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield in 1966.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated, pegylated, and/or otherwise post-translationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of gene coding for fusion proteins described by Minton in 1984.

The hybrid nucleotide sequences coding for a hybrid polypeptide, as well as the hybrid polypeptides according to the invention characterized in that they are recombinant polypeptides obtained by the expression of the hybrid nucleotide sequences, are likewise part of the invention.

The invention likewise comprises the vectors characterized in that they contain one of the hybrid nucleotide sequences. The host cells transformed by the vectors, the transgenic organisms comprising one of the transformed cells as well as the procedures for preparation of recombinant polypeptides using the vectors, the transformed cells and/or the transgenic organisms are, of course, likewise part of the invention.

The polypeptides according to the invention, the antibodies according to the invention, described below, and the nucleotide sequences according to the invention can advantageously be employed in procedures for the detection and/or identification of *Alicyclobacillus acidocaldarius*, in a sample capable of containing them. These procedures, according to the specificity of the polypeptides, the antibodies and the nucleotide sequences, according to the invention, which will be used, will in particular be able to detect and/or to identify an *Alicyclobacillus acidocaldarius*.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between the polypeptide and the antibodies possibly present in the biological sample); b) demonstration of the antigen-antibody complexes possibly formed.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological processes (RIA), or their equivalent.

Thus, the invention likewise relates to the polypeptides according to the invention, labeled with the aid of an adequate label such as of the enzymatic, fluorescent or radioactive type.

Such methods comprise, for example, the following steps: deposition of determined quantities of a polypeptide composition according to the invention in the wells of a microtiter plate, introduction into the wells of increasing dilutions of serum, or of a biological sample other than that defined previously, having to be analyzed, incubation of the microplate, introduction into the wells of the microtiter plate of labeled antibodies directed against pig immunoglobulins, the labeling of these antibodies having been carried out with the aid of an enzyme selected from those that are capable of hydrolyzing a substrate by modifying the absorption of the radiation of the latter, at least at a determined wavelength, for example at 550 nm, detection, by comparison with a control test, of the quantity of hydrolyzed substrate.

The polypeptides according to the invention allow monoclonal or polyclonal antibodies to be prepared, which are characterized in that they specifically recognize the polypeptides according to the invention. It will advantageously be possible to prepare the monoclonal antibodies from hybridomas according to the technique described by Köhler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide that has served as an antigen has previously been immobilized. The polyclonal antibodies according to the invention can also be prepared by purification, on an affinity column on which a polypeptide according to the invention has previously been immobilized, of the antibodies contained in the serum of an animal immunologically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* in a sample, characterized in that it comprises the following steps: a) contacting of the sample with a mono- or polyclonal antibody according to the invention (under conditions allowing an immunological reaction between the antibodies and the polypeptides of *Alicyclobacillus acidocaldarius* possibly present in the biological sample); b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* in a sample, characterized in that it contains the following steps: a) if need be, isolation of the DNA from the sample to be analyzed; b) specific amplification of the DNA of the sample with the aid of at least one primer, or a pair of primers, according to the invention; c) demonstration of the amplification products.

These can be detected, for example, by the technique of molecular hybridization utilizing a nucleic probe according to the invention. This probe will advantageously be labeled with a nonradioactive (cold probe) or radioactive element.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in the biological sample.

A further embodiment of the invention comprises a method, characterized in that it comprises the following steps: a) contacting of a nucleotide probe according to the invention with a biological sample, the DNA contained in the biological sample having, if need be, previously been made accessible to hybridization under conditions allowing the hybridization of the probe with the DNA of the sample; b) demonstration of the hybrid formed between the nucleotide probe and the DNA of the biological sample.

The present invention also relates to a procedure according to the invention, characterized in that it comprises the following steps: a) contacting of a nucleotide probe immobilized on a support according to the invention with a biological sample, the DNA of the sample having, if need be, previously been made accessible to hybridization, under conditions allowing the hybridization of the probe with the DNA of the sample; b) contacting of the hybrid formed between the nucleotide probe immobilized on a support and the DNA contained in the biological sample, if need be after elimination of the DNA of the biological sample that has not hybridized with the probe, with a nucleotide probe labeled according to the invention; c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

Further embodiments of the invention comprise methods of at least partially degrading, cleaving, and/or removing a polysaccharide, lignocellulose, cellulose, hemicellulose, lignin, starch, chitin, polyhydroxybutyrate, heteroxylan, glycosides, xylan-, glucan-, galactan-, and/or mannan-decorating group. Degrading, cleaving, and/or removing these structures have in the art recognized utility such as those described in Mielenz 2001; Jeffries 1996; Shallom and Shoham 2003; Lynd et al. 2002; Vieille and Zeikus 2001; Bertoldo et al. 2004; and/or Malherbe and Cloete 2002.

Embodiments of methods include placing a recombinant, purified, and/or isolated polypeptide selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464; at least 99.6% sequence identity to SEQ ID NO:458; and at least 99.7% sequence identity to SEQ ID NO:456 in fluid contact with a polysaccharide, lignocellulose, cellulose, hemicellulose, lignin, starch, chitin, polyhydroxybutyrate, heteroxylans, glycoside, xylan-, glucan-, galactan-, and/or mannan-decorating group.

Further embodiments of methods include placing a cell producing or encoding a recombinant, purified, and/or isolated polypeptide selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464; at least 99.6% sequence identity to SEQ ID NO:458; and at least 99.7% sequence identity to SEQ ID NO:456 in fluid contact with a polysaccharide, lignocellulose, cellulose, hemicellulose, lignin, starch, chitin, polyhydroxybutyrate, heteroxylans, glycoside, xylan-, glucan-, galactan-, and/or mannan-decorating group.

As used herein, "partially degrading" relates to the rearrangement or cleavage of chemical bonds in the target structure.

In additional embodiments, methods of at least partially degrading, cleaving, and/or removing a polysaccharide, lignocellulose, cellulose, hemicellulose, lignin, starch, chitin, polyhydroxybutyrate, heteroxylan, glycosides, xylan-, glucan-, galactan-, and/or mannan-decorating group may take place at temperatures at or above about 25, 30, 35, 40, 45, 50, 55, 60, 65, 70, 75, 80, 85, 90, and/or 95 degrees Celsius and/or at a pH at, below, and/or above 7, 6, 5, 4, 3, 2, 1, and/or 0.

Further embodiments of the invention may comprise a kit for at least partially degrading, cleaving, and/or removing a polysaccharide, lignocellulose, cellulose, hemicellulose, lignin, starch, chitin, polyhydroxybutyrate, heteroxylan, glycosides, xylan-, glucan-, galactan-, and/or mannan-decorating group, the kit comprising a cell producing or encoding a recombinant, purified, and/or isolated a polypeptide selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464; at least 99.6% sequence identity to SEQ ID NO:458; and at least 99.7% sequence identity to SEQ ID NO:456 and/or a recombinant, purified, and/or isolated a polypeptide selected from the group consisting of a polypeptide having at least 90% sequence identity to SEQ ID NOs:2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID NO:462; at least 94% sequence identity to SEQ ID NO:36; at least 96% sequence identity to SEQ ID NO:460; at least 99% sequence identity to SEQ ID NO:464; at least 99.6% sequence identity to SEQ ID NO:458; and at least 99.7% sequence identity to SEQ ID NO:456.

The invention is described in additional detail in the following illustrative examples. Although the examples may represent only selected embodiments of the invention, it should be understood that the following examples are illustrative and not limiting.

In embodiments of the invention the any one of the isolated and/or purified polypeptides according to the invention may be enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5, 4, 3, 2, 1, and/or 0. In further embodiments of the invention, glycosylation, pegylation, and/or other post-translational modification may be required for the isolated and/or purified polypeptides according to the invention to be enzymatically active at a pH at or below 7, 6, 5, 4, 3, 2, 1, and/or 0 or at a temperature at or above about 25, 30, 35, 40, 45, 50, 55, 60, 65, 70, 75, 80, 85, 90, and/or 95 degrees Celsius.

EXAMPLES

Example 1

RAAC00169: an Esterase of the Alpha-Beta Hydrolase Superfamily

Provided in SEQ ID NO:1 is a nucleotide sequence isolated from *Alicyclobacillus acidocaldarius* and encoding the polypeptide of SEQ ID NO:2. As can be seen in FIGS. 1A and 1B, SEQ ID NO:2 aligns well with other proteins identified as esterases of the alpha-beta hydrolase superfamily. Of particular importance, it is noted that where amino acids are conserved in other esterases of the alpha-beta hydrolase superfamily, those amino acids are generally conserved in SEQ ID NO:2. Thus, the polypeptide provided in SEQ ID NO:2 is properly classified as an esterase of the alpha-beta hydrolase superfamily.

The polypeptides of SEQ ID NOs:13-17 are representative examples of conservative substitutions in the polypeptide of SEQ ID NO:2 and are encoded by nucleotide sequences of SEQ ID NOs:8-12, respectively.

The nucleotide sequences of SEQ ID NOs:1 and 8-12 are placed into expression vectors using techniques standard in the art. The vectors are then provided to cells such as bacteria cells or eukaryotic cells such as Sf9 cells or CHO (Chinese Hamster Ovary) cells. In conjunction with the normal machinery present in the cells, the vectors comprising SEQ ID NOs:1 and 8-12 produce the polypeptides of SEQ ID NOs:2 and 13-17. The polypeptides of SEQ ID NOs:2 and 13-17 are then isolated and/or purified. The isolated and/or purified polypeptides of SEQ ID NOs:2 and 13-17 are then demonstrated to have activity as esterases.

The isolated and/or purified polypeptides of SEQ ID NOs:2 and 13-17 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:2 and 13-17 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 2

RAAC00501: an Alpha-Beta Hydrolase

Provided in SEQ ID NO:18 is a nucleotide sequence isolated from *Alicyclobacillus acidocaldarius* and encoding the polypeptide of SEQ ID NO:19. As can be seen in FIGS. 2A and 2B, SEQ ID NO:19 aligns well with other proteins identified as alpha-beta hydrolases. Of particular importance, it is noted that where amino acids are conserved in other alpha-beta hydrolases, those amino acids are generally conserved in SEQ ID NO:19. Thus, the polypeptide provided in SEQ ID NO:19 is properly classified as an alpha-beta hydrolase.

The polypeptides of SEQ ID NOs:30-34 are representative examples of conservative substitutions in the polypeptide of SEQ ID NO:19 and are encoded by the nucleotide sequences of SEQ ID NOs:25-29, respectively.

The nucleotide sequences of SEQ ID NOs:18 and 25-29 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:18 and 25-29 produce the polypeptides of SEQ ID NOs:19 and 30-34. The polypeptides of SEQ ID NOs:19 and 30-34 are then isolated and/or purified. The isolated and/or purified polypeptides of SEQ ID NOs:19 and 30-34 are then demonstrated to have activity as alpha-beta hydrolases.

The isolated and/or purified polypeptides of SEQ ID NOs: 19 and 30-34 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:19 and 30-34 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 3

RAAC00568: an Alpha-Glucosidase

Provided in SEQ ID NO:35 is a nucleotide sequence isolated from *Alicyclobacillus acidocaldarius* and encoding the polypeptide of SEQ ID NO:36. As can be seen in FIGS. 3A, 3B, and 3C, SEQ ID NO:36 aligns well with other proteins identified as alpha-glucosidases. Of particular importance, it is noted that where amino acids are conserved in other alpha-glucosidases, those amino acids are generally conserved in SEQ ID NO:36. Thus, the polypeptide provided in SEQ ID NO:36 is properly classified as an alpha-glucosidase.

The polypeptides of SEQ ID NOs:46-50 are representative examples of conservative substitutions in the polypeptide of SEQ ID NO:36 and are encoded by nucleotide sequences of SEQ ID NOs:41-45, respectively.

The nucleotide sequences of SEQ ID NOs:35 and 41-45 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:35 and 41-45 produce the polypeptides of SEQ ID NOs:36 and 46-50. The polypeptides of SEQ ID NOs:36 and 46-50 are then isolated and/or purified. The isolated and/or purified polypeptides of SEQ ID NOs:36 and 46-50 are then demonstrated to have activity as alpha-glucosidases.

The isolated and/or purified polypeptides of SEQ ID NOs: 36 and 46-50 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:36 and 46-50 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 4

Production and Purification of RAAC00568: an Alpha-Glucosidase

The nucleotide sequence of SEQ ID NO:35 was cloned from *Alicyclobacillus acidocaldarius*. SEQ ID NO:35 encodes the polypeptide of SEQ ID NO:36. SEQ ID NO:35 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:36 was detected from both transformed *E. coli* and *P. pastoris* comprising SEQ ID NO:35 and RAAC00568 was affinity purified using a cobalt resin from these sources for activity testing.

Example 5

Alpha-Glucosidase Activity of RAAC00568

RAAC00568 purified from *P. pastoris* was tested for alpha-glucosidase activity using an assay summarized as follows:

A stock solution of α-glucopyranoside-p-nitrophenol (Sigma Cat. No. N1377) was prepared by adding 90.375 mg to 10 mL of water. This stock was diluted 1:15 in 50 mM sodium acetate buffer of pH 2.0, 3.5, and 5.5.

Samples of purified RAAC00568 generated in Example 4 were diluted 1:5, 1:10, 1:20, and 1:50 in 50 mM sodium acetate buffer of pH 2.0, 3.5, and 5.5. Samples (RAAC00568 samples and positive controls) were placed in the wells of a 96-well plate in 10 µL aliquots. Blanks of buffer only were placed in some wells. One hundred ninety µL of α-glucopyranoside-p-nitrophenol solution, preheated to 60 or 80 degrees Celsius, was then added to each well and the plate further incubated at 60 or 80 degrees Celsius for an additional 10 minutes. One hundred µL of 2.0 M sodium carbonate was then added to each well and the α-glucosidase activity was measured in a 96-well plate reader (Molecular Devices UV-Vis) at a wavelength of 405 nm.

Specific activity for RAAC00568 as determined appears in Table 1.

TABLE 1

| ASSAY<br>Alpha-glucosidase | SPECIFIC ACTIVITY<br>P. pastoris |
|---|---|
| pH 3.5, 60° C. | 2.5 μmol/min. mg |
| pH 5.5, 60° C. | 1.4 μmol/min. mg |
| pH 3.5, 80° C. | 2.8 μmol/min. mg |
| pH 2.0, 60° C. | 2.4 μmol/min. mg |

Example 6

Alpha-Xylosidase Activity of RAAC00568

RAAC00307 purified from P. pastoris was tested for xylosidase activity using a fluorescent assay summarized as follows:

A solution of α-xylopyranoside p-nitrophenol (Sigma Cat. No. N1895) was created by diluting 50 mg of α-xylopyranoside p-nitrophenol in 2 mL methanol. Individual aliquots of this solution were then diluted 1:50 with 50 mM sodium acetate buffer of pH 2.0, 3.5, and 5.5.

Samples of purified RAAC00568 generated in Example 5 were diluted 1:5, 1:10, 1:20, and 1:50 in 50 mM sodium acetate buffer of pH 2.0, 3.5, and 5.5. Samples (RAAC00568 samples and positive controls) were placed in the wells of a 96-well plate in 10 μL aliquots. Blanks of buffer only were placed in some wells. One hundred ninety μL of α-xylopyranoside solution, preheated to 60 or 80 degrees Celsius, was then added to each well and the plate further incubated at 60 or 80 degrees Celsius for an additional 10 minutes. One hundred μL of 2.0 M sodium carbonate was then added to each well and the α-xylosidase activity was measured in a 96-well plate reader (Molecular Devices UV-Vis) at a wavelength of 405 nm.

Specific activity for RAAC00568 as determined appears in Table 2.

TABLE 2

| ASSAY<br>Alpha-glucosidase | SPECIFIC ACTIVITY<br>P. pastoris |
|---|---|
| pH 3.5, 60° C. | 2.5 μmol/min. mg |
| pH 5.5, 60° C. | 6.2 μmol/min. mg |
| pH 3.5, 80° C. | 14 μmol/min. mg |
| pH 2.0, 60° C. | 1.36 μmol/min. mg |

Example 7

RAAC00594

Provided in SEQ ID NO:51 is a nucleotide sequence isolated from *Alicyclobacillus acidocaldarius* and encoding the polypeptide of SEQ ID NO:52. As can be seen in FIGS. 4A, 4B, and 4C, SEQ ID NO:52 aligns well with other proteins identified as alpha-xylosidases. Of particular importance, it is noted that where amino acids are conserved in other alpha-xylosidases, those amino acids are generally conserved in SEQ ID NO:52.

The polypeptides of SEQ ID NOs:63-67 are representative examples of conservative substitutions in the polypeptide of SEQ ID NO:52 and are encoded by nucleotide sequences of SEQ ID NOs:58-62, respectively.

The nucleotide sequences of SEQ ID NOs:51 and 58-62 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:51 and 58-62 produce the polypeptides of SEQ ID NOs:52 and 63-67. The polypeptides of SEQ ID NOs:52 and 63-67 are then isolated and/or purified.

Example 8

Production and Purification of RAAC00594

The nucleotide sequence of SEQ ID NO:51 was cloned from *Alicyclobacillus acidocaldarius*. SEQ ID NO:51 encodes the polypeptide of SEQ ID NO:52. SEQ ID NO:51 was cloned into the pBAD/HIS A expression vector for *E. coli* and provided to *E. coli* via electroporation into competent cells, respectively. Expression of SEQ ID NO:52 was detected from both transformed *E. coli* comprising SEQ ID NO:51 and RAAC00594 was affinity purified using a cobalt resin from these sources for activity testing.

Example 9

RAAC00602: an Alpha-L-Arabinofuranosidase

Provided in SEQ ID NO:68 is a nucleotide sequence isolated from *Alicyclobacillus acidocaldarius* and encoding the polypeptide of SEQ ID NO:69. As can be seen in FIGS. 5A and 5B, SEQ ID NO:69 aligns well with other proteins identified as alpha-L-arabinofuranosidases. Of particular importance, it is noted that where amino acids are conserved in other alpha-L-arabinofuranosidases, those amino acids are generally conserved in SEQ ID NO:69. Thus, the polypeptide provided in SEQ ID NO:69 is properly classified as an alpha-L-arabinofuranosidase.

The polypeptides of SEQ ID NOs:80-84 are representative examples of conservative substitutions in the polypeptide of SEQ ID NO:69 and are encoded by nucleotide sequences of SEQ ID NOs:75-79, respectively.

The nucleotide sequences of SEQ ID NOs:68 and 75-79 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:68 and 75-79 produce the polypeptides of SEQ ID NOs:69 and 80-84. The polypeptides of SEQ ID NOs:69 and 80-84 are then isolated and/or purified. The isolated and/or purified polypeptides of SEQ ID NOs:69 and 80-84 are then demonstrated to have activity as alpha-L-arabinofuranosidases.

The isolated and/or purified polypeptides of SEQ ID NOs:69 and 80-84 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:69 and 80-84 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 10

Production and Purification of RAAC00602: an Alpha-L-Arabinofuranosidase

The nucleotide sequence of SEQ ID NO:68 was cloned from *Alicyclobacillus acidocaldarius*. SEQ ID NO:68 encodes the polypeptide of SEQ ID NO:69. SEQ ID NO:68 was cloned into the pBAD/HIS A expression vector for *E. coli* and provided to *E. coli* via electroporation into competent cells, respectively. Expression of SEQ ID NO:69 was detected from both transformed *E. coli* comprising SEQ ID NO:68 and RAAC00602 was affinity purified using a cobalt resin from these sources for activity testing.

Example 11

Alpha-L-Arabinofuranosidase Activity of RAAC00602

RAAC00602 purified from *E. coli* and *P. pastoris* was tested for alpha-L-arabinofuranosidase activity using an assay summarized as follows:

A solution of α-arabinofuranoside p-nitrophenol (Sigma Cat. No. N3641) was created by diluting 271.2 mg of α-arabinofuranoside p-nitrophenol in 10 mL methanol. Individual aliquots of this solution were then diluted 1:50 with 50 mM sodium acetate buffer of pH 2.0 and 3.5.

Samples of purified RAAC00602 generated in Example 10 were diluted 1:5, 1:10, 1:20, and 1:50 in 50 mM sodium acetate buffer of pH 2.0 and 3.5. Samples (RAAC00602 samples and positive controls) were placed in the wells of a 96-well plate in 10 μL aliquots. Blanks of buffer only were placed in some wells. One hundred ninety μL of α-arabinofuranoside p-nitrophenol solution, preheated to 60 or 80 degrees Celsius, was then added to each well and the plate further incubated at 60 or 80 degrees Celsius for an additional 10 minutes. One hundred μL of 2.0 M sodium carbonate was then added to each well and the α-xylosidase activity measured in a 96-well plate reader (Molecular Devices UV-Vis) at a wavelength of 405 nm.

Specific activity for RAAC00692 as determined appears in Table 3.

TABLE 3

| ASSAY α-L-arabinofuranosidase | SPECIFIC ACTIVITY *P. pastoris* | SPECIFIC ACTIVITY *E. coli* |
|---|---|---|
| pH 3.5 60° C. | 5.54 μmol/min. mg | 15.2 μmol/min. mg |
| pH 2.0 60° C. | 0.1 μmol/min. mg | 0.07 μmol/min. mg |
| pH 3.5 80° C. | 3.53 μmol/min. mg | 9.77 μmol/min. mg |
| pH 2.0 80° C. | 1.46 μmol/min. mg | 0 μmol/min. mg |

Example 12

Beta-Xylosidase Activity of RAAC00602

RAAC00602 purified from *E. coli* and *P. pastoris* was tested for beta-xylosidase activity using a fluorescent assay summarized as follows:

A solution of MUXyl (4-methylumbelliferyl β-D-xylopyranoside) (Sigma M7008-1G CAS #6734-33-4) was created by diluting 10 mg (0.01 g) MUXyl in 1 mL dimethyl sulfoxide (DMSO). Individual aliquots of the DMSO solution were then diluted 1:100 with 50 mM sodium acetate buffer of pH 2.0 and 3.5.

Samples of purified RAAC00602 generated in Example 10 were diluted 1:5, 1:10, 1:20, and 1:50 in 50 mM sodium acetate buffer of pH 2.0 and 3.5. β-xylosidase from *A. niger* (Sigma X3501-5UN-CAS #9025-530) was diluted 1:100 in 50 mM sodium acetate buffer pH of 2.0 and 3.5 as positive controls. Samples (RAAC00602, samples and positive controls) were placed the wells of a 96-well plate in 50 μL aliquots. Blanks of buffer only were placed in some wells. The plate was then preheated to 60 or 80 degrees Celsius for 5 minutes. Ten μL of MUXyl solution was then added to each well and the plate further incubated at 60 or 80 degrees Celsius for an additional 10 minutes. One hundred μL of 0.5 M sodium carbonate was then added to each well and the β-xylosidase activity measured in a 96-well plate reader (SPECTRAMAX® GEmini) at an excitation of 355 nm and an emission of 460 nm. Specific activity for RAAC00602 as determined appears in Table 4.

TABLE 4

| ASSAY β-xylosidase | SPECIFIC ACTIVITY *P. pastoris* | SPECIFIC ACTIVITY *E. coli* |
|---|---|---|
| pH 3.5 60° C. | | 2.5 μmol/min. mg |
| pH 2.0 60° C. | 1.2 μmol/min. mg | |
| pH 2.0 80° C. | 0.7 μmol/min. mg | |

Example 13

RAAC00798: a Cell Wall-Associated Hydrolase

Provided in SEQ ID NO:85 is a nucleotide sequence isolated from *Alicyclobacillus acidocaldarius* and encoding the polypeptide of SEQ ID NO:86. As can be seen in FIGS. 6A and 6B, SEQ ID NO:86 aligns well with other proteins identified as cell wall-associated hydrolases. Of particular importance, it is noted that where amino acids are conserved in other cell wall-associated hydrolases, those amino acids are generally conserved in SEQ ID NO:86. Thus, the polypeptide provided in SEQ ID NO:86 is properly classified as a cell wall-associated hydrolase.

The polypeptides of SEQ ID NOs:96-100 are representative examples of conservative substitutions in the polypeptide of SEQ ID NO:86 and are encoded by nucleotide sequences of SEQ ID NOs:91-95, respectively.

The nucleotide sequences of SEQ ID NOs:85 and 91-95 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:85 and 91-95 produce the polypeptides of SEQ ID NOs:86 and 96-100. The polypeptides of SEQ ID NOs:86 and 96-100 are then isolated and/or purified. The isolated and/or purified polypeptides of SEQ ID NOs:86 and 96-100 are then demonstrated to have activity as cell wall-associated hydrolases.

The isolated and/or purified polypeptides of SEQ ID NOs: 86 and 96-100 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:86 and 96-100 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 14

RAAC01076: an Altronate Hydrolase

Provided in SEQ ID NO:101 is a nucleotide sequence isolated from *Alicyclobacillus acidocaldarius* and encoding the polypeptide of SEQ ID NO:102. As can be seen in FIGS. 7A and 7B, SEQ ID NO:102 aligns well with other proteins identified as altronate hydrolases. Of particular importance, it is noted that where amino acids are conserved in other altronate hydrolases, those amino acids are generally conserved in SEQ ID NO:102. Thus, the polypeptide provided in SEQ ID NO:102 is properly classified as an altronate hydrolase.

The polypeptides of SEQ ID NOs:113-117 are representative examples of conservative substitutions in the polypeptide of SEQ ID NO:102 and are encoded by nucleotide sequences of SEQ ID NOs:108-112, respectively.

The nucleotide sequences of SEQ ID NOs:101 and 108-112 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:101 and 108-112 produce the polypeptides of SEQ ID NOs:102 and 113-117. The polypeptides of SEQ ID NOs:102 and 113-117 are then isolated and/or purified. The isolated and/or purified polypeptides of SEQ ID NOs:102 and 113-117 are then demonstrated to have activity as altronate hydrolases.

The isolated and/or purified polypeptides of SEQ ID NOs: 102 and 113-117 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:102 and 113-117 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 15

RAAC04341

Provided in SEQ ID NO:118 is a nucleotide sequence isolated from *Alicyclobacillus acidocaldarius* and encoding the polypeptide of SEQ ID NO:119. As can be seen in FIGS. 8A and 8B, SEQ ID NO:119 aligns well with proteins identified as cellulase/endoglucanase Ms. Of particular importance, it is noted that where amino acids are conserved in other cellulase/endoglucanase Ms, those amino acids are generally conserved in SEQ ID NO:119.

The polypeptides of SEQ ID NOs:130-134 are representative examples of conservative substitutions in the polypeptide of SEQ ID NO:119 and are encoded by nucleotide sequences of SEQ ID NOs:125-129, respectively.

The nucleotide sequences of SEQ ID NOs:118 and 125-129 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:118 and 125-129 produce the polypeptides of SEQ ID NOs:119 and 130-134. The polypeptides of SEQ ID NOs:119 and 130-134 are then isolated and/or purified.

The isolated and/or purified polypeptides of SEQ ID NOs: 119 and 130-134 are challenged with peptides, polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 119 and 130-134 are demonstrated to have activity in at least partially degrading, cleaving, and/or removing peptides, polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 16

Production and Purification of RAAC04341

The nucleotide sequence of SEQ ID NO:118 was cloned from *Alicyclobacillus acidocaldarius*. SEQ ID NO:118 encodes the polypeptide of SEQ ID NO:119. SEQ ID NO:118 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:119 was detected from both transformed *E. coli* and *P. pastoris* comprising SEQ ID NO:118 and RAAC04341 was affinity purified using a cobalt resin from these sources for activity testing.

Example 17

RAAC04342

Provided in SEQ ID NO:135 is a nucleotide sequence isolated from *Alicyclobacillus acidocaldarius* and encoding the polypeptide of SEQ ID NO:136. As can be seen in FIGS. 9A and 9B, SEQ ID NO:136 aligns well with other proteins identified as cellulase/endoglucanase Ms. Of particular importance, it is noted that where amino acids are conserved in other cellulase/endoglucanase Ms, those amino acids are generally conserved in SEQ ID NO:136.

The polypeptides of SEQ ID NOs:147-151 are representative examples of conservative substitutions in the polypeptide of SEQ ID NO:136 and are encoded by the nucleotide sequences of SEQ ID NOs:142-146, respectively.

The nucleotide sequences of SEQ ID NOs:135 and 142-146 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:135 and 142-146 produce the polypeptides of SEQ ID NOs:136 and 147-151. The polypeptides of SEQ ID NOs:136 and 147-151 are then isolated and/or purified.

The isolated and/or purified polypeptides of SEQ ID NOs: 136 and 147-151 are challenged with peptides, polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 136 and 147-151 are demonstrated to have activity in at least partially degrading, cleaving, and/or removing peptides, polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 18

Production and Purification of RAAC04342

The nucleotide sequence of SEQ ID NO:135 was cloned from *Alicyclobacillus acidocaldarius*. SEQ ID NO:135 encodes the polypeptide of SEQ ID NO:136. SEQ ID NO:135 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:136 was detected from both transformed *E. coli* and *P. pastoris* comprising SEQ ID NO:135 and RAAC04342 was affinity purified using a cobalt resin from these sources for activity testing.

Example 19

RAAC04343: a Cellulase/Endoglucanase M

Provided in SEQ ID NO:152 is a nucleotide sequence isolated from *Alicyclobacillus acidocaldarius* and encoding the polypeptide of SEQ ID NO:153. As can be seen in FIGS. 10A and 10B, SEQ ID NO:153 aligns well with other proteins identified as cellulase/endoglucanase Ms. Of particular importance, it is noted that where amino acids are conserved in other cellulase/endoglucanase Ms, those amino acids are generally conserved in SEQ ID NO:153. Thus, the polypeptide provided in SEQ ID NO:153 is properly classified as a cellulose/endoglucanse M.

The polypeptides of SEQ ID NOs:162-166 are representative examples of conservative substitutions in the polypeptide of SEQ ID NO:153 and are encoded by the nucleotide sequences of SEQ ID NOs:157-161, respectively.

The nucleotide sequences of SEQ ID NOs:152 and 157-161 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:152 and 157-161 produce the polypeptides of SEQ ID NOs:153 and 162-166. The polypeptides of SEQ ID NOs:153 and 162-166 are then isolated and/or purified. The isolated and/or purified polypeptides of SEQ ID NOs:153 and 162-166 are then demonstrated to have activity as cellulase/endoglucanase Ms.

The isolated and/or purified polypeptides of SEQ ID NOs: 153 and 162-166 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:153 and 162-166 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 20

Production of RAAC04343

The nucleotide sequence of SEQ ID NO:152 was cloned from *Alicyclobacillus acidocaldarius*. SEQ ID NO:152 encodes the polypeptide of SEQ ID NO:153. SEQ ID NO:152 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:153 was detected from both transformed *E. coli* and *P. pastoris* comprising SEQ ID NO:152.

Example 21

RAAC01275: a Polygalacturonase

Provided in SEQ ID NO:167 is a nucleotide sequence isolated from *Alicyclobacillus acidocaldarius* and encoding the polypeptide of SEQ ID NO:168. As can be seen in FIGS. 11A-11C, SEQ ID NO:168 aligns well with other proteins identified as polygalacturonases. Of particular importance, it is noted that where amino acids are conserved in other polygalacturonases, those amino acids are generally conserved in SEQ ID NO:168. Thus, the polypeptide provided in SEQ ID NO:168 is properly classified as a polygalacturonase.

The polypeptides of SEQ ID NOs:179-183 are representative examples of conservative substitutions in the polypeptide of SEQ ID NO:168 and are encoded by the nucleotide sequences of SEQ ID NOs:174-178, respectively.

The nucleotide sequences of SEQ ID NOs:167 and 174-178 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:167 and 174-178 produce the polypeptides of SEQ ID NOs:168 and 179-183. The polypeptides of SEQ ID NOs:168 and 179-183 are then isolated and/or purified. The isolated and/or purified polypeptides of SEQ ID NOs:168 and 179-183 are then demonstrated to have activity as polygalacturonases.

The isolated and/or purified polypeptides of SEQ ID NOs: 168 and 179-183 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:168 and 179-183 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 22

RAAC01615: an Alpha-Galactosidase

Provided in SEQ ID NO:184 is a nucleotide sequence isolated from *Alicyclobacillus acidocaldarius* and encoding the polypeptide of SEQ ID NO:185. As can be seen in FIGS. 12A-12C, SEQ ID NO:185 aligns well with other proteins identified as alpha-galactosidase. Of particular importance, it is noted that where amino acids are conserved in other alpha-galactosidases, those amino acids are generally conserved in SEQ ID NO:185. Thus, the polypeptide provided in SEQ ID NO:185 is properly classified as an alpha-galactosidase.

The polypeptides of SEQ ID NOs:196-200 are representative examples of conservative substitutions in the polypeptide of SEQ ID NO:185 and are encoded by the nucleotide sequences of SEQ ED NOs:191-195, respectively.

The nucleotide sequences of SEQ ID NOs:184 and 191-195 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:184 and 191-195 produce the polypeptides of SEQ ID NOs:185 and 196-200. The polypeptides of SEQ ID NOs:185 and 196-200 are then isolated and/or purified. The isolated and/or purified polypeptides of SEQ ID NOs:185 and 196-200 are then demonstrated to have activity as alpha-galactosidases.

The isolated and/or purified polypeptides of SEQ ID NOs: 185 and 196-200 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:185 and 196-200 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 23

RAAC01621: a Cellobiose Phosphorylase

Provided in SEQ ID NO:201 is a nucleotide sequence isolated from *Alicyclobacillus acidocaldarius* and encoding the polypeptide of SEQ ID NO:202. As can be seen in FIGS. 13A-13K, SEQ ID NO:202 aligns well with other proteins identified as cellobiose phosphorylases. Of particular importance, it is noted that where amino acids are conserved in other cellobiose phosphorylases, those amino acids are generally conserved in SEQ ID NO:202. Thus, the polypeptide provided in SEQ ID NO:202 is properly classified as a cellobiose phosphorylase.

The polypeptides of SEQ ID NOs:213-217 are representative examples of conservative substitutions in the polypeptide of SEQ ID NO:202 and are encoded by the nucleotide sequences of SEQ ID NOs:208-212, respectively.

The nucleotide sequences of SEQ ID NOs:201 and 208-212 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:201 and 208-212 produce the polypeptides of SEQ ID NOs:202 and 213-217. The polypeptides of SEQ ID NOs:202 and 213-217 are then isolated and/or purified. The isolated and/or purified polypeptides of SEQ ID NOs:202 and 213-217 are then demonstrated to have activity as cellobiose phosphorylases.

The isolated and/or purified polypeptides of SEQ ID NOs: 202 and 213-217 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:202 and 213-217 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 24

RAAC01755: an Alpha-Glucosidase

Provided in SEQ ID NO:218 is a nucleotide sequence isolated from *Alicyclobacillus acidocaldarius* and encoding the polypeptide of SEQ ID NO:219. As can be seen in FIGS. 14A-14C, SEQ ID NO:219 aligns well with proteins identified as glycogen debranching enzymes. Of particular importance, it is noted that where amino acids are conserved in other glycogen debranching enzymes, those amino acids are generally conserved in SEQ ID NO:219.

The polypeptides of SEQ ID NOs:230-234 are representative examples of conservative substitutions in the polypeptide of SEQ ID NO:219 and are encoded by the nucleotide sequences of SEQ ID NOs:225-229, respectively.

The nucleotide sequences of SEQ ID NOs:218 and 225-229 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:218 and 225-229 produce the polypeptides of SEQ ID NOs:219 and 230-234. The polypeptides of SEQ ID NOs:219 and 230-234 are then isolated and/or purified. The isolated and/or purified polypeptides of SEQ ID NOs:219 and 230-234 are then demonstrated to have activity as alpha-glucosidases.

The isolated and/or purified polypeptides of SEQ ID NOs: 219 and 230-234 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:219 and 230-234 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 25

Production and Purification of RAAC01755

The nucleotide sequence of SEQ ID NO:218 was cloned from *Alicyclobacillus acidocaldarius*. SEQ ID NO:218 encodes the polypeptide of SEQ ID NO:219. SEQ ID NO:218 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:219 was detected from both transformed *E. coli* and *P. pastoris* comprising SEQ ID NO:218 and RAAC01755 was affinity purified using a cobalt resin from these sources for activity testing.

Example 26

RAAC01887: a Cellulase/Endoglucanase M

Provided in SEQ ID NO:235 is a nucleotide sequence isolated from *Alicyclobacillus acidocaldarius* and encoding the polypeptide of SEQ ID NO:236. As can be seen in FIGS. 15A and 15B, SEQ ID NO:236 aligns well with other proteins identified as cellulase/endoglucanase Ms. Of particular importance, it is noted that where amino acids are conserved in other cellulase/endoglucanase Ms, those amino acids are generally conserved in SEQ ID NO:236. Thus, the polypeptide provided in SEQ ID NO:236 is properly classified as a cellulase/endoglucanase M.

The polypeptides of SEQ ID NOs:247-251 are representative examples of conservative substitutions in the polypeptide of SEQ ID NO:236 and are encoded by the nucleotide sequences of SEQ ID NOs:242-246, respectively.

The nucleotide sequences of SEQ ID NOs:235 and 242-246 are placed into expression vectors using techniques standard in the art. The vectors are then provided to cells such as bacteria cells or eukaryotic cells such as S19 cells or CHO cells. In conjunction with the normal machinery present in the cells, the vectors comprising SEQ ID NOs:235 and 242-246 produce the polypeptides of SEQ ID NOs:236 and 247-251. The polypeptides of SEQ ID NOs:236 and 247-251 are then isolated and/or purified. The isolated and/or purified polypeptides of SEQ ID NOs:236 and 247-251 are then demonstrated to have activity as cellulase/endoglucanase Ms.

The isolated and/or purified polypeptides of SEQ ID NOs:236 and 247-251 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:236 and 247-251 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 27

Production of RAAC01887

The nucleotide sequence of SEQ ID NO:235 was cloned from *Alicyclobacillus acidocaldarius*. SEQ ID NO:235 encodes the polypeptide of SEQ ID NO:236. SEQ ID NO:235 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:236 was detected from both transformed *E. coli* and *P. pastoris* comprising SEQ ID NO:235.

Example 28

RAAC01897: an Acetyl Esterase/Acetyl Hydrolase

Provided in SEQ ID NO:252 is a nucleotide sequence isolated from *Alicyclobacillus acidocaldarius* and encoding the polypeptide of SEQ ID NO:253. As can be seen in FIGS. 16A and 16B, SEQ ID NO:253 aligns well with other proteins identified as acetyl esterase/acetyl hydrolases. Of particular importance, it is noted that where amino acids are conserved in other acetyl esterase/acetyl hydrolases, those amino acids are generally conserved in SEQ ID NO:253. Thus, the polypeptide provided in SEQ ID NO:253 is properly classified as an acetyl esterase/acetyl hydrolase.

The polypeptides of SEQ ID NOs:264-268 are representative examples of conservative substitutions in the polypeptide of SEQ ID NO:253 and are encoded by the nucleotide sequences of SEQ ID NOs:259-263, respectively.

The nucleotide sequences of SEQ ID NOs:252 and 259-263 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:252 and 259-263 produce the polypeptides of SEQ ID NOs:253 and 264-268. The polypeptides of SEQ ID NOs:253 and 264-268 are then isolated and/or purified. The isolated and/or purified polypeptides of SEQ ID NOs:253 and 264-268 are then demonstrated to have activity as acetyl esterase/acetyl hydrolases.

The isolated and/or purified polypeptides of SEQ ID NOs:253 and 264-268 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:253 and 264-268 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 29

RAAC01917: a beta-1,4-xylanase

Provided in SEQ ID NO:269 is a nucleotide sequence isolated from *Alicyclobacillus acidocaldarius* and encoding the polypeptide of SEQ ID NO:270. As can be seen in FIGS. 17A and 17B, SEQ ID NO:270 aligns well with other proteins identified as beta-1,4-xylanases. Of particular importance, it is noted that where amino acids are conserved in other beta-1,4-xylanases, those amino acids are generally conserved in SEQ ID NO:270. Thus, the polypeptide provided in SEQ ID NO:270 is properly classified as a beta-1,4-xylanase.

The polypeptides of SEQ ID NOs:281-285 are representative examples of conservative substitutions in the polypeptide of SEQ ID NO:270 and are encoded by the nucleotide sequences of SEQ ID NOs:276-280, respectively.

The nucleotide sequences of SEQ ID NOs:269 and 276-280 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:269 and 276-280 produce the polypeptides of SEQ ID NOs:270 and 281-285. The polypeptides of SEQ ID NOs:270 and 281-285 are then isolated and/or purified. The isolated and/or purified polypeptides of SEQ ID NOs:270 and 281-285 are then demonstrated to have activity as beta-1,4-xylanases.

The isolated and/or purified polypeptides of SEQ ID NOs:270 and 281-285 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:270 and 281-285 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 30

Production of RAAC01917

The nucleotide sequence of SEQ ID NO:269 was cloned from *Alicyclobacillus acidocaldarius*. SEQ ID NO:269 encodes the polypeptide of SEQ ID NO:270. SEQ ID NO:269 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:270 was detected from both transformed *E. coli* and *P. pastoris* comprising SEQ ID NO:269.

Example 31

RAAC02404: a Cinnamoyl Ester Hydrolase

Provided in SEQ ID NO:286 is a nucleotide sequence isolated from *Alicyclobacillus acidocaldarius* and encoding the polypeptide of SEQ ID NO:287. As can be seen in FIGS. 18A and 18B, SEQ ID NO:287 aligns well with other proteins identified as cinnamoyl ester hydrolases. Of particular importance, it is noted that where amino acids are conserved in other cinnamoyl ester hydrolases, those amino acids are generally conserved in SEQ ID NO:287. Thus, the polypeptide provided in SEQ ID NO:287 is properly classified as a cinnamoyl ester hydrolase.

The polypeptides of SEQ ID NOs:298-302 are representative examples of conservative substitutions in the polypeptide of SEQ ID NO:287 and are encoded by the nucleotide sequences of SEQ ID NOs:293-297, respectively.

The nucleotide sequences of SEQ ID NOs:286 and 293-297 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:286 and 293-297 produce the polypeptides of SEQ ID NOs:287 and 298-302. The polypeptides of SEQ ID NOs:287 and 298-302 are then isolated and/or purified. The isolated and/or purified polypeptides of SEQ ID NOs:287 and 298-302 are then demonstrated to have activity as cinnamoyl ester hydrolases.

The isolated and/or purified polypeptides of SEQ ID NOs: 287 and 298-302 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:287 and 298-302 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 32

RAAC02424: a Carboxylesterase Type B

Provided in SEQ ID NO:303 is a nucleotide sequence isolated from *Alicyclobacillus acidocaldarius* and encoding the polypeptide of SEQ ID NO:304. As can be seen in FIGS. 19A and 19B, SEQ ID NO:304 aligns well with other proteins identified as carboxylesterase type Bs. Of particular importance, it is noted that where amino acids are conserved in other carboxylesterase type Bs, those amino acids are generally conserved in SEQ ID NO:304. Thus, the polypeptide provided in SEQ ID NO:304 is properly classified as a carboxylesterase type B.

The polypeptides of SEQ ID NOs:315-319 are representative examples of conservative substitutions in the polypeptide of SEQ ID NO:304 and are encoded by the nucleotide sequences of SEQ ID NOs:310-314, respectively.

The nucleotide sequences of SEQ ID NOs:303 and 310-314 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:303 and 310-314 produce the polypeptides of SEQ ID NOs:304 and 315-319. The polypeptides of SEQ ID NOs:304 and 315-319 are then isolated and/or purified. The isolated and/or purified polypeptides of SEQ ID NOs:304 and 315-319 are then demonstrated to have activity as carboxylesterase type Bs.

The isolated and/or purified polypeptides of SEQ ID NOs: 304 and 315-319 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:304 and 315-319 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 33

Production and Purification of RAAC02424

The nucleotide sequence of SEQ ID NO:303 was cloned from *Alicyclobacillus acidocaldarius*. SEQ ID NO:303 encodes the polypeptide of SEQ ID NO:304. SEQ ID NO:303 was cloned into the pBAD/HIS A expression vector for *E. coli* and provided to *E. coli* via electroporation into competent cells, respectively. Expression of SEQ ID NO:304 was detected from both transformed *E. coli* comprising SEQ ID NO:303 and RAAC02424 was affinity purified using a cobalt resin from these sources for activity testing.

Example 34

RAAC02616: a Beta Galactosidase/Beta-Glucuronidase

Provided in SEQ ID NO:320 is a nucleotide sequence isolated from *Alicyclobacillus acidocaldarius* and encoding the polypeptide of SEQ ID NO:321. As can be seen in FIGS. 20A-20D, SEQ ID NO:321 aligns well with other proteins identified as beta galactosidase/beta-glucuronidases. Of particular importance, it is noted that where amino acids are conserved in other beta galactosidase/beta-glucuronidases, those amino acids are generally conserved in SEQ ID NO:321. Thus, the polypeptide provided in SEQ ID NO:321 is properly classified as a beta galactosidase/beta-glucuronidase.

The polypeptides of SEQ ID NOs:331-335 are representative examples of conservative substitutions in the polypeptide of SEQ ID NO:321 and are encoded by the nucleotide sequences of SEQ ID NOs:326-330, respectively.

The nucleotide sequences of SEQ ID NOs:320 and 326-330 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:320 and 326-330 produce the polypeptides of SEQ ID NOs:321 and 331-335. The polypeptides of SEQ ID NOs:321 and 331-335 are then isolated and/or purified. The isolated and/or purified polypeptides of SEQ ID NOs:321 and 331-335 are then demonstrated to have activity as beta galactosidase/beta-glucuronidases.

The isolated and/or purified polypeptides of SEQ ID NOs: 321 and 331-335 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:321 and 331-335 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 35

RAAC02661: a Xylan Alpha-1,2-Glucuronidase

Provided in SEQ ID NO:336 is a nucleotide sequence isolated from *Alicyclobacillus acidocaldarius* and encoding the polypeptide of SEQ ID NO:337. As can be seen in FIGS. 21A-21D, SEQ ID NO:337 aligns well with other proteins identified as xylan alpha-1,2-glucuronidases. Of particular importance, it is noted that where amino acids are conserved in other xylan alpha-1,2-glucuronidases, those amino acids are generally conserved in SEQ ID NO:337. Thus, the polypeptide provided in SEQ ID NO:337 is properly classified as a xylan alpha-1,2-glucuronidase.

The polypeptides of SEQ ID NOs:348-352 are representative examples of conservative substitutions in the polypeptide of SEQ ID NO:337 and are encoded by the nucleotide sequences of SEQ ID NOs:343-347, respectively.

The nucleotide sequences of SEQ ID NOs:336 and 343-347 are placed into expression vectors using techniques standard in the art. The vectors are then provided to cells such as bacteria cells or eukaryotic cells such as SN cells or CHO cells. In conjunction with the normal machinery present in the cells, the vectors comprising SEQ ID NOs:336 and 343-347 produce the polypeptides of SEQ ID NOs:337 and 348-352. The polypeptides of SEQ ID NOs:337 and 348-352 are then isolated and/or purified. The isolated and/or purified polypeptides of SEQ ID NOs:337 and 348-352 are then demonstrated to have activity as xylan alpha-1,2-glucuronidases.

The isolated and/or purified polypeptides of SEQ ID NOs: 337 and 348-352 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:337 and 348-352 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 36

RAAC02925: a 3-Hydroxyisobutyryl-CoA Hydrolase

Provided in SEQ ID NO:353 is a nucleotide sequence isolated from *Alicyclobacillus acidocaldarius* and encoding the polypeptide of SEQ ID NO:354. As can be seen in FIGS. 22A-22C, SEQ ID NO:354 aligns well with other proteins identified as 3-hydroxyisobutyryl-CoA hydrolases. Of particular importance, it is noted that where amino acids are conserved in other 3-hydroxyisobutyryl-CoA hydrolases, those amino acids are generally conserved in SEQ ID NO:354. Thus, the polypeptide provided in SEQ ID NO:354 is properly classified as a 3-hydroxyisobutyryl-CoA hydrolase.

The polypeptides of SEQ ID NOs:365-369 are representative examples of conservative substitutions in the polypeptide of SEQ ID NO:354 and are encoded by the nucleotide sequences of SEQ ID NOs:360-364, respectively.

The nucleotide sequences of SEQ ID NOs:353 and 360-364 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:353 and 360-364 produce the polypeptides of SEQ ID NOs:354 and 365-369. The polypeptides of SEQ ID NOs:354 and 365-369 are then isolated and/or purified. The isolated and/or purified polypeptides of SEQ ID NOs:354 and 365-369 are then demonstrated to have activity as 3-hydroxyisobutyryl-CoA hydrolases.

The isolated and/or purified polypeptides of SEQ ID NOs: 354 and 365-369 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:354 and 365-369 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 37

RAAC03001: a Beta-Glucosidase

Provided in SEQ ID NO:370 is a nucleotide sequence isolated from *Alicyclobacillus acidocaldarius* and encoding the polypeptide of SEQ ID NO:371. As can be seen in FIGS. 23A-23D, SEQ ID NO:371 aligns well with other proteins identified as beta-glucosidases. Of particular importance, it is noted that where amino acids are conserved in other beta-glucosidases, those amino acids are generally conserved in SEQ ID NO:371. Thus, the polypeptide provided in SEQ ID NO:371 is properly classified as a beta-glucosidase.

The polypeptides of SEQ ID NOs:382-386 are representative examples of conservative substitutions in the polypeptide of SEQ ID NO:371 and are encoded by nucleotide sequences of SEQ ID NOs:377-381, respectively.

The nucleotide sequences of SEQ ID NOs:370 and 377-381 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:370 and 377-381 produce the polypeptides of SEQ ID NOs:371 and 382-386. The polypeptides of SEQ ID NOs:371 and 382-386 are then isolated and/or purified. The isolated and/or purified polypeptides of SEQ ID NOs:371 and 382-386 are then demonstrated to have activity as beta-glucosidases.

The isolated and/or purified polypeptides of SEQ ID NOs: 371 and 382-386 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:371 and 382-386 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 38

Production and Purification of RAAC03001: a Beta-Glucosidase

The nucleotide sequence of SEQ ID NO:370 was cloned from *Alicyclobacillus acidocaldarius*. SEQ ID NO:370 encodes the polypeptide of SEQ ID NO:371. SEQ ID NO:370 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:370 was detected from both transformed *E. coli* and *P. pastoris* comprising SEQ ID NO:370 and RAAC03001 was affinity purified using a cobalt resin from these sources for activity testing.

Example 39

Beta-Glucosidase Activity of RAAC03001

RAAC03001 purified from both *E. coli* and *P. pastoris* was tested for beta-glucosidase activity using the assay summarized as follows: A solution of β-glucopyranoside p-nitrophenol (Sigma Cat. No. N7006) was created by diluting 301.25 mg of β-glucopyranoside p-nitrophenol in 20 mL water. Individual aliquots of this solution were then diluted 1:25 with 50 mM sodium acetate buffer of pH 2.0, 3.5, and 5.5.

Samples of purified RAAC03001 generated in Example 39 were diluted 1:5, 1:10, 1:20, and 1:50 in 50 mM sodium acetate buffer of pH 2.0, 3.5, and 5.5. Samples (RAAC03001, samples and positive controls) were placed in the wells of a 96-well plate in 10 µL aliquots. Blanks of buffer only were placed in some wells. One hundred ninety µL of β-glucopyranoside p-nitrophenol solution, preheated to 60 or 80 degrees Celsius, was then added to each well and the plate further incubated at 60 or 80 degrees Celsius for an additional 10 minutes. One hundred pt of 2.0 M sodium carbonate was then added to each well and the α-xylosidase activity was measured in a 96-well plate reader (Molecular Devices UV-Vis) at a wavelength of 405 nm.

The above assay demonstrated that the RAAC03001 protein isolated from *E. coli* had beta-glucosidase activity at pHs of 3.5 and 5.5 and a temperature of 60 degrees Celsius; and the RAAC03001 protein isolated from *P. pastoris* had beta-glucosidase activity at a pH of 5.5 and at a temperature of 60 degrees Celsius.

Example 40

RAAC02913: a Chitooligosaccharide Deacetylase

Provided in SEQ ID NO:387 is a nucleotide sequence isolated from *Alicyclobacillus acidocaldarius* and encoding the polypeptide of SEQ ID NO:388. As can be seen in FIGS. 24A and 24B, SEQ ID NO:388 aligns well with other proteins identified as chitooligosaccharide deacetylases. Of particular importance, it is noted that where amino acids are conserved in other chitooligosaccharide deacetylases, those amino acids are generally conserved in SEQ ID NO:388. Thus, the polypeptide provided in SEQ ID NO:388 is properly classified as a chitooligosaccharide deacetylase.

The polypeptides of SEQ ID NOs:399-403 are representative examples of conservative substitutions in the polypeptide of SEQ ID NO:388 and are encoded by the nucleotide sequences of SEQ ID NOs:394-398, respectively.

The nucleotide sequences of SEQ ID NOs:387 and 394-398 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:387 and 394-398 produce the polypeptides of SEQ ID NOs:388 and 399-403. The polypeptides of SEQ ID NOs:388 and 399-403 are then isolated and/or purified. The isolated and/or purified polypeptides of SEQ ID NOs:388 and 399-403 are then demonstrated to have activity as chitooligosaccharide deacetylases.

The isolated and/or purified polypeptides of SEQ ID NOs: 388 and 399-403 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:388 and 399-403 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 41

RAAC02839: a Chitooligosaccharide Deacetylase

Provided in SEQ ID NO:404 is a nucleotide sequence isolated from *Alicyclobacillus acidocaldarius* and encoding the polypeptide of SEQ ID NO:405. As can be seen in FIGS. 25A and 25B, SEQ ID NO:405 aligns well with other proteins identified as chitooligosaccharide deacetylases. Of particular importance, it is noted that where amino acids are conserved in other chitooligosaccharide deacetylases, those amino acids are generally conserved in SEQ ID NO:405. Thus, the polypeptide provided in SEQ ID NO:405 is properly classified as a chitooligosaccharide deacetylase.

The polypeptides of SEQ ID NOs:416-420 are representative examples of conservative substitutions in the polypeptide of SEQ ID NO:405 and are encoded by the nucleotide sequences of SEQ ID NOs:411-415, respectively.

The nucleotide sequences of SEQ ID NOs:404 and 411-415 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:404 and 411-415 produce the polypeptides of SEQ ID NOs:405 and 416-420. The polypeptides of SEQ ID NOs:405 and 416-420 are then isolated and/or purified. The isolated and/or purified polypeptides of SEQ ID NOs:405 and 416-420 are then demonstrated to have activity as chitooligosaccharide deacetylases.

The isolated and/or purified polypeptides of SEQ ID NOs: 405 and 416-420 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:405 and 416-420 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 42

RAAC00961: a Chitooligosaccharide Deacetylase

Provided in SEQ ID NO:421 is a nucleotide sequence isolated from *Alicyclobacillus acidocaldarius* and encoding the polypeptide of SEQ ID NO:422. As can be seen in FIGS. 26A-26C, SEQ ID NO:422 aligns well with other proteins identified as chitooligosaccharide deacetylases. Of particular importance, it is noted that where amino acids are conserved in other chitooligosaccharide deacetylases, those amino acids are generally conserved in SEQ ID NO:422. Thus, the polypeptide provided in SEQ ID NO:422 is properly classified as a chitooligosaccharide deacetylase.

The polypeptides of SEQ ID NOs:433-437 are representative examples of conservative substitutions in the polypeptide of SEQ ID NO:422 and are encoded by the nucleotide sequences of SEQ ID NOs:428-432, respectively.

The nucleotide sequences of SEQ ID NOs:421 and 428-432 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:421 and 428-432 produce the polypeptides of SEQ ID NOs:422 and 433-437. The polypeptides of SEQ ID NOs:422 and 433-437 are then isolated and/or purified. The isolated and/or purified polypeptides of SEQ ID NOs:422 and 433-437 are then demonstrated to have activity as chitooligosaccharide deacetylases.

The isolated and/or purified polypeptides of SEQ ID NOs:422 and 433-437 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:422 and 433-437 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 43

RAAC00361: a Chitooligosaccharide Deacetylase

Provided in SEQ ID NO:438 is a nucleotide sequence isolated from *Alicyclobacillus acidocaldarius* and encoding the polypeptide of SEQ ID NO:439. As can be seen in FIGS. 27A and 27B, SEQ ID NO:439 aligns well with other proteins identified as chitooligosaccharide deacetylases. Of particular importance, it is noted that where amino acids are conserved in other chitooligosaccharide deacetylases, those amino acids are generally conserved in SEQ ID NO:439. Thus, the polypeptide provided in SEQ ID NO:439 is properly classified as a chitooligosaccharide deacetylase.

The polypeptides of SEQ ID NOs:450-454 are representative examples of conservative substitutions in the polypeptide of SEQ ID NO:439 and are encoded by the nucleotide sequences of SEQ ID NOs:445-449, respectively.

The nucleotide sequences of SEQ ID NOs:438 and 445-449 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:438 and 445-449 produce the polypeptides of SEQ ID NOs:439 and 450-454. The polypeptides of SEQ ID NOs:439 and 450-454 are then isolated and/or purified. The isolated and/or purified polypeptides of SEQ ID NOs:439 and 450-454 are then demonstrated to have activity as chitooligosaccharide deacetylases.

The isolated and/or purified polypeptides of SEQ ID NOs:439 and 450-454 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:439 and 450-454 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 44

RAAC00569: a Glucan 1,4-Alpha-Maltohydrolase

Provided in SEQ ID NO:455 is a nucleotide sequence isolated from *Alicyclobacillus acidocaldarius* and encoding the polypeptide of SEQ ID NO:456. SEQ ID NO:456 aligns at about 99% identity with gi|6686566, a glucan 1,4-alpha-maltohydrolase. Thus, the polypeptide provided in SEQ ID NO:456 is properly classified as a glucan 1,4-alpha-maltohydrolase.

The nucleotide sequence of SEQ ID NO:455 is placed into an expression vector using techniques standard in the art. The vector is then provided to cells such as bacteria cells or eukaryotic cells such as Sf9 cells or CHO cells. In conjunction with the normal machinery present in the cells, the vector comprising SEQ ID NO:455 produces the polypeptide of SEQ ID NO:456. The polypeptide of SEQ ID NO:456 is then isolated and/or purified. The isolated and/or purified polypeptide of SEQ ID NO:456 is then demonstrated to have activity as glucan 1,4-alpha-maltohydrolase.

The isolated and/or purified polypeptide of SEQ ID NO:456 is then challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NO:456 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 45

RAAC00574: a Glycosidase

Provided in SEQ ID NO:457 is a nucleotide sequence isolated from *Alicyclobacillus acidocaldarius* and encoding the polypeptide of SEQ ID NO:458. SEQ ID NO:458 aligns at about 99% identity with gi|39301, a glycosidase. Thus, the polypeptide provided in SEQ ID NO:458 is properly classified as a glycosidase.

The nucleotide sequence of SEQ ID NO:457 is placed into an expression vector using techniques standard in the art. The vector is then provided to cells such as bacteria cells or eukaryotic cells such as Sf9 cells or CHO cells. In conjunction with the normal machinery present in the cells, the vector comprising SEQ ID NO:457 produces the polypeptide of SEQ ID NO:458. The polypeptide of SEQ ID NO:458 is then isolated and/or purified. The isolated and/or purified polypeptide of SEQ ID NO:458 is then demonstrated to have activity as a glycosidase.

The isolated and/or purified polypeptide of SEQ ID NO:458 is then challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptide of SEQ ID NO:458 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 46

RAAC00575: an Acetyl Esterase

Provided in SEQ ID NO:459 is a nucleotide sequence isolated from *Alicyclobacillus acidocaldarius* and encoding the polypeptide of SEQ ID NO:460. SEQ ID NO:460 aligns at about 95% identity with gi|151567607, an acetyl esterase. Thus, the polypeptide provided in SEQ ID NO:460 is properly classified as an acetyl esterase.

The nucleotide sequence of SEQ ID NO:459 is placed into an expression vector using techniques standard in the art. The vector is then provided to cells such as bacteria cells or eukaryotic cells such as Sf9 cells or CHO cells. In conjunction with the normal machinery present in the cells, the vector comprising SEQ ID NO:459 produces the polypeptide of SEQ ID NO:460.

The polypeptide of SEQ ID NO:460 is then isolated and/or purified. The isolated and/or purified polypeptide of SEQ ID NO:460 is then demonstrated to have activity as an acetyl esterase.

The isolated and/or purified polypeptide of SEQ ID NO:460 is then challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptide of SEQ ID NO:460 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 47

RAAC01618: an endo-beta-1,4-mannanase

Provided in SEQ ID NO:461 is a nucleotide sequence isolated from *Alicyclobacillus acidocaldarius* and encoding the polypeptide of SEQ ID NO:462. SEQ ID NO:462 aligns at about 92% identity with gi|110611196, an endo-beta-1,4-mannanase. Thus, the polypeptide provided in SEQ ID NO:462 is properly classified as an endo-beta-1,4-mannanase.

The nucleotide sequence of SEQ ID NO:461 is placed into an expression vector using techniques standard in the art. The vector is then provided to cells such as bacteria cells or eukaryotic cells such as Sf9 cells or CHO cells. In conjunction with the normal machinery present in the cells, the vector comprising SEQ ID NO:461 produces the polypeptide of SEQ ID NO:462. The polypeptide of SEQ ID NO:462 is then isolated and/or purified. The isolated and/or purified polypeptide of SEQ ID NO:462 is then demonstrated to have activity as an endo-beta-1,4-mannanase.

The isolated and/or purified polypeptide of SEQ ID NO:462 is then challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NO:462 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 48

RAAC01994: a Beta-Glucosidase

Provided in SEQ ID NO:463 is a nucleotide sequence isolated from *Alicyclobacillus acidocaldarius* and encoding the polypeptide of SEQ ID NO:464. SEQ ID NO:464 aligns at about 92% identity with gi|110611196, a beta-glucosidase. Thus, the polypeptide provided in SEQ ID NO:464 is properly classified as a beta-glucosidase.

The nucleotide sequence of SEQ ID NO:463 is placed into an expression vector using techniques standard in the art. The vector is then provided to cells such as bacteria cells or eukaryotic cells such as Sf9 cells or CHO cells. In conjunction with the normal machinery present in the cells, the vector comprising SEQ ID NO:463 produces the polypeptide of SEQ ID NO:464. The polypeptide of SEQ ID NO:464 is then isolated and/or purified. The isolated and/or purified polypeptide of SEQ ID NO:464 is then demonstrated to have activity as a beta-glucosidase.

The isolated and/or purified polypeptide of SEQ ID NO:464 is then challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptide of SEQ ID NO:464 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their legal equivalents.

BIBLIOGRAPHIC REFERENCES

1. Barany F., 1991, *PNAS, USA* 88:189-193.
2. Bertoldo et al., 2004, *Eng. Life Sci.* 4, No. 6.
3. Buckholz R. G., 1993, Yeast Systems for the Expression of Heterologous Gene Products, *Curr. Op. Biotechnology* 4:538-542.
4. Burg J. L. et al., 1996, *Mol. and Cell. Probes* 10:257-271.
5. Chu B. C. F. et al., 1986, *NAR* 14:5591-5603.
6. Duck P. et al., 1990, *Biotechniques* 9:142-147.
7. Edwards C. P. and A. Aruffo, 1993, Current Applications of COS Cell-Based Transient Expression Systems, *Curr. Op. Biotechnology* 4:558-563.
8. Garrote G., H. Dominguez, and J. C. Parajo, 2001, Manufacture of Xylose-Based Fermentation Media from Corncobs by Posthydrolysis of Autohydrolysis Liquors, *Appl. Biochem. Biotechnol.*, 95:195-207.
9. Guateli J. C. et al., 1990, *PNAS, USA*, 87:1874-1878.
10. Hamelinck C. N., G. van Hooijdonk, and A. P. C. Faaij, 2005, Ethanol from Lignocellulosic Biomass: Techno- Economic Performance in Short-, Middle-, and Long-Term, *Biomass Bioenergy* 28:384-410.
11. Houben-Weyl, 1974, *Methoden der Organischen Chemie*, E. Wunsch, ed., Vols. 15-I and 15-II, Thieme, Stuttgart.
12. Huygen K. et al., 1996, *Nature Medicine* 2(8):893-898.
13. Innis M. A. et al., 1990, in *PCR Protocols, A Guide to Methods and Applications*, San Diego, Academic Press.
14. Jeffries, 1996, *Curr. Op. in Biotech.* 7:337-342.
15. Kievits T. et al., 1991, *J. Virol. Methods*, 35:273-286.
16. Köhler G. et al., 1975, *Nature*, 256(5517):495497.
17. Kwoh D. Y. et al., 1989, *PNAS*, zuDS 86:1173-1177.
18. Liu C. and C. E. Wyman, 2003, The Effect of Flow Rate of Compressed Hot Water on Xylan, Lignin, and Total Mass Removal from Corn Stover, *Ind. Eng. Chem. Res.*, 42:5409-5416.
19. Luckow V. A., 1993, *Baculovirus* Systems for the Expression of Human Gene Products, *Curr. Op. Biotechnology* 4:564-572.
20. Lynd et al., 2002, *Micro. and Mol. Biol. Rev.*, vol. 66, No. 3, pp. 506-577.
21. Malherbe and Cloete, 2002, *Reviews in Environmental Science and Biotechnology* 1:105-114.
22. Matthews J. A. et al., 1988, *Analy. Biochem.* 169:1-25.
23. Merrifield R. D., 1966, *J. Am. Chem. Soc.* 88(21):5051-5052.
24. Miele E. A. et al., 1983, *J. Mol. Biol.* 171:281-295.
25. Mielenz, 2001, *Curr. Op. in Micro.* 4:324-329.
26. Olins P. O. and S. C. Lee, 1993, Recent Advances in Heterologous Gene Expression in *E. coli*, *Curr. Op. Biotechnology* 4:520-525.
27. Rolfs A. et al., 1991, in *PCR Topics*, Usage of Polymerase Chain Reaction in Genetic and Infectious Disease, Berlin: Springer-Verlag.
28. Sambrook J. et al., 1989, *Molecular Cloning: A Laboratory Manual*, Cold Spring Harbor, N.Y.: Cold Spring Harbor Laboratory Press.
29. Sanchez-Pescador R., 1988, *J. Clin. Microbiol.* 26(10): 1934-1938.
30. Segev D., 1992, *"Non-radioactive Labeling and Detection of Biomolecules,"* C. Kessler, ed., Springer-Verlag, Berlin, N.Y., pp. 197-205.
31. Shallom and Shoham, 2003, *Curr. Op. in Micro.* 6:219-228.
32. Tsao G. T., M. R. Ladisch, and H. R. Bungay, 1987, Biomass Refining, in *Advanced Biochemical Engineering*, Wiley Interscience, N.Y., 79-101.
33. Urdea M. S., 1988, *Nucleic Acids Research* II:4937-4957.
34. Vieille and Zeikus, 2001, *Micro. and Mol. Biol. Rev.*, vol. 65, No. 1, pp. 1-43.
35. Walker G. T. et al., 1992, *NAR* 20:1691-1696.
36. Walker G. T. et al., 1992, *PNAS*, USA 89:392-396.
37. White B. A. et al., 1997, *Methods in Molecular Biology*, 67, Humana Press, Totowa, N.J.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08202716B2). An electronic copy of the "Sequence Listing" will also be available from the USPTO upon request and payment of the fee set forth in 37 CFR 1.19(b)(3).

What is claimed is:

1. An isolated or purified polypeptide comprising an amino acid sequence having at least 90% sequence identity to SEQ ID NO:69 and wherein said polypeptide exhibits Alpha-L-arabinofuranosidase activity.

2. The isolated or purified polypeptide of claim 1, wherein the polypeptide is glycosylated, pegylated, or otherwise post-translationally modified.

3. The isolated or purified polypeptide of claim 1, wherein the polypeptide has Alpha-L-arabinofuranosidase activity at or below a pH of about 7.

4. The isolated or purified polypeptide of claim 1, wherein the polypeptide has Alpha-L-arabinofuranosidase activity at a temperature at or above 50 degrees Celsius.

5. The isolated or purified polypeptide of claim 1, wherein the polypeptide comprises SEQ ID NO:69.

6. A method of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan-, or mannan-decorating groups, the method comprising:
utilizing the isolated or purified polypeptide of claim 1 to at least partially degrade, cleave, or remove a polysaccharide, lignocellulose, cellulose, hemicellulose, lignin, starch, chitin, polyhydroxybutyrate, heteroxylans, glycoside, xylan-, glucan-, galactan-, or mannan-decorating group.

7. The method according to claim 6, wherein utilizing the isolated or purified polypeptide of claim 1 comprises utilizing the isolated and/or purified polypeptide of claim 1 at or below about pH 4.

8. The method according to claim 6, wherein utilizing the isolated or purified polypeptide of claim 1 comprises utilizing the isolated and/or purified polypeptide of claim 1 at a temperature at or above 50 degrees Celsius.

9. The method according to claim 6, wherein utilizing the isolated or purified polypeptide of claim 1 comprises utilizing a glycosylated, pegylated, or otherwise post-translationally modified isolated and/or purified polypeptide of claim 1.

10. The method according to claim 6, wherein utilizing the isolated or purified polypeptide of claim 1 comprises utilizing an isolated and/or purified polypeptide comprising SEQ ID NO:69.

11. An isolated or purified polypeptide having at least 95% sequence identity to the polypeptide of SEQ ID NO:69 and wherein the polypeptide displays Alpha-L-arabinofuranosidase activity.

* * * * *